(12) United States Patent
Wagner et al.

(10) Patent No.: US 7,381,687 B2
(45) Date of Patent: Jun. 3, 2008

(54) 3-HETEROARYL SUBSTITUTED 5-METHYLOXYMETHYL ISOXAZOLINES USED AS HERBICIDES

(75) Inventors: Oliver Wagner, Neustadt (DE);
Michael Rack, Heidelberg (DE);
Matthias Witschel, Bad Dürkheim (DE); Cyrill Zagar, Mannheim (DE);
Andreas Landes,
Römerberg-Heiligenstein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 106 days.

(21) Appl. No.: 10/512,451

(22) PCT Filed: Apr. 23, 2003

(86) PCT No.: PCT/EP03/04136

§ 371 (c)(1),
(2), (4) Date: Oct. 25, 2004

(87) PCT Pub. No.: WO03/090539

PCT Pub. Date: Nov. 6, 2003

(65) Prior Publication Data

US 2005/0165020 A1    Jul. 28, 2005

(30) Foreign Application Priority Data

Apr. 25, 2002 (DE) ................. 102 18 620

(51) Int. Cl.
*A01N 43/80* (2006.01)
*A01N 43/40* (2006.01)
*C07D 413/12* (2006.01)
*C07D 401/12* (2006.01)

(52) U.S. Cl. .................... 504/252; 546/272.1
(58) Field of Classification Search ............. 546/272.1; 504/252
See application file for complete search history.

(56) References Cited

U.S. PATENT DOCUMENTS 4,983,210 A    1/1991    Rheinheimer et al.

FOREIGN PATENT DOCUMENTS

| EP | 334 120 | 9/1989 |
|----|---------|--------|
| EP | 514 987 | 11/1992 |
| WO | 02/19825 | 3/2002 |

OTHER PUBLICATIONS

Patent abstract of Japan, JP 2001/158787.
KR 2002/19751, Derwent abstract.
JP 09/143171, English translation and Derwent abstract.

*Primary Examiner*—Patricia L. Morris
(74) *Attorney, Agent, or Firm*—Novak Druce + Quigg LLP

(57) ABSTRACT

3-Heteroaryl-substituted isoxazolines of the formula I

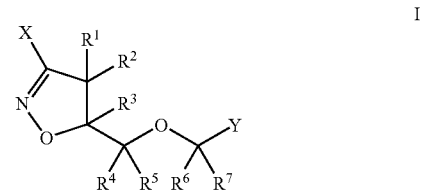

where:
X is substituted 5-membered heteroaryl having one to four nitrogen atoms or one to three nitrogen atoms and one oxygen or sulfur atom or one oxygen or sulfur atom; or
  substituted 6-membered heteroaryl having one to four nitrogen atoms;
  where the abovementioned 5-membered heteroaryl is not pyrazolyl or thienyl;
  $R^1$-$R^7$ are hydrogen, alkyl or haloalkyl;
  Y is unsubstituted or substituted aryl, or benzo[1,4] dioxonyl, benzo[1,3]dioxolanyl, 2,3-dihydrobenzofuranyl or benzimidazole; or
  unsubstituted or substituted 5- to 6-membered heteroaryl;
  and their agriculturally useful salts,
processes and intermediates for their preparation, and the use of these compounds or of the compositions comprising these compounds for controlling unwanted plants are described.

11 Claims, No Drawings

3-HETEROARYL SUBSTITUTED 5-METHYLOXYMETHYL ISOXAZOLINES USED AS HERBICIDES

The present invention relates to 3-heteroaryl-substituted isoxazolines of the formula I

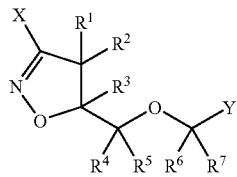

where:
- X is 5-membered heteroaryl having one to four nitrogen atoms or one to three nitrogen atoms and one oxygen or sulfur atom or one oxygen or sulfur atom; or
  is 6-membered heteroaryl having one to four nitrogen atoms,
  where the heterocycles are partially or fully halogenated and/or carry one to three substituents selected from the following group:
  cyano, nitro, hydroxyl, $C_1$-$C_8$-alkyl, $C_3$-$C_6$-cycloalkyl, $C_3$-$C_6$-halocycloalkyl, $C_2$-$C_8$-alkenyl, $C_2$-$C_8$-alkynyl, $C_1$-$C_8$-haloalkyl, $C_2$-$C_6$-haloalkenyl, $C_2$-$C_6$-haloalkynyl, $C_1$-$C_8$-cyanoalkyl, $C_2$-$C_8$-cyanoalkenyl, $C_1$-$C_8$-alkoxy, $C_1$-$C_8$-haloalkoxy, $C_1$-$C_8$-alkoxy-$C_1$-$C_8$-alkyl, $C_1$-$C_8$-alkoxy-$C_1$-$C_8$-alkoxy, amino, $C_1$-$C_8$-alkylamino, di($C_1$-$C_8$-alkyl)amino, $C_1$-$C_8$-alkylcarbonylamino, N—$C_1$-$C_8$-alkylcarbonyl-N—$C_1$-$C_8$-alkylamino, $C_1$-$C_8$-alkoxycarbonylamino, N—$C_1$-$C_8$-alkoxycarbonyl-N—$C_1$-$C_8$-alkylamino, amino-$C_1$-$C_8$-alkyl, $C_1$-$C_8$-alkylamino-$C_1$-$C_8$-alkyl, di($C_1$-$C_8$-alkyl)amino-$C_1$-$C_8$-alkyl, $C_1$-$C_8$-alkylthio, $C_1$-$C_8$-haloalkylthio, $C_1$-$C_8$-alkylthio-$C_1$-$C_8$-alkyl, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylsulfonyl-$C_1$-$C_8$-alkyl, $C_1$-$C_8$-alkylcarbonyl, $C_1$-$C_8$-alkoxycarbonyl, $C_1$-$C_8$-alkoxycarbonyl-$C_1$-$C_8$-alkyl, aminocarbonyl, $C_1$-$C_8$-alkylaminocarbonyl, di($C_1$-$C_8$-alkyl)aminocarbonyl, aminocarbonyl-$C_1$-$C_8$-alkyl, $C_1$-$C_8$-alkylaminocarbonyl-$C_1$-$C_8$-alkyl, di($C_1$-$C_8$-alkyl)aminocarbonyl-$C_1$-$C_8$-alkyl, carboxyl, carboxy-$C_1$-$C_8$-alkyl, phenyl, phenoxy, phenylthio, phenylamino, phenyl-$C_1$-$C_8$-alkyl, phenyl-$C_1$-$C_8$-alkoxy, 3- to 6-membered heterocyclyl and 5- to 6-membered heteroaryl, where the eight last-mentioned radicals for their part may be partially or fully halogenated and/or may carry one to three substituents selected from the group consisting of nitro, cyano, $C_1$-$C_8$-alkyl, $C_1$-$C_8$-alkoxy, $C_1$-$C_8$-haloalkyl, $C_1$-$C_8$-haloalkoxy, $C_1$-$C_8$-alkylthio, $C_1$-$C_8$-haloalkylthio, $C_1$-$C_8$-alkylsulfinyl, $C_1$-$C_8$-haloalkylsulfinyl, $C_1$-$C_8$-alkylsulfonyl and $C_1$-$C_8$-haloalkylsulfonyl;
  where the abovementioned 5-membered heteroaryl is not pyrazolyl or thienyl;
- $R^1$-$R^7$ are hydrogen, $C_1$-$C_6$-alkyl or $C_1$-$C_6$-haloalkyl;
- Y is aryl which may be partially or fully halogenated and/or may carry one to three substituents selected from the group consisting of cyano, nitro, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkoxycarbonyl, $C_1$-$C_6$-alkoxycarbonyl-$C_1$-$C_4$-alkoxy, $C_1$-$C_6$-alkylsulfonyl, phenyl, phenoxy and phenylcarbonyl, benzo[1,4]dioxonyl, benzo[1,3]dioxolanyl, 2,3-dihydrobenzofuranyl or benzimidazole; or
  5-membered heteroaryl having one to four nitrogen atoms or having one to three nitrogen atoms and one oxygen or sulfur atom or having one oxygen or sulfur atom; or
  6-membered heteroaryl having one to four nitrogen atoms; where the heterocycles may be partially or fully halogenated and/or may carry one to three substituents from the group consisting of cyano, $C_1$-$C_6$-alkyl, $C_1$-$C_6$-haloalkyl, $C_1$-$C_6$-alkoxy-$C_1$-$C_4$-alkyl, $C_1$-$C_6$-alkoxycarbonyl and $C_1$-$C_6$-alkylsulfonyl;

and their agriculturally useful salts.

Moreover, the invention relates to processes and intermediates for preparing compounds of the formula I, to compositions comprising them and to the use of these derivatives or of the compositions comprising them for controlling harmful plants.

3-phenyl-substituted isoxazolines are known from the literature, for example from EP 514 987. EP 334 120 discloses isoxazolines which are substituted in the 3-position by an unsubstituted heterocycle. Furthermore, JP 2001/158787 describes 3-pyrazolyl-substituted isoxazolines. WO 02/19825 and KR 2002/19751 disclose thienyl-substituted isoxazolines. JP 09/143,171 mentions isoxazolines which are substituted in the 3-position by a carbonyl or oxime group.

However, the herbicidal properties of the prior-art compounds and their compatibility with crop plants are not entirely satisfactory.

It is an object of the present invention to provide novel, in particular herbicidally active, compounds having improved properties.

We have found that this object is achieved by the 3-heteroaryl-substituted isoxazolines of the formula I and their herbicidal action.

Furthermore, we have found herbicidal compositions which comprise compounds I and have very good herbicidal action. Moreover, we have found processes for preparing these compositions and methods for controlling unwanted vegetation using the compounds I.

Depending on the substitution pattern, the compounds of the formula I may contain one or more centers of chirality, in which case they are present as enantiomers or mixtures of diastereomers. The invention provides both the pure enantiomers or diastereomers and their mixtures.

The compounds of the formula I may also be present in the form of their agriculturally useful salts, the type of salt generally being immaterial. In general, suitable salts are the salts of those cations or the acid addition salts of those acids whose cations and anions, respectively, have no adverse effect on the herbicidal action of the compounds I.

Suitable cations are in particular ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1$-$C_4$-alkyl) sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, nitrate, hydrogencarbonate, carbonate, hexafluorosilicate, hexafluorophosphate, benzoate, and the anions of $C_1$-$C_4$-alkanoic acids, preferably formate, acetate, propionate and butyrate.

The organic moieties mentioned for the substituents $R^1$-$R^7$ or as radicals on aryl or heteroaryl rings are collective terms for individual enumerations of the individual group members. All hydrocarbon chains, i.e. all alkyl, haloalkyl, cyanoalkyl, alkoxy, haloalkoxy, alkylcarbonyloxy, alkylthio, haloalkylthio, alkylsulfinyl, haloalkylsulfinyl, alkylsulfonyl, haloalkylsulfonyl, alkylcarbonyl, alkoxycarbonyl, haloalkoxycarbonyl, alkylamino, dialkylamino, alkylcarbonylamino, N-alkylcarbonyl-N-alkylamino; alkoxyalkyl, alkoxyalkoxy, alkylthioalkyl, dialkylaminoalkyl and alkoxycarbonylalkyl moieties, may be straight-chain or branched. Unless indicated otherwise, halogenated substituents preferably carry one to five identical or different halogen atoms. In each case, the term "halogen" denotes fluorine, chlorine, bromine or iodine.

Examples of other meanings are:

$C_1$-$C_4$-alkyl and the alkyl moieties of $C_1$-$C_4$-alkoxy-$C_1$-$C_4$-alkyl, $C_1$-$C_4$-alkylthio-$C_1$-$C_4$-alkyl, $C_1$-$C_4$-alkylsulfonyl-$C_1$-$C_4$-alkyl, $C_1$-$C_4$-alkylcarbonyl, $C_1$-$C_4$-alkylcarbonylamino, N—$C_1$-$C_4$-alkylcarbonyl-N—$C_1$-$C_4$-alkylamino, N—$C_1$-$C_4$-alkoxycarbonyl-N—$C_1$-$C_4$-alkylamino, amino-$C_1$-$C_4$-alkyl, $C_1$-$C_4$-alkylamino-$C_1$-$C_4$-alkyl, di($C_1$-$C_4$-alkyl)amino-$C_1$-$C_4$-alkyl, carboxy-$C_1$-$C_4$-alkyl, $C_1$-$C_4$-alkoxycarbonyl-$C_1$-$C_4$-alkyl, aminocarbonyl-$C_1$-$C_4$-alkyl, $C_1$-$C_4$-alkylaminocarbonyl-$C_1$-$C_4$-alkyl, di($C_1$-$C_4$-alkyl)aminocarbonyl-$C_1$-$C_4$-alkyl and phenyl-$C_1$-$C_4$-alkyl: for example methyl, ethyl, propyl, 1-methylethyl, butyl, 1-methylpropyl, 2-methylpropyl and 1,1-dimethylethyl;

$C_1$-$C_6$-alkyl: $C_1$-$C_4$-alkyl as mentioned above, and the alkyl moieties of $C_1$-$C_6$-alkoxy-$C_1$-$C_6$-alkyl, $C_1$-$C_6$-alkylthio-$C_1$-$C_6$-alkyl, $C_1$-$C_6$-alkylsulfonyl-$C_1$-$C_6$-alkyl, $C_1$-$C_6$-alkylcarbonyl, $C_1$-$C_6$-alkylcarbonylamino, N—$C_1$-$C_6$-alkylcarbonyl-N—$C_1$-$C_6$-alkylamino, N—$C_1$-$C_6$-alkoxycarbonyl-N—$C_1$-$C_6$-alkylamino, amino-$C_1$-$C_6$-alkyl, $C_1$-$C_6$-alkylamino-$C_1$-$C_6$-alkyl, di($C_1$-$C_6$-alkyl)amino-$C_1$-$C_6$-alkyl, carboxy-$C_1$-$C_6$-alkyl, $C_1$-$C_6$-alkoxycarbonyl-$C_1$-$C_6$-alkyl, aminocarbonyl-$C_1$-$C_6$-alkyl, $C_1$-$C_6$-alkylaminocarbonyl-$C_1$-$C_6$-alkyl, di($C_1$-$C_6$-alkyl)aminocarbonyl-$C_1$-$C_6$-alkyl and phenyl-$C_1$-$C_6$-alkyl; and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$-$C_8$-alkyl: $C_1$-$C_6$-alkyl as mentioned above, and the alkyl moieties of $C_1$-$C_8$-alkoxy-$C_1$-$C_8$-alkyl, $C_1$-$C_8$-alkylthio-$C_1$-$C_8$-alkyl, $C_1$-$C_8$-alkylsulfonyl-$C_1$-$C_8$-alkyl, $C_1$-$C_8$-alkylcarbonyl, $C_1$-$C_8$-alkylcarbonylamino, N—$C_1$-$C_8$-alkylcarbonyl-N—$C_1$-$C_8$-alkylamino, N—$C_1$-$C_8$-alkoxycarbonyl-N—$C_1$-$C_8$-alkylamino, amino-$C_1$-$C_8$-alkyl, $C_1$-$C_8$-alkylamino-$C_1$-$C_8$-alkyl, di($C_1$-$C_8$-alkyl)amino-$C_1$-$C_8$-alkyl, carboxy-$C_1$-$C_8$-alkyl, $C_1$-$C_8$-alkoxycarbonyl-$C_1$-$C_8$-alkyl, aminocarbonyl-$C_1$-$C_8$-alkyl, $C_1$-$C_8$-alkylaminocarbonyl-$C_1$-$C_8$-alkyl, di($C_1$-$C_8$-alkyl)aminocarbonyl-$C_1$-$C_8$-alkyl and phenyl-$C_1$-$C_8$-alkyl, and also, for example, heptyl, 2-methylhexyl, 3-methylhexyl, 2,2-dimethylpentyl, 2,3-dimethylpentyl, 2,4-dimethylpentyl, 3,3-dimethylpentyl, 2,2,3-trimethylbutyl, octyl, 2-methylheptyl, 3-methylheptyl, 4-methylheptyl, 2,2-dimethylhexyl, 2,3-dimethylhexyl, 2,4-dimethylhexyl, 3,3-dimethylhexyl, 2,2,3-trimethylpentyl, 2,3,3-trimethylpentyl, 2,3,4-trimethylpentyl and 2,2,3,3-tetramethylbutyl;

$C_3$-$C_6$-cycloalkyl: cyclopropyl, cyclobutyl, cyclopentyl and cyclohexyl;

$C_3$-$C_6$-halocycloalkyl: $C_3$-$C_6$-cycloalkyl, as mentioned above which is partially or fully substituted by fluorine, chlorine, bromine and/or iodine, i.e., for example, 2,2-difluorocyclopropyl, 2,2-dichlorocyclopropyl, 3-fluorocyclopentyl, 3-chlorocyclopentyl, 3,3-difluorocyclopentyl, 3,3-dichlorocyclopentyl, 4-fluorocyclohexyl, 4-chlorocyclohexyl, 4,4-difluorocyclohexyl and 4,4-dichlorocyclohexyl;

three- to six-membered heterocyclyl: a monocyclic saturated or partially unsaturated hydrocarbon having three to six ring members as mentioned above which may, in addition to carbon atoms, comprise one to four nitrogen atoms or one to three nitrogen atoms and one oxygen or sulfur atom or one oxygen and/or one sulfur atom or 2 oxygen or 2 sulfur atoms and which may be attached via a carbon atom or a nitrogen atom, for example 3- to 4-membered heterocyclyl:

2-oxiranyl, 2-oxetanyl, 3-oxetanyl, 2-aziridinyl, 3-thiethanyl, 1-azetinyl, 2-azetinyl;

5-membered saturated heterocyclyl attached via a carbon atom:

2-tetrahydrofuranyl, 3-tetrahydrofuranyl, 1,3-dioxolan-2-yl, 1,3-dioxolan-5-yl, 2-tetrahydrothienyl, 3-tetrahydrothienyl, 1,3-dithiolan-2-yl, 1,3-dithiolan-5-yl, 1,2-dithiolan-3-yl, 1,2-dithiolan-4-yl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl;

5-membered saturated heterocyclyl attached via a nitrogen atom:

1-pyrrolidinyl, 2-isothiazolidinyl, 2-isothiazolidinyl, 1-pyrazolidinyl, 3-oxazolidinyl, 3-thiazolidinyl, 1-imidazolidinyl, 1,2,4-triazolidin-1-yl, 1,2,4-oxadiazolidin-2-yl, 1,2,4-oxadiazolidin-4-yl, 1,2,4-thiadiazolidin-2-yl, 1,2,4-thiadiazolidin-4-yl;

5-membered partially unsaturated heterocyclyl attached via a carbon atom:

2,3-dihydrofur-2-yl, 2,3-dihydrofur-3-yl, 2,4-dihydrofur-4-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 4,5-dihydropyrrol-2-yl, 4,5-dihydropyrrol-3-yl, 2,5-dihydropyrrol-2-yl, 2,5-dihydropyrrol-3-yl, 4,5-dihydroisoxazol-3-yl, 2,5-dihydroisoxazol-3-yl, 2,3-dihydroisoxazol-3-yl, 4,5-dihydroisoxazol-4-yl, 2,5-dihydroisoxazol-4-yl, 2,3-dihydroisoxazol-4-yl, 4,5-dihydroisoxazol-5-yl, 2,5-dihydroisoxazol-5-yl, 2,3-dihydroisoxazol-5-yl, 4,5-dihydroisothiazol-3-yl, 2,5-dihydroisothiazol-3-yl, 2,3-dihydroisothiazol-3-yl, 4,5-dihydroisothiazol-4-yl, 2,5-dihydroisothiazol-4-yl, 2,3-dihydroisothiazol-4-yl, 4,5-dihydroisothiazol-5-yl, 2,5-dihydroisothiazol-5-yl, 2,3-dihydroisothiazol-5-yl, 2,3-dihydropyrazol-3-yl, 2,3-dihydropyrazol-4-yl, 2,3-dihydropyrazol-5-yl, 3,4-dihydropyrazol-3-yl, 3,4-dihydropyrazol-4-yl, 3,4-dihydropyrazol-5-yl, 4,5-dihydropyrazol-3-yl, 4,5-dihydropyrazol-4-yl, 4,5-dihydropyrazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2,3-dihydrooxozol-2-yl, 2,3-dihydrooxazol-4-yl, 2,3-dihydrooxazol-5-yl, 3,4-dihydrooxazol-2-yl, 3,4-dihydrooxazol-4-yl, 3,4-dihydrooxazol-5-yl, 2,3-dihydrothiazol-2-yl, 2,3-dihydrothiazol-4-yl, 2,3-dihydrothiazol-5-yl, 3,4-dihydrothiazol-2-yl, 3,4-dihydrothiazol-4-yl, 3,4-dihydrothiazol-5-yl;

5-membered partially unsaturated heterocyclyl attached via a nitrogen atom:

4,5-dihydropyrrol-1-yl, 2,5-dihydropyrrol-1-yl, 4,5-dihydroisoxazol-2-yl, 2,3-dihydroisoxazol-1-yl, 4,5-dihydroisothiazol-1-yl, 2,3-dihydroisothiazol-1-yl, 2,3-dihydropyrazol-1-yl, 2,3-dihydropyrozol-2-yl, 4,5-dihydropyrazol-1-yl, 3,4-dihydropyrazol-1-yl, 2,3-dihydroimidazol-1-yl, 2,3-dihydroimidozol-3-yl, 4,5-dihydroimidazol-1-yl, 2,5-dihydroimidazol-1-yl, 2,3-dihydrooxazol-3-yl, 3,4-dihydrooxazol-3-yl, 2,3-dihydrothiazol-3-yl, 3,4-dihydrothiazol-3-yl;

6-membered saturated heterocyclyl attached via a carbon atom:

2-piperidinyl, 3-piperidinyl, 4-piperidinyl, 1,3-dioxan-5-yl, 1,3-dithian-5-yl, 2-tetrahydropyranyl, 4-tetrahydropyranyl, 2-tetrahydrothiopyranyl, 4-tetrahydrothiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl, 1,2,4-hexahydrotriazin-3-yl, tetrahydro-1,3-oxazin-2-yl, tetrahydro-1,3-oxazin-6-yl, 2-morpholinyl, 3-morpholinyl;

6-membered saturated heterocyclyl attached via a nitrogen atom:

1-piperidinyl, 1-hexahydropyridazinyl, 1-hexahydropyrimidinyl, 1-piperazinyl, 1,3,5-hexahydrotriazin-1-yl, 1,2,4-hexahydrotriazin-1-yl, tetrahydro-1,3-oxazin-1-yl, 1-morpholinyl;

6-membered partially unsaturated heterocyclyl attached via a carbon atom:

2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl;

$C_2$-$C_6$-alkenyl: for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_8$-alkenyl: $C_2$-$C_6$-alkenyl as mentioned above, and also, for example, 1-heptenyl, 2-heptenyl, 3-heptenyl, 2-methyl-1-hexenyl, 2-methyl-2-hexenyl, 2-methyl-3-hexenyl, 2-methyl-4-hexenyl, 2-methyl-5-hexenyl, 3-methyl-1-hexenyl, 3-methyl-2-hexenyl, 3-methyl-3-hexenyl, 3-methyl-4-hexenyl, 3-methyl-5-hexenyl, 2,2-dimethyl-3-pentenyl, 2,2-dimethyl-4-pentenyl, 2,3-dimethyl-1-pentenyl, 2,3-dimethyl-2-pentenyl, 2,3-dimethyl-3-pentenyl, 2,3-dimethyl-4-pentenyl, 2,4-dimethyl-1-pentenyl, 2,4-dimethyl-2-pentenyl, 3,3-dimethyl-1-pentenyl, 2,2-dimethyl-3-methyl-3-butenyl, 1-octenyl, 2-octenyl, 3-octenyl, 4-octenyl, 2-methyl-1-heptenyl, 2-methyl-2-heptenyl, 2-methyl-3-heptenyl, 2-methyl-4-heptenyl, 2-methyl-5-heptenyl, 2-methyl-6-heptenyl, 3-methyl-1-heptenyl, 3-methyl-2-heptenyl, 3-methyl-3-heptenyl, 3-methyl-4-heptenyl, 3-methyl-5-heptenyl, 3-methyl-6-heptenyl, 4-methyl-1-heptenyl, 4-methyl-2-heptenyl, 4-methyl-3-heptenyl, 2,2-dimethyl-3-hexenyl, 2,2-dimethyl-4-hexenyl, 2,2-dimethyl-5-hexenyl, 2,3-dimethyl-1-hexenyl, 2,3-dimethyl-2-hexenyl, 2,3-dimethyl-3-hexenyl, 2,3-dimethyl-4-hexenyl, 2,3-dimethyl-5-hexenyl, 2,4-dimethyl-1-hexenyl, 2,4-dimethyl-2-hexenyl, 2,4-dimethyl-3-hexenyl, 2,4-dimethyl-4-hexenyl, 2,4-dimethyl-5-hexenyl, 3,3-dimethyl-1-hexenyl, 3,3-dimethyl-4-hexenyl, 3,3-dimethyl-5-hexenyl, 2,2,3-trimethyl-3-pentyl, 2,2,3-trimethyl-4-pentyl, 2,3,3-trimethyl-1-pentyl, 2,3,3-trimethyl-4-pentyl, 2,3,4-trimethyl-1-pentyl and 2,3,4-trimethyl-2-pentyl;

$C_2$-$C_6$-alkynyl: for example ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1- butynyl, 1-ethyl-2-butynyl, 1-ethyl-3-butynyl, 2-ethyl-3-butynyl and 1-ethyl-1-methyl-2-propynyl;

$C_2$-$C_8$-alkynyl: $C_2$-$C_6$-alkynyl as mentioned above, and also, for example, 1-heptynyl, 2-heptynyl, 3-heptynyl, 2-methyl-3-hexynyl, 2-methyl-4-hexynyl, 2-methyl-5-hexynyl, 3-methyl-1-hexynyl, 3-methyl-4-hexynyl, 3-methyl-5-hexynyl, 2,2-dimethyl-3-pentynyl, 2,2-dimethyl-4-pentynyl, 2,3-dimethyl-4-pentynyl, 3,3-dimethyl-1-pentynyl, 1-octynyl, 2-octynyl, 3-octynyl, 4-octynyl, 2-methyl-3-heptynyl, 2-methyl-4-heptynyl, 2-methyl-5-heptynyl, 2-methyl-6-heptynyl, 3-methyl-1-heptynyl, 3-methyl-4-heptynyl, 3-methyl-5-heptynyl, 3-methyl-6-heptynyl, 4-methyl-1-heptynyl, 4-methyl-2-heptynyl, 2,2-dimethyl-3-hexynyl, 2,2-dimethyl-4-hexynyl, 2,2-dimethyl-5-hexynyl, 2,3-dimethyl-4-hexynyl, 2,3-dimethyl-5-hexynyl, 2,4-dimethyl-5-hexynyl, 3,3-dimethyl-1-hexynyl, 3,3-dimethyl-4-hexynyl, 3,3-dimethyl-5-hexynyl, 2,2,3-trimethyl-4-pentynyl and 2,3,3-trimethyl-4-pentynyl;

$C_1$-$C_4$-haloalkyl: a $C_1$-$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$-$C_6$-haloalkyl: $C_1$-$C_4$-haloalkyl as mentioned above, and also, for example 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$-$C_8$-haloalyl: $C_1$-$C_6$-haloalyl as mentioned above, and also, for example, 7-fluoroheptyl, 7-chloroheptyl, 7-bromoheptyl, 7-iodoheptyl, perfluoroheptyl, 8-fluorooctyl, 8-chlorooctyl, 8-bromooctyl, 8-iodooctyl and heptadecafluorooctyl;

$C_2$-$C_6$-haloalkenyl: a $C_2$-$C_6$-alkenyl radical as mentioned above which is partially or fully substituted by fluorine, chlorine, bromine and/or iodine, for example 2-chlorovinyl, 2-chloroallyl, 3-chloroallyl, 2,3-dichloroallyl, 3,3-dichloroallyl, 2,3,3-trichloroallyl, 2,3-dichloro-2-butenyl, 2-bromovinyl, 2-bromoallyl, 3-bromoallyl, 2,3-dibromoallyl, 3,3-dibromoallyl, 2,3,3-tribromoallyl and 2,3-dibromo-2-butenyl;

$C_2$-$C_8$-haloalkenyl: a $C_1$-$C_6$-haloalkenyl radical as mentioned above, and also, for example, 2-chloro-1-heptenyl, 3-chloro-1-heptenyl, 2,3-dichloro-1-heptenyl, 3,3-dichloro-1-heptenyl, 2,3,3-trichloro-1-heptenyl, 2-bromo-1-heptenyl, 3-bromo-1-heptenyl, 2,3-dibromo-1-heptenyl, 3,3-dibromo-1-heptenyl, 2,3,3-tribromo-1-heptenyl, 2-chloro-1-octenyl, 3-chloro-1-octenyl, 2,3-dichloro-1-octenyl, 3,3-dichloro-1-octenyl, 2,3,3-trichloro-1-octenyl, 2-bromo-1-octenyl, 3-bromo-1-octenyl, 2,3-dibromo-1-octenyl, 3,3-dibromo-1-octenyl and 2,3,3-tribromo-1-octenyl;

$C_2$-$C_6$-haloalkynyl: a $C_2$-$C_6$-alkynyl radical as mentioned above which is partially or fully substituted by fluorine, chlorine, bromine and/or iodine, for example 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl and 6-iodohex-5-yn-1-yl;

$C_2$-$C_8$-haloalkynyl: a $C_1$-$C_6$-haloalkynyl radical as mentioned above, and also, for example, 7-fluorohept-5-yn-1-yl, 7-iodohept-6-yn-1-yl, 8-fluorooct-6-yn-1-yl and 8-iodooct-7-yn-1-yl;

$C_1$-$C_4$-cyanoalkyl: for example cyanomethyl, 1-cyanoethyl, 1-cyanopropyl, 2-cyanopropyl, 3-cyanopropyl, 1-cyanoprop-2-yl, 2-cyanoprop-2-yl, 1-cyanobutyl, 2-cyanobutyl, 3-cyanobutyl, 4-cyanobutyl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl or 2-cyanomethylprop-2-yl;

$C_1$-$C_6$-cyanoalkyl: $C_1$-$C_4$-cyanoalkyl as mentioned above, and also, for example, 5-cyanopentyl or 6-cyanohexyl;

$C_1$-$C_8$-cyanoalkyl: $C_1$-$C_6$-cyanoalkyl as mentioned above, and also, for example, 7-cyanoheptyl or 8-cyanooctyl;

$C_2$-$C_6$-cyanoalkenyl: a $C_2$-$C_6$-alkenyl radical as mentioned above which is substituted by cyano, for example 2-cyanovinyl, 2-cyanoallyl, 3-cyanoallyl, 2-cyanobut-2-enyl or 3-cyanobut-2-enyl;

$C_2$-$C_8$-cyanoalkenyl: a $C_2$-$C_6$-cyanoalkenyl radical as mentioned above, and also, for example, 2-cyano-1-heptenyl, 3-cyano-1-heptenyl, 2-cyano-1-octenyl or 3-cyano-1-octenyl;

$C_1$-$C_4$-alkoxy and the alkoxy moieties of $C_1$-$C_4$-alkoxy-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkoxycarbonylamino, N—$C_1$-$C_4$-alkoxycarbonyl-N—$C_1$-$C_4$-alkylamino, $C_1$-$C_4$-Alkoxycarbonyl($C_1$-$C_4$)alkoxy and phenyl-$C_1$-$C_4$-alkoxy: for example methoxy, ethoxy, propoxy, 1-methylethoxy, butoxy, 1-methylpropoxy, 2-methylpropoxy and 1,1-dimethylethoxy;

$C_1$-$C_6$-alkoxy: $C_1$-$C_4$-alkoxy as mentioned above, and the alkoxy moieties of $C_1$-$C_6$-alkoxy-$C_1$-$C_6$-alkyl, $C_1$-$C_6$-alkoxy-$C_1$-$C_6$-alkoxy, $C_1$-$C_6$-alkoxycarbonyl, $C_1$-$C_6$-alkoxycarbonyl-$C_1$-$C_6$-alkyl, $C_1$-$C_6$-alkoxycarbonylamino, N—$C_1$-$C_6$-alkoxycarbonyl-N—$C_1$-$C_6$-alkylamino, $C_1$-$C_6$-alkoxycarbonyl($C_1$-$C_6$)alkoxy and phenyl-$C_1$-$C_6$-alkoxy, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_8$-alkoxy: $C_1$-$C_6$-alkoxy as mentioned above, and the alkoxy moieties of $C_1$-$C_8$-alkoxy-$C_1$-$C_8$-alkyl, $C_1$-$C_8$-alkoxy-$C_1$-$C_8$-alkoxy, $C_1$-$C_8$-alkoxycarbonyl, $C_1$-$C_8$-alkoxycarbonyl-$C_1$-$C_8$-alkyl, $C_1$-$C_8$-alkoxycarbonylamino, N—$C_1$-$C_8$-alkoxycarbonyl-N—$C_1$-$C_8$-alkylamino and phenyl-$C_1$-$C_8$-alkoxy, for example, heptoxy, 2-methylhexoxy, 3-methylhexoxy, 2,2-dimethylpentoxy, 2,3-dimethylpentoxy, 2,4-dimethylpentoxy, 3,3-dimethylpentoxy, 2,2-dimethyl-3-methylbutoxy, octoxy, 2-methylheptoxy, 3-methylheptoxy, 4-methylheptoxy, 2,2-dimethylhexoxy, 2,3-dimethylhexoxy, 2,4-dimethylhexoxy, 3,3-dimethylhexoxy, 2,2-dimethyl-3-methylpentoxy, 2-methyl-3,3-dimethylpentoxy, 2,3,4-trimethylpentoxy and 2,2,3,3-tetramethylbutoxy;

$C_1$-$C_4$-haloalkoxy: a $C_1$-$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_6$-haloalkoxy: $C_1$-$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_8$-haloalkoxy: $C_1$-$C_6$-haloalkoxy as mentioned above, and also, for example, 7-fluoroheptoxy, 7-chloroheptoxy, 7-bromoheptoxy, 7-iodoheptoxy, perfluoroheptoxy, 8-fluorooctoxy, 8-chlorooctoxy, 8-bromooctoxy, 8-iodooctoxy and heptadecafluorooctoxy;

$C_1$-$C_6$-alkylamino and the alkylamino moieties of $C_1$-$C_6$-alkylamino-$C_1$-$C_6$-alkyl, N—$C_1$-$C_6$-alkylcarbonyl-N-$C_1$-$C_6$-alkylamino, $C_1$-$C_6$-alkylaminocarbonyl and $C_1$-$C_6$-alkylaminocarbonyl-$C_1$-$C_6$-alkyl, for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino and 1-ethyl-2-methylpropylamino;

$C_1$-$C_8$-alkylamino: $C_1$-$C_6$-alkylamino as mentioned above, and the alkylamino moieties of $C_1$-$C_8$-alkylamino-$C_1$-$C_8$-alkyl, N—$C_1$-$C_8$-alkylcarbonyl-N—$C_1$-$C_8$-alkylamino, N—$C_1$-$C_8$-alkoxycarbonyl-N—$C_1$-$C_8$-alkylamino, $C_1$-$C_8$-alkylaminocarbonyl and $C_1$-$C_8$-alkylaminocarbonyl-$C_1$-$C_8$-alkyl: for example, heptylamino, 2-methylhexylamino, 3-methylhexylamino, 2,2-dimethylpentylamino, 2,3-dimethylpentylamino, 2,4-dimethylpentylamino, 3,3-dimethylpentylamino, 2,2-dimethyl-3-methylbutylamino, octylamino, 2-methylheptylamino, 3-methylheptylamino, 4-methylheptylamino, 2,2-dimethylhexylamino, 2,3-dimethylhexylamino, 2,4-dimethylhexylamino, 3,3-dimethylhexylamino, 2,2-dimethyl-3-methylpentylamino, 2-methyl-3,3-dimethylpentylamino, 2,3,4-trimethylpentylamino and 2,2,3,3-tetramethylbutylamino;

di($C_1$-$C_4$-alkyl)amino and the dialkylamino moieties of di($C_1$-$C_4$-alkyl)amino-$C_1$-$C_4$-alkyl, di($C_1$-$C_4$-alkyl)aminocarbonyl and di($C_1$-$C_4$-alkyl)aminocarbonyl-$C_1$-$C_4$-alkyl: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino;

di($C_1$-$C_6$-alkyl)amino: di($C_1$-$C_4$-alkyl)amino as mentioned above, and the dialkylamino moieties of di($C_1$-$C_6$-alkyl)amino-$C_1$-$C_6$-alkyl, di($C_1$-$C_6$-alkyl)aminocarbonyl and di($C_1$-$C_6$-alkyl)aminocarbonyl-$C_1$-$C_6$-alkyl: for example, N,N-dipentylamino, N,N-dihexylamino, N-methyl-N-pentylamino, N-ethyl-N-pentylamino, N-methyl-N-hexylamino and N-ethyl-N-hexylamino;

di($C_1$-$C_8$-alkyl)amino: di($C_1$-$C_6$-alkyl)amino as mentioned above, and the dialkylamino moieties of di($C_1$-$C_8$-alkyl)amino-$C_1$-$C_8$-alkyl, di($C_1$-$C_8$-alkyl)aminocarbonyl and di($C_1$-$C_8$-alkyl)aminocarbonyl-$C_1$-$C_8$-alkyl: for example, N,N-diheptylamino, N,N-dioctylamino, N-methyl-N-heptylamino, N-ethyl-N-heptylamino, N-methyl-N-octylamino and N-ethyl-N-octylamino;

$C_1$-$C_4$-alkylthio and the alkylthio moieties of $C_1$-$C_4$-alkylthio-$C_1$-$C_4$-alkyl: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and the alkylthio moieties of $C_1$-$C_6$-alkylthio-$C_1$-$C_6$-alkyl and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_8$-alkylthio: $C_1$-$C_6$-alkylthio as mentioned above, and the alkylthio moieties of $C_1$-$C_8$-alkylthio-$C_1$-$C_8$-alkyl and also, for example, heptylthio, 2-methylhexylthio, 3-methylhexylthio, 2,2-dimethylpentylthio, 2,3-dimethylpentylthio, 2,4-dimethylpentylthio, 3,3-dimethylpentylthio, 2,2-dimethyl-3-methylbutylthio, octylthio, 2-methylheptylthio, 3-methylheptylthio 4-methylheptylthio, 2,2-dimethylhexylthio, 2,3-dimethylhexylthio, 2,4-dimethylhexylthio, 3,3-dimethylhexylthio, 2,2,3-trimethylpentylthio, 2,3,3-trimethylpentylthio, 2,3,4-trimethylpentylthio and 2,2,3,3-tetramethylbutylthio;

$C_1$-$C_4$-haloalkylthio: a $C_1$-$C_4$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio and nonafluorobutylthio;

$C_1$-$C_6$-haloalkylthio: $C_1$-$C_4$-haloalkylthio as mentioned above, and also, for example, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio and dodecafluorohexylthio;

$C_1$-$C_8$-haloalkylthio: $C_1$-$C_6$-haloalkylthio as mentioned above, and also, for example, 7-fluoroheptylthio, 7-chloroheptylthio, 7-bromoheptylthio, 7-iodoheptylthio, perfluoroheptylthio, 8-fluorooctylthio, 8-chlorooctylthio, 8-bromooctylthio, 8-iodooctylthio and heptadecafluorooctylthio;

$C_1$-$C_6$-alkylsulfinyl ($C_1$-$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_8$-alkylsulfinyl ($C_1$-$C_8$-alkyl-S(=O)—): $C_1$-$C_6$-alkylsulfinyl as mentioned above, and also, for example, heptylsulfinyl, 2-methylhexylsulfinyl, 3-methylhexylsulfinyl, 2,2-dimethylpentylsulfinyl, 2,3-dimethylpentylsulfinyl, 2,4-dimethylpentylsulfinyl, 3,3-dimethylpentylsulfinyl, 2,2-dimethyl-3-methylbutylsulfinyl, octylsulfinyl, 2-methylheptylsulfinyl, 3-methylheptylsulfinyl 4-methylheptylsulfinyl, 2,2-dimethylhexylsulfinyl, 2,3-dimethylhexylsulfinyl, 2,4-dimethylhexylsulfinyl, 3,3-dimethylhexylsulfinyl, 2,2,3-trimethylpentylsulfinyl, 2,3,3-trimethylpentylsulfinyl, 2,3,4-trimethylpentylsulfinyl and 2,2,3,3-tetramethylbutylsulfinyl;

$C_1$-$C_6$-haloalkylsulfinyl: $C_1$-$C_6$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl and dodecafluorohexylsulfinyl;

$C_1$-$C_8$-haloalkylsulfinyl: $C_1$-$C_6$-haloalkylsulfinyl as mentioned above, and also, for example 7-fluoroheptylsulfinyl, 7-chloroheptylsulfinyl, 7-bromoheptylsulfinyl, 7-iodoheptylsulfinyl, perfluoroheptylsulfinyl, 8-fluorooctylsulfinyl, 8-chlorooctylsulfinyl, 8-bromooctylsulfinyl, 8-iodooctylsulfinyl and perfluorooctylsulfinyl;

$C_1$-$C_6$-alkylsulfonyl ($C_1$-$C_6$-alkyl-S(=O)$_2$—) and the alkylsulfonyl moieties of $C_1$-$C_6$-alkylsulfonyl-$C_1$-$C_6$-alkyl: for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$-$C_8$-alkylsulfonyl ($C_1$-$C_8$-alkyl-S(=O)$_2$—): $C_1$-$C_6$-alkylsulfonyl as mentioned above, and the alkylsulfonyl moieties of $C_1$-$C_8$-alkylsulfonyl-$C_1$-$C_8$-alkyl: for example, heptylsulfonyl, 2-methylhexylsulfonyl, 3-methylhexylsulfonyl, 2,2-dimethylpentylsulfonyl, 2,3-dimethylpentylsulfonyl, 2,4-dimethylpentylsulfonyl, 3,3-dimethylpentylsulfonyl, 2,2-dimethyl-3-methylbutylsulfonyl, octylsulfonyl, 2-methylheptylsulfonyl, 3-methylheptylsulfonyl 4-methylheptylsulfonyl, 2,2-dimethylhexylsulfonyl, 2,3-dimethylhexylsulfonyl, 2,4-dimethylhexylsulfonyl, 3,3-dimethylhexylsulfonyl, 2,2,3-trimethylpentylsulfonyl, 2,3,3-trimethylpentylsulfonyl, 2,3,4-trimethylpentylsulfonyl and 2,2,3,3-tetramethylbutylsulfonyl;

$C_1$-$C_6$-haloalkylsulfonyl: a $C_1$-$C_6$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl;

$C_1$-$C_8$-haloalkylsulfonyl: $C_1$-$C_6$-haloalkylsulfonyl as mentioned above, and also, for example, 7-fluoroheptylsulfonyl, 7-chloroheptylsulfonyl, 7-bromoheptylsulfonyl, 7-iodoheptylsulfonyl, perfluoroheptylsulfonyl, 8-fluorooctylsulfonyl, 8-chlorooctylsulfonyl, 8-bromooctylsulfonyl, 8-iodooctylsulfonyl and heptadecafluorooctylsulfonyl;

aryl: a mono- to trinuclear aromatic carbocycle having 6 to 14 ring members, such as, for example, phenyl, naphthyl, anthracenyl and phenanthrenyl;

5-membered heteroaryl having one to four nitrogen atoms, or having one to three nitrogen atoms and one oxygen or sulfur atom or having one oxygen or sulfur atom is carbon atom-attached aromatic 5-membered heterocycles which, in addition to carbon atoms, may contain one to four nitrogen atoms or one to three nitrogen atoms and one sulfur or oxygen atom or one oxygen or one sulfur atom as ring members, for example aromatic 5-membered heterocycles which are attached via a carbon atom and contain one heteroatom, such as, for example, 2-furyl, 3-furyl, 2-thienyl, 3-thienyl, 2-pyrrolyl, 3-pyrrolyl;

for example aromatic 5-membered heterocycles which are attached via a carbon atom and contain two heteroatoms, such as, for example, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 3-pyrazolyl, 4-pyrazolyl, 5-pyrazolyl;

for example aromatic 5-membered heterocycles which are attached via a carbon atom and contain three heteroatoms, for example 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, tetrazol-2-yl;

for example aromatic 5-membered heterocycles which are attached via a carbon atom and contain four heteroatoms, such as, for example, tetrazol-2-yl;

6-membered heteroaryl containing one to four nitrogen atoms: for example 6-membered heterocycles which are attached via a carbon atom and which may, in addition to carbon atoms, contain one to four, preferably one to three, nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,4-triazin-6-yl and 1,2,4,5-tetrazinyl.

In a particular embodiment, the variables in the compounds of the formula I are as defined below, these definitions being, both on their own and in combination with one another, particular embodiments of the compounds of the formula I:

Preference is given to 3-heteroaryl-substituted isoxazolines of the formula I in which X is a 6-membered heteroaryl having one to four nitrogen atoms which is partially or fully halogenated and/or carries one to three substituents selected from the following group:

cyano, nitro, hydroxyl, $C_1$-$C_8$-alkyl, $C_3$-$C_6$-cycloalkyl, $C_3$-$C_6$-halocycloalkyl, $C_2$-$C_8$-alkenyl, $C_2$-$C_8$-alkynyl, $C_1$-$C_8$-haloalkyl, $C_2$-$C_6$-haloalkenyl, $C_2$-$C_6$-haloalkynyl, $C_1$-$C_8$-alkoxy, $C_1$-$C_8$-haloalkoxy, $C_1$-$C_8$-alkoxy-$C_1$-$C_8$-alkyl, amino, $C_1$-$C_8$-alkylamino, di($C_1$-$C_8$-alkyl)amino, amino-$C_1$-$C_8$-alkyl, $C_1$-$C_8$-alkylamino-$C_1$-$C_8$-alkyl, di($C_1$-$C_8$-alkyl)amino-$C_1$-$C_8$-alkyl, $C_1$-$C_8$-alkylthio, $C_1$-$C_8$-haloalkylthio, $C_1$-$C_8$-alkylthio-$C_1$-$C_8$-alkyl, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylsulfonyl-$C_1$-$C_8$-alkyl, $C_1$-$C_8$-alkoxycarbonyl, $C_1$-$C_8$-alkoxycarbonyl-$C_1$-$C_8$-alkyl, aminocarbonyl, $C_1$-$C_8$-alkylaminocarbonyl, di($C_1$-$C_8$-alkyl)aminocarbonyl, aminocarbonyl-$C_1$-$C_8$-alkyl, $C_1$-$C_8$-alkylaminocarbonyl-$C_1$-$C_8$-alkyl, di($C_1$-$C_8$-alkyl)aminocarbonyl-$C_1$-$C_8$-alkyl, carboxyl, carboxy-$C_1$-$C_8$-alkyl, phenyl, phenoxy, phenylthio, phenylamino, phenyl-$C_1$-$C_8$-alkyl, phenyl-$C_1$-$C_8$-alkoxy, 3- to 6-membered heterocyclyl and 5- to 6-membered heteroaryl, where the eight last-mentioned radicals for their part may be partially or fully halogenated and/or may carry one to three substituents selected from the group consisting of nitro, cyano, $C_1$-$C_8$-alkyl, $C_1$-$C_8$-alkoxy, $C_1$-$C_8$-haloalkyl, $C_1$-$C_8$-haloalkoxy, $C_1$-$C_8$-alkylthio, $C_1$-$C_8$-haloalkylthio, $C_1$-$C_8$-alkylsulfinyl, $C_1$-$C_8$-haloalkylsulfinyl, $C_1$-$C_8$-alkylsulfonyl, and $C_1$-$C_8$-haloalkylsulfonyl;

particular preference is given to 6-membered heteroaryl containing one to four nitrogen atoms which is partially or fully halogenated and/or carries one to three substituents selected from the following group:

cyano, nitro, hydroxyl, $C_1$-$C_6$-alkyl, $C_3$-$C_6$-cycloalkyl, $C_3$-$C_6$-halocycloalkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, amino, $C_1$-$C_6$-alkylamino, di($C_1$-$C_6$-alkyl)amino, amino-$C_1$-$C_6$-alkyl, $C_1$-$C_6$-alkylamino- $C_1$-$C_6$-alkyl, di($C_1$-$C_6$-alkyl)amino-$C_1$-$C_6$-alkyl, $C_1$-$C_6$-alkylthio, $C_1$-$C_6$-haloalkylthio, $C_1$-$C_6$-alkylthio-$C_1$-$C_6$-alkyl, $C_1$-$C_6$-alkylsulfinyl, $C_1$-$C_6$-alkylsulfonyl, $C_1$-$C_6$-alkylsulfonyl-$C_1$-$C_6$-alkyl, $C_1$-$C_6$-alkoxycarbonyl, $C_1$-$C_6$-alkoxycarbonyl-$C_1$-$C_6$-alkyl, aminocarbonyl, $C_1$-$C_6$-alkylaminocarbonyl, di($C_1$-$C_6$-alkyl)aminocarbonyl, aminocarbonyl-$C_1$-$C_6$-alkyl, $C_1$-$C_6$-alkylaminocarbonyl-$C_1$-$C_6$-alkyl, di($C_1$-$C_6$-alkyl)aminocarbonyl-$C_1$-$C_6$-alkyl, carboxyl and carboxy-$C_1$-$C_6$-alkyl;

especially preferred is 6-membered heteroaryl containing one to four nitrogen atoms which is partially or fully halogenated and/or carries one to three substituents selected from the following group:

cyano, nitro, hydroxyl, $C_1$-$C_6$-alkyl, $C_3$-$C_6$-cycloalkyl, $C_3$-$C_6$-halocycloalkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, amino, $C_1$-$C_6$-alkylamino, di($C_1$-$C_6$-alkyl)amino, $C_1$-$C_6$-alkylthio, $C_1$-$C_6$-haloalkylthio, $C_1$-$C_6$-alkylsulfinyl, $C_1$-$C_6$-alkylsulfonyl, $C_1$-$C_6$-alkoxycarbonyl, aminocarbonyl, $C_1$-$C_6$-alkylaminocarbonyl, di($C_1$-$C_6$-alkyl)aminocarbonyl, carboxyl and carboxy-$C_1$-$C_6$-alkyl.

very particular preference is given to 6-membered heteroaryl containing one to four nitrogen atoms which is partially halogenated and/or carries one or two substituents selected from the following group:

cyano, nitro, hydroxyl, $C_1$-$C_6$-alkyl, $C_3$-$C_6$-cycloalkyl, $C_3$-$C_6$-halocycloalkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, amino, $C_1$-$C_6$-alkylamino, di($C_1$-$C_6$-alkyl)amino, $C_1$-$C_6$-alkylthio, $C_1$-$C_6$-haloalkylthio, $C_1$-$C_6$-alkylsulfinyl, $C_1$-$C_6$-alkylsulfonyl, $C_1$-$C_6$-alkoxycarbonyl, aminocarbonyl, $C_1$-$C_6$-alkylaminocarbonyl, di($C_1$-$C_6$-alkyl)aminocarbonyl, carboxyl and carboxy-$C_1$-$C_6$-alkyl;

most preference is given to 6-membered heteroaryl containing one to four nitrogen atoms which is partially halogenated and/or carries one substituent selected from the following group:

cyano, nitro, hydroxyl, $C_1$-$C_6$-alkyl, $C_3$-$C_6$-cycloalkyl, $C_3$-$C_6$-halocycloalkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, amino, $C_1$-$C_6$-alkylamino, di($C_1$-$C_6$-alkyl)amino, $C_1$-$C_6$-alkylthio, $C_1$-$C_6$-haloalkylthio, $C_1$-$C_6$-alkylsulfinyl, $C_1$-$C_6$-alkylsulfonyl, $C_1$-$C_6$-alkoxycarbonyl, aminocarbonyl, $C_1$-$C_6$-alkylaminocarbonyl, di($C_1$-$C_6$-alkyl)aminocarbonyl, carboxyl and carboxy-$C_1$-$C_6$-alkyl.

Preference is also given to the 3-heteroaryl-substituted isoxazolines of the formula I in which X is 6-membered heteroaryl containing one to three nitrogen atoms, preferably 6-membered heteroaryl containing one or two nitrogen atoms, in particular pyridyl, pyrimidyl or pyrazinyl, very preferably pyridyl or pyrimidyl;

likewise very preferably pyridyl or pyrazinyl, very preferably pyridyl; and the 6-membered heteroaryl is substituted as described above;

extraordinary preference is given to 6-membered heteroaryl having one or two nitrogen atoms, in particular pyridyl or pyrazinyl, very preferably pyridyl; and the 6-membered heteroaryl is substituted as described above; and the 6-membered heteroaryl is attached to the isoxazoline skeleton in a position ortho or meta to a nitrogen.

Preference is also given to the 3-heteroaryl-substituted isoxazolines of the formula I in which X is 6-membered heteroaryl containing one or two nitrogen atoms which is partially or fully halogenated and/or carries one or two substituents selected from the following group:

cyano, nitro, hydroxyl, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, $C_1$-$C_6$-alkylsulfinyl and $C_1$-$C_6$-alkylsulfonyl; preferably cyano, nitro, hydroxyl, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, $C_1$-$C_6$-alkylsulfinyl and $C_1$-$C_6$-alkylsulfonyl; and which is attached to the isoxazoline skeleton in a position ortho or meta to a nitrogen of the 6-membered heteroaryl;

preferably 6-membered heteroaryl containing one or two nitrogen atoms which is partially halogenated and/or carries, in a position ortho to a nitrogen atom, one or two substituents selected from the following group:

cyano, nitro, hydroxyl, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio and $C_1$-$C_6$-alkylsulfinyl;

preferably cyano, nitro, hydroxyl, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio and $C_1$-$C_6$-alkylsulfinyl; and is attached to the isoxazoline skeleton in a position ortho or meta to a nitrogen of the 6-membered heteroaryl;

especially preferably 6-membered heteroaryl containing one or two nitrogen atoms which is partially halogenated and/or carries, in a position ortho to a nitrogen atom, one substituent selected from the following group:

cyano, nitro, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy or $C_1$-$C_6$-haloalkoxy and $C_1$-$C_6$-haloalkoxy;

preferably $C_1$-$C_6$-alkyl, $C_1$-$C_6$-haloalkyl, $C_1$-$C_6$-alkoxy and $C_1$-$C_6$-haloalkoxy; and is attached to the isoxazoline skeleton in a position ortho or meta to a nitrogen of the 6-membered heteroaryl.

Preference is also given to the 3-heteroaryl-substituted isoxazolines of the formula I, in which X is 6-membered heteroaryl containing one or two nitrogen atoms which is partially or fully halogenated and/or carries one or two substituents selected from the following group:

cyano, nitro, $C_1$-$C_6$-alkyl, $C_1$-$C_6$-haloalkyl, $C_2$-$C_6$-alkenyl and $C_2$-$C_6$-alkynyl; and which is attached to the isoxazoline skeleton in a position ortho or meta to a nitrogen of the 6-membered heteroaryl;

preferably 6-membered heteroaryl containing one or two nitrogen atoms which is partially halogenated and/or carries, in the position ortho to a nitrogen atom, one or two substituents selected from the following group:

cyano, nitro, $C_1$-$C_4$-alkyl, $C_1$-$C_4$-haloalkyl, $C_2$-$C_4$-alkenyl and $C_2$-$C_4$-alkynyl; and is attached to the isoxazoline skeleton in a position ortho or meta to a nitrogen of the 6-membered heteroaryl;

especially preferably 6-membered heteroaryl containing one or two nitrogen atoms which carries, in a position ortho to a nitrogen atom, one substituent selected from the following group: CN, $NO_2$, halogen, such as, for example, fluorine, chlorine, bromine, $C_1$-$C_4$-alkyl, such as, for example, methyl, ethyl, isopropyl, $C_1$-$C_4$-haloalkyl, such as, for example, trifluoromethyl, $C_2$-$C_4$-alkenyl, such as, for example, ethenyl, and $C_2$-$C_4$-alkynyl, such as, for example, ethynyl; and is attached to the isoxazoline skeleton in a position ortho or meta to a nitrogen of the 6-membered heteroaryl;

with extraordinary preference 6-membered heteroaryl containing one or two nitrogen atoms which carries, in a position ortho to a nitrogen atom, one substituent selected from the following group: F, Cl, Br, CN, $CH_3$, $C_2H_5$, $iC_3H_7$, $CF_3$, ethenyl and ethynyl; and is attached to the isoxazoline skeleton in a position ortho or meta to a nitrogen of the 6-membered heteroaryl.

Preference is also given to the 3-heteroaryl-substituted isoxazolines of the formula I in which X is a 5-membered heteroaryl having one to four nitrogen atoms or one to three nitrogen atoms and one sulfur or oxygen atom or one oxygen or sulfur atom, selected from the following group: pyrrolyl, furanyl, imidazolyl, oxazolyl, isoxazolyl, thiazolyl, isothiazolyl, 1,2,3-triazolyl, 1H-1,2,4-triazolyl, 4H-1,2,4-triazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl and 1H-tetrazolyl;

is partially or fully halogenated and/or carries one to three substituents selected from the following group:

cyano, nitro, hydroxyl, $C_1$-$C_8$-alkyl, $C_3$-$C_6$-cycloalkyl, $C_3$-$C_6$-halocycloalkyl, $C_2$-$C_8$-alkenyl, $C_2$-$C_8$-alkynyl, $C_1$-$C_8$-haloalkyl, $C_2$-$C_6$-haloalkenyl, $C_2$-$C_6$-haloalkynyl, $C_1$-$C_8$-alkoxy, $C_1$-$C_8$-haloalkoxy, $C_1$-$C_8$-alkoxy-$C_1$-$C_8$-alkyl, amino, $C_1$-$C_8$-alkylamino, di($C_1$-$C_8$-alkyl)amino, amino-$C_1$-$C_8$-alkyl, $C_1$-$C_8$-alkylamino-$C_1$-$C_8$-alkyl, di($C_1$-$C_8$-alkyl)amino-$C_1$-$C_8$-alkyl, $C_1$-$C_8$-alkylthio, $C_1$-$C_8$-haloalkylthio, $C_1$-$C_8$-alkylthio-$C_1$-$C_8$-alkyl, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylsulfonyl-$C_1$-$C_8$-alkyl, $C_1$-$C_8$-alkoxycarbonyl, $C_1$-$C_8$-alkoxycarbonyl-$C_1$-$C_8$-alkyl, aminocarbonyl, $C_1$-$C_8$-alkylaminocarbonyl, di($C_1$-$C_8$-alkyl)aminocarbonyl, aminocarbonyl-$C_1$-$C_8$-alkyl, $C_1$-$C_8$-alkylaminocarbonyl-$C_1$-$C_8$-alkyl, di($C_1$-$C_8$-alkyl)aminocarbonyl-$C_1$-$C_8$-alkyl, carboxyl, carboxy-$C_1$-$C_8$-alkyl, phenyl, phenoxy, phenylthio, phenylamino, phenyl-$C_1$-$C_8$-alkyl, phenyl-$C_1$-$C_8$-alkoxy, 3- to 6-membered heterocyclyl or 5- or 6-membered heteroaryl, where the eight last-mentioned radicals for their part may be partially or fully halogenated and/or may carry one to three substituents selected from the group consisting of nitro, cyano, $C_1$-$C_8$-alkyl, $C_1$-$C_8$-alkoxy, $C_1$-$C_8$-haloalkyl, $C_1$-$C_8$-haloalkoxy, $C_1$-$C_8$-alkylthio, $C_1$-$C_8$-haloalkylthio, $C_1$-$C_8$-alkylsulfinyl, $C_1$-$C_8$-haloalkylsulfinyl, $C_1$-$C_8$-alkylsulfonyl and $C_1$-$C_8$-haloalkylsulfonyl;

particular preference is given to 5-membered heteroaryl containing one to four nitrogen atoms or one to three nitrogen atoms and one oxygen or sulfur atom or one oxygen or sulfur atom from the following group: pyrrolyl, furanyl, imidazolyl, oxazolyl, isoxazolyl, thiazolyl, isothiazolyl, 1,2,3-triazolyl, 1H-1,2,4-triazolyl, 4H-1,2,4-triazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl and 1H-tetrazolyl;

where the 5-membered heteroaryl is partially or fully halogenated and/or carries one to three substituents selected from the following group:

cyano, nitro, hydroxyl, $C_1$-$C_6$-alkyl, $C_3$-$C_6$-cycloalkyl, $C_3$-$C_6$-halocycloalkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_6$-alkoxy, $C_1$-$C_6$-haloalkoxy, $C_1$-$C_6$-alkoxy-$C_1$-$C_6$-alkyl, amino, $C_1$-$C_6$-alkylamino, di($C_1$-$C_6$-alkyl)amino, amino-$C_1$-$C_6$-alkyl, $C_1$-$C_6$-alkylamino-$C_1$-$C_6$-alkyl, di($C_1$-$C_6$-alkyl)amino-$C_1$-$C_6$-alkyl, $C_1$-$C_6$-alkylthio, $C_1$-$C_6$-haloalkylthio, $C_1$-$C_6$-alkylthio-$C_1$-$C_6$-alkyl, $C_1$-$C_6$-alkylsulfinyl, $C_1$-$C_6$-alkylsulfonyl, $C_1$-$C_6$-alkylsulfonyl-$C_1$-$C_6$-alkyl, $C_1$-$C_6$-alkoxycarbonyl, $C_1$-$C_6$-alkoxycarbonyl-$C_1$-$C_6$-alkyl, aminocarbonyl, $C_1$-$C_6$-alkylaminocarbonyl, di($C_1$-$C_6$-alkyl)aminocarbonyl, aminocarbonyl-$C_1$-$C_6$-alkyl, $C_1$-$C_6$-alkylaminocarbonyl-$C_1$-$C_6$-alkyl, di($C_1$-$C_6$-alkyl)aminocarbonyl-$C_1$-$C_6$-alkyl, carboxyl and carboxy-$C_1$-$C_6$-alkyl;

especially preferred is 5-membered heteroaryl containing one to four nitrogen atoms or one to three nitrogen atoms and one oxygen or sulfur atom or one oxygen or sulfur atom from the following group: pyrrolyl, furanyl, imidazolyl, oxazolyl, isoxazolyl, thiazolyl, isothiazolyl, 1,2,3-triazolyl, 1H-1,2,4-triazolyl, 4H-1,2,4-triazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl and 1H-tetrazolyl, where the 5-membered heteroaryl is partially or fully halogenated and/or carries one to three substituents selected from the following group:

cyano, nitro, hydroxyl, $C_1$-$C_6$-alkyl, $C_3$-$C_6$-cycloalkyl, $C_3$-$C_6$-halocycloalkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, amino, $C_1$-$C_6$-alkylamino, di($C_1$-$C_6$-alkyl)amino, $C_1$-$C_6$-alkylthio, $C_1$-$C_6$-haloalkylthio, $C_1$-$C_6$-alkylsulfinyl, $C_1$-$C_6$-alkylsulfonyl, $C_1$-$C_6$-alkoxycarbonyl, aminocarbonyl, $C_1$-$C_6$-alkylaminocarbonyl, di($C_1$-$C_6$-alkyl)aminocarbonyl, carboxyl and carboxy-$C_1$-$C_6$-alkyl;

very particular preference is given to 5-membered heteroaryl containing one to four nitrogen atoms or one to three atoms and one oxygen or sulfur atom or one oxygen or sulfur atom from the following group: pyrrolyl, furanyl, imidazolyl, oxazolyl, isoxazolyl, thiazolyl, isothiazolyl, 1,2,3-triazolyl, 1H-1,2,4-triazolyl, 4H-1,2,4-triazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl and 1H-tetrazolyl;

where the 5-membered heteroaryl is partially halogenated and/or carries one or two substituents selected from the following group:

cyano, nitro, hydroxyl, $C_1$-$C_6$-alkyl, $C_3$-$C_6$-cycloalkyl, $C_3$-$C_6$-halocycloalkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, amino, $C_1$-$C_6$-alkylamino, di($C_1$-$C_6$-alkyl)amino, $C_1$-$C_6$-alkylthio, $C_1$-$C_6$-haloalkylthio, $C_1$-$C_6$-alkylsulfinyl, $C_1$-$C_6$-alkylsulfonyl, $C_1$-$C_6$-alkoxycarbonyl, aminocarbonyl, $C_1$-$C_6$-alkylaminocarbonyl, di($C_1$-$C_6$-alkyl)aminocarbonyl, carboxyl and carboxy-$C_1$-$C_6$-alkyl;

most preference is given to 5-membered heteroaryl containing one to four nitrogen atoms or one to three nitrogen atoms and one oxygen or sulfur atom or one oxygen or sulfur atom from the following group:

pyrrolyl, furanyl, imidazolyl, oxazolyl, isoxazolyl, thiazolyl, isothiazolyl, 1,2,3-triazolyl, 1H-1,2,4-triazolyl, 4H-1,2,4-triazolyl, 1,2,3-oxadiazolyl, 1,2,4-oxadiazolyl, 1,3,4-oxadiazolyl, 1,2,3-thiadiazolyl, 1,2,4-thiadiazolyl, 1,3,4-thiadiazolyl and 1H-tetrazolyl, where the 5-membered heteroaryl is partially halogenated and/or carries one substituent selected from the following group:
cyano, nitro, hydroxyl, $C_1$-$C_6$-alkyl, $C_3$-$C_6$-cycloalkyl, $C_3$-$C_6$-halocycloalkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, amino, $C_1$-$C_6$-alkylamino, di($C_1$-$C_6$-alkyl)amino, $C_1$-$C_6$-alkylthio, $C_1$-$C_6$-haloalkylthio, $C_1$-$C_6$-alkylsulfinyl, $C_1$-$C_6$-alkylsulfonyl, $C_1$-$C_6$-alkoxycarbonyl, aminocarbonyl, $C_1$-$C_6$-alkylaminocarbonyl, di($C_1$-$C_6$-alkyl)aminocarbonyl, carboxyl and carboxy-$C_1$-$C_6$-alkyl.

Preference is also given to 3-heteroaryl-substituted isoxazolines of the formula I in which X is 5-membered heteroaryl containing one to three nitrogen atoms or one or two nitrogen atoms and one oxygen or sulfur atom or one oxygen or sulfur atom, selected from the group consisting of $X^1$ to $X^6$

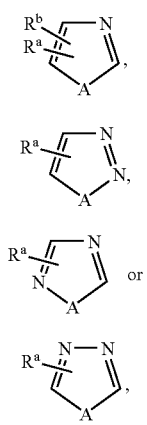

$X^1$ $X^2$ $X^3$ $X^4$ where A in $X^1$ to $X^4$ is $NR^d$, O or S,

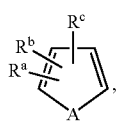

$X^5$ where A is $NR^d$ or O, and

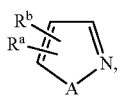

$X^6$ where A is O or S, and $R^a$ is halogen, cyano, nitro, hydroxyl, $C_1$-$C_6$-alkyl, $C_3$-$C_6$-cycloalkyl, $C_3$-$C_6$-halocycloalkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, amino, $C_1$-$C_6$-alkylamino, di($C_1$-$C_6$-alkyl)amino, $C_1$-$C_6$-alkylthio, $C_1$-$C_6$-haloalkylthio, $C_1$-$C_6$-alkylsulfinyl, $C_1$-$C_6$-alkylsulfonyl, $C_1$-$C_6$-alkoxycarbonyl, aminocarbonyl, $C_1$-$C_6$-alkylaminocarbonyl, di($C_1$-$C_6$-alkyl)aminocarbonyl, carboxyl or carboxy-$C_1$-$C_6$-alkyl;

$R^b$, $R^c$ are hydrogen or one of the substituents mentioned under $R^a$; and $R^d$ is hydrogen or $C_1$-$C_6$-alkyl.

Particular preference is given to the 3-heteroaryl-substituted isoxazolines of the formula I in which X is $X^1$, where $R^a$ is halogen, cyano, nitro, hydroxyl, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, $C_1$-$C_6$-alkylsulfinyl or $C_1$-$C_6$-alkylsulfonyl, $R^b$ is hydrogen or one of the substituents mentioned above under $R^a$; and $R^d$ is hydrogen or $C_1$-$C_6$-alkyl;
preferably hydrogen or $C_1$-$C_4$-alkyl;

with particular preference

X is $X^1$, where $R^a$ is halogen, $C_1$-$C_6$-alkyl, $C_1$-$C_6$-haloalkyl, $C_1$-$C_6$-alkoxy or $C_1$-$C_6$-haloalkoxy;

$R^b$ is hydrogen, halogen, $C_1$-$C_6$-alkyl, $C_1$-$C_6$-haloalkyl, $C_1$-$C_6$-alkoxy or $C_1$-$C_6$-haloalkoxy; and $R^d$ is hydrogen or $C_1$-$C_4$-alkyl.

Particular preference is also given to the 3-heteroaryl-substituted isoxazolines of the formula I in which X is $X^5$, where $R^a$ is halogen, cyano, nitro, hydroxyl, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, $C_1$-$C_6$-alkylsulfinyl or $C_1$-$C_6$-alkylsulfonyl;

$R^b$, $R^c$ are hydrogen or one of the substituents mentioned above under $R^a$; and $R^d$ is hydrogen or $C_1$-$C_6$-alkyl,
preferably hydrogen or $C_1$-$C_4$-alkyl;

preferably

X is $X^5$, where $R^a$ is halogen, cyano, nitro, hydroxyl, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, $C_1$-$C_6$-alkylsulfinyl or $C_1$-$C_6$-alkylsulfonyl;

$R^b$, $R^c$ are hydrogen or one of the substituents mentioned above under $R^a$; and $R^d$ is hydrogen or $C_1$-$C_4$-alkyl;

where the 5-membered heterocycle is attached to the isoxazoline skeleton in the position ortho to the heteroatom;

with particular preference

X is $X^5$, where $R^a$ is halogen, $C_1$-$C_6$-alkyl, $C_1$-$C_6$-haloalkyl, $C_1$-$C_6$-alkoxy or $C_1$-$C_6$-haloalkoxy;

$R^b$, $R^c$ are hydrogen, or one of the substituents mentioned above under $R^a$; and $R^d$ is hydrogen or $C_1$-$C_4$-alkyl;

where the 5-membered heterocycle is attached to the isoxazoline skeleton in the position ortho to the heteroatom.

Particular preference is also given to the 3-heteroaryl-substituted isoxazolines of the formula I in which X is $X^6$, where $R^a$ is halogen, cyano, nitro, hydroxyl, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, $C_1$-$C_6$-alkylsulfinyl or $C_1$-$C_6$-alkylsulfonyl;

$R^b$ is hydrogen, or one of the substituents mentioned above under $R^a$;

preferably

X is $X^6$, where $R^a$ is halogen, cyano, nitro, hydroxyl, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, $C_1$-$C_6$-alkylsulfinyl or $C_1$-$C_6$-alkylsulfonyl;

$R^b$ is hydrogen, or one of the substituents mentioned above under $R^a$;

where the 5-membered heterocycle is attached to the isoxazoline skeleton in the position ortho to a heteroatom;

with particular preference

X is $X^6$, where $R^a$ is halogen, $C_1$-$C_6$-alkyl, $C_1$-$C_6$-haloalkyl, $C_1$-$C_6$-alkoxy or $C_1$-$C_6$-haloalkoxy;

$R^b$ is hydrogen, or one of the substituents mentioned above under $R^a$;

where the 5-membered heterocycle is attached to the isoxazoline skeleton in the position ortho to a heteroatom.

Preference is also given to the 3-heteroaryl-substituted isoxazolines of the formula I in which $R^1$-$R^7$ are hydrogen, $C_1$-$C_4$-alkyl, such as, for example, methyl or ethyl, or $C_1$-$C_4$-haloalkyl, such as, for example, difluoromethyl, trifluoromethyl or trichloromethyl;
  particularly preferably hydrogen, methyl or trifluoromethyl;
  very preferably hydrogen;
  with particular preference, $R^1$, $R^2$, $R^4$-$R^7$ are hydrogen, methyl or trifluoromethyl and $R^3$ is hydrogen, methyl, ethyl or trifluoromethyl;
  with very particular preference, $R^1$, $R^2$, $R^4$-$R^7$ are hydrogen and $R^3$ is methyl.

Preference is also given to the 3-heteroaryl-substituted isoxazolines of the formula I in which Y is aryl which may be partially or fully halogenated and/or may carry one to three substituents from the group consisting of cyano, nitro, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_1$-$C_6$-haloalkoxy, $C_1$-$C_6$-alkoxycarbonyl-$C_1$-$C_6$-alkoxy, $C_1$-$C_6$-alkylsulfonyl, phenyl, phenoxy and phenylcarbonyl; or
  benzo[1,4]dioxanyl, benzo[1,3]dioxolanyl, 2,3-dihydrobenzofuranyl or benzimidazolyl; or
  5- or 6-membered heteroaryl containing one to four nitrogen, oxygen and/or sulfur atoms which may be partially or fully halogenated and/or may carry one to three substituents from the group consisting of $C_1$-$C_6$-alkyl, $C_1$-$C_6$-haloalkyl, $C_1$-$C_6$-alkoxy, $C_1$-$C_6$-alkoxy-$C_1$-$C_4$-alkyl, $C_1$-$C_6$-alkoxycarbonyl;
  particularly preferably aryl which may be partially halogenated and/or may carry one or two substituents from the group consisting of cyano, $C_1$-$C_6$-alkyl, $C_1$-$C_6$-haloalkyl and $C_1$-$C_6$-alkylsulfonyl; or
  benzo[1,4]dioxanyl, benzo[1,3]dioxolanyl, 2,3-dihydrobenzofuranyl or benzimidazolyl; or
  5- or 6-membered heteroaryl containing one to four nitrogen, oxygen and/or sulfur atoms which may be partially halogenated and/or may carry one or two substituents from the group consisting of $C_1$-$C_6$-alkyl, $C_1$-$C_6$-alkoxy-$C_1$-$C_4$-alkyl and $C_1$-$C_6$-alkoxycarbonyl;
  especially preferably aryl which may be partially halogenated and/or may carry one or two substituents from the group consisting of cyano, $C_1$-$C_4$-alkyl, $C_1$-$C_4$-haloalkyl and $C_1$-$C_4$-alkylsulfonyl; or benzo[1,4]dioxanyl, benzo[1,3]dioxolanyl, 2,3-dihydrobenzofuranyl or benzimidazolyl; or
  5- or 6-membered heteroaryl from the group consisting of pyrazolyl, thiazolyl, isoxazolyl, thiadiazolyl and pyridyl which may be partially halogenated and/or may carry one or two substituents from the group consisting of $C_1$-$C_6$-alkyl, $C_1$-$C_6$-alkoxy-$C_1$-$C_4$-alkyl and $C_1$-$C_6$-alkoxycarbonyl.

Preference is also given to the 3-heteroaryl-substituted isoxazolines of the formula I in which Y is aryl which may be partially or fully halogenated and/or may carry one to three substituents from the group consisting of cyano, nitro, $C_1$-$C_6$-alkyl or $C_2$-$C_6$-alkenyl, $C_2$-$C_6$-alkynyl, $C_1$-$C_6$-haloalkyl, $C_1$-$C_6$-alkoxy, $C_1$-$C_6$-haloalkoxy, $C_1$-$C_6$-alkoxycarbonyl-$C_1$-$C_4$-alkoxy, $C_1$-$C_6$-alkylsulfonyl, phenyl, phenoxy and phenylcarbonyl; preferably cyano, nitro, $C_1$-$C_6$-alkyl, $C_2$-$C_6$-alkenyl, $C_2$-$C_6$-alkynyl, $C_1$-$C_6$-haloalkyl or $C_1$-$C_6$-alkoxy;
  particularly preferably aryl which may be partially halogenated and/or may carry one or two substituents from the group consisting of cyano, $C_1$-$C_6$-alkyl, $C_1$-$C_6$-haloalkyl and $C_1$-$C_6$-alkylsulfonyl; preferably cyano, $C_1$-$C_6$-alkyl or $C_1$-$C_6$-haloalkyl;
  with particular preference aryl which may be partially halogenated and/or may carry one or two substituents from the group consisting of cyano, $C_1$-$C_4$-alkyl, $C_1$-$C_4$-haloalkyl and $C_1$-$C_4$-alkylsulfonyl; preferably cyano.

Preference is also given to 3-heteroaryl-substituted isoxazolines of the formula I in which Y is aryl which may be partially or fully halogenated and/or may carry one or two substituents from the group consisting of cyano, $C_1$-$C_6$-alkyl, $C_1$-$C_6$-haloalkyl, $C_1$-$C_6$-alkoxy and $C_1$-$C_6$-alkylsulfonyl; preferably cyano, $C_1$-$C_4$-alkyl and $C_1$-$C_4$-haloalkyl;
  particularly preferably aryl which is halogenated in one or both of the positions ortho to the point of attachment and/or may carry a substituent from the group consisting of cyano, $C_1$-$C_4$-alkyl, $C_1$-$C_4$-haloalkyl, $C_1$-$C_4$-alkoxy and $C_1$-$C_4$-alkoxysulfonyl;
  preferably cyano, $C_1$-$C_4$-alkyl and $C_1$-$C_4$-haloalkyl;
  with particular special preference aryl which is halogenated in one or both positions ortho to the point of attachment.

Preference is also given to the 3-heteroaryl-substituted isoxazolines of the formula I in which Y is phenyl which may be partially or fully halogenated and/or may carry one to three substituents from the group consisting of cyano, nitro, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkoxycarbonyl, $C_1$-$C_6$-alkoxycarbonyl-$C_1$-$C_4$-alkoxy, $C_1$-$C_6$-alkylsulfonyl, phenyl, phenoxy and phenylcarbonyl; preferably cyano, nitro, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_1$-$C_6$-haloalkoxy, $C_1$-$C_6$-alkylthio and $C_1$-$C_6$-haloalkylthio;
  particularly preferably phenyl which may be partially or fully halogenated and/or may carry one to three substituents from the group consisting of cyano, nitro, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_1$-$C_6$-alkoxycarbonyl; preferably cyano, nitro, $C_1$-$C_6$-alkyl, $C_2$-$C_6$-alkenyl, $C_2$-$C_6$-alkynyl, $C_1$-$C_6$-haloalkyl and $C_1$-$C_6$-alkoxy;
  with particular special preference phenyl which may be partially halogenated and/or may carry one or two substituents from the group consisting of cyano, $C_1$-$C_6$-alkyl, $C_1$-$C_6$-haloalkyl and $C_1$-$C_6$-alkylsulfonyl; preferably cyano, $C_1$-$C_6$-alkyl and $C_1$-$C_6$-haloalkyl.

Preference is also given to the 3-heteroaryl-substituted isoxazolines of the formula I in which Y is phenyl which may be partially or fully halogenated and/or may carry one or two substituents from the group consisting of cyano, $C_1$-$C_4$-alkyl and $C_1$-$C_4$-haloalkyl; particularly preferably phenyl which is halogenated in the 2- and/or 6-position to the point of attachment and/or may carry one substituent from the group consisting of cyano, $C_1$-$C_4$-alkyl and $C_1$-$C_4$-haloalkyl;
  with particular special preference phenyl which is halogenated in the 2- and/or 6-position to the point of attachment.

Preference is also given to the 3-heteroaryl-substituted isoxazolines of the formula I in which Y is naphthyl which may be partially or fully halogenated and/or may carry one to three substituents from the group consisting of cyano, nitro, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_1$-$C_6$-haloalkoxy, $C_1$-$C_6$-alkylthio and $C_1$-$C_6$-haloalkylthio; particularly preferably naphthyl which may be partially or fully halogenated and/or may carry one to three substituents from the group consisting of cyano, nitro, $C_1$-$C_6$-alkyl, $C_2$-$C_6$-alkenyl, $C_2$-$C_6$-alkynyl, $C_1$-$C_6$-haloalkyl and $C_1$-$C_6$-alkoxy;
  with particular special preference naphthyl which may be partially halogenated and/or may carry one or two substituents from the group consisting of cyano, $C_1$-$C_6$-alkyl and $C_1$-$C_6$-haloalkyl.

Preference is also given to the 3-heteroaryl-substituted isoxazolines of the formula I in which Y is naphthyl which may be partially or fully halogenated and/or may carry one or two substituents from the group consisting of cyano, $C_1$-$C_4$-alkyl and $C_1$-$C_4$-haloalkyl; particularly preferably naphthyl which is halogenated in one or both of the positions ortho to the point of attachment and/or may carry one substituent from the group consisting of cyano, $C_1$-$C_4$-alkyl and $C_1$-$C_4$-haloalkyl;
  with particular special preference naphthyl which is halogenated in one or both of the positions ortho to the point of attachment.

Preference is also given to the 3-heteroaryl-substituted isoxazolines of the formula I in which Y is 5-membered heteroaryl having one to four nitrogen atoms or having one to 3 nitrogen atoms and one oxygen or sulfur atom or one oxygen or sulfur atom; or 6-membered heteroaryl having one to 4 nitrogen atoms; where the heterocycles may be partially or fully halogenated and/or may carry one to three substituents from the group consisting of cyano, $C_1$-$C_6$-alkyl, $C_1$-$C_6$-haloalkyl, $C_1$-$C_6$-alkoxy, $C_1$-$C_6$-alkoxy-$C_1$-$C_4$-alkyl, $C_1$-$C_6$-alkoxycarbonyl and $C_1$-$C_6$-alkylsulfonyl;
  particularly preferably 5-membered heteroaryl having one to four nitrogen atoms or having one to 3 nitrogen atoms and one oxygen or sulfur atom or one oxygen or sulfur atom; or
  6-membered heteroaryl having one to 4 nitrogen atoms;
  where the heterocycles may be partially or fully halogenated and/or may carry one to three substituents from the group consisting of cyano, $C_1$-$C_6$-alkyl, $C_1$-$C_6$-haloalkyl, $C_1$-$C_6$-alkoxy-$C_1$-$C_4$-alkyl and $C_1$-$C_6$-alkoxycarbonyl;
  with particular special preference 5- or 6-membered heteroaryl from the group consisting of pyrazolyl, thiazolyl, isoxazolyl, thiadiazolyl and pyridyl, where the 5- or 6-membered heteroaryl may be partially halogenated and/or may carry one or two substituents from the group consisting of cyano, $C_1$-$C_4$-alkyl, $C_1$-$C_4$-haloalkyl, $C_1$-$C_4$-alkoxy-$C_1$-$C_4$-alkyl and $C_1$-$C_4$-alkoxycarbonyl.

Preference is also given to the 3-heteroaryl-substituted isoxazolines of the formula I in which X is 6-membered heteroaryl having one to three nitrogen atoms,
  preferably 6-membered heteroaryl having one or two nitrogen atoms,
  in particular pyridyl, pyrimidyl and pyrazinyl, very preferably pyridyl and pyrimidyl;
  where the 6-membered heteroaryl is substituted as described above;

$R^1$-$R^7$ are hydrogen, $C_1$-$C_4$-alkyl, such as, for example, methyl or ethyl, or $C_1$-$C_4$-haloalkyl, such as, for example, difluoromethyl, trifluoromethyl or trichloromethyl; particularly preferably hydrogen, methyl or trifluoromethyl;
  very preferably hydrogen;
  with particular preference, $R^1$, $R^2$, $R^4$-$R^7$ are hydrogen, methyl or trifluoromethyl and $R^3$ is hydrogen, methyl, ethyl or trifluoromethyl; with very particular preference, $R^1$, $R^2$, $R^4$-$R^7$ are hydrogen and $R^3$ is methyl; and Y is aryl which may be partially or fully halogenated and/or may carry one or two substituents from the group consisting of cyano, $C_1$-$C_4$-alkyl and $C_1$-$C_4$-haloalkyl; particularly preferably aryl which is halogenated in one or both of the positions ortho to the point of attachment and/or may carry one substituent from the group consisting of cyano, $C_1$-$C_4$-alkyl and $C_1$-$C_4$-haloalkyl;
  with particular special preference aryl which is halogenated in one or both of the positions ortho to the point of attachment.

Preference is also given to the 3-heteroaryl-substituted isoxazolines of the formula I in which X is $X^1$, where
$R^a$ is halogen, cyano, nitro, hydroxyl, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, $C_1$-$C_6$-alkylsulfinyl or $C_1$-$C_6$-alkylsulfonyl;
$R^b$ is hydrogen, or one of the substituents mentioned under $R^a$; and
$R^d$ is hydrogen or $C_1$-$C_6$-alkyl,
  preferably hydrogen or $C_1$-$C_4$-alkyl;

with particular preference
X is $X^1$, where
$R^a$ is halogen, $C_1$-$C_6$-alkyl, $C_1$-$C_6$-haloalkyl, $C_1$-$C_6$-alkoxy or $C_1$-$C_6$-haloalkoxy;
$R^b$ is hydrogen, halogen, $C_1$-$C_6$-alkyl, $C_1$-$C_6$-haloalkyl, $C_1$-$C_6$-alkoxy or $C_1$-$C_6$-haloalkoxy; and
$R^d$ is hydrogen or $C_1$-$C_4$-alkyl;

$R^1$-$R^7$ are hydrogen, $C_1$-$C_4$-alkyl, such as, for example, methyl or ethyl, or $C_1$-$C_4$-haloalkyl, such as, for example, difluoromethyl, trifluoromethyl or trichloromethyl; particularly preferably hydrogen, methyl or trifluoromethyl; very preferably hydrogen;
  with particular preference, $R^1$, $R^2$, $R^4$-$R^7$ are hydrogen, methyl or trifluoromethyl and $R^3$ is hydrogen, methyl, ethyl or trifluoromethyl; with very particular preference, $R^1$, $R^2$, $R^4$-$R^7$ are hydrogen and $R^3$ is methyl; and Y is aryl which may be partially or fully halogenated and/or may carry one or two substituents from the group consisting of cyano, $C_1$-$C_4$-alkyl and $C_1$-$C_4$-haloalkyl; particlarly preferably aryl which is halogenated in one or both of the positions ortho to the point of attachment and/or may carry one substituent from the group consisting of cyano, $C_1$-$C_4$-alkyl and $C_1$-$C_4$-haloalkyl; with particular special preference aryl which is halogenated in one or both of the positions ortho to the point of attachment.

Particular preference is also given to the 3-heteroaryl-substituted isoxazolines of the formula I in which X is X⁵, where
R$^a$ is halogen, cyano, nitro, hydroxyl, C$_1$-C$_6$-alkyl, C$_1$-C$_6$-haloalkyl, C$_1$-C$_6$-alkoxy, C$_1$-C$_6$-haloalkoxy, amino, C$_1$-C$_6$-alkylamino, di(C$_1$-C$_6$-alkyl)amino, C$_1$-C$_6$-alkylthio, C$_1$-C$_6$-alkylsulfinyl or C$_1$-C$_6$-alkylsulfonyl;
R$^b$, R$^c$ are hydrogen, or one of the substituents mentioned above under R$^a$; and
R$^d$ is hydrogen or C$_1$-C$_6$-alkyl,
preferably hydrogen or C$_1$-C$_4$-alkyl;

preferably
X is X⁵, where
R$^a$ is halogen, cyano, nitro, hydroxyl, C$_1$-C$_6$-alkyl, C$_1$-C$_6$-haloalkyl, C$_1$-C$_6$-alkoxy, C$_1$-C$_6$-haloalkoxy, amino, C$_1$-C$_6$-alkylamino, di(C$_1$-C$_6$-alkyl)amino, C$_1$-C$_6$-alkylthio, C$_1$-C$_6$-alkylsulfinyl or C$_1$-C$_6$-alkylsulfonyl;
R$^b$, R$^c$ are hydrogen, or one of the substituents mentioned above under R$^a$; and
R$^d$ is hydrogen or C$_1$-C$_4$-alkyl;

where the 5-membered heterocycle is attached to the isoxazoline skeleton in the position ortho to the heteroatom;

with particular preference
X is X⁵, where
R$^a$ is halogen, C$_1$-C$_6$-alkyl, C$_1$-C$_6$-haloalkyl, C$_1$-C$_6$-alkoxy or C$_1$-C$_6$-haloalkoxy;
R$^b$, R$^c$ are hydrogen, or one of the substituents mentioned above under R$^a$; and
R$^d$ is hydrogen or C$_1$-C$_4$-alkyl;

where the 5-membered heterocycle is attached to the isoxazoline skeleton in the position ortho to the heteroatom,
R$^1$-R$^7$ are hydrogen, C$_1$-C$_4$-alkyl, such as, for example, methyl or ethyl, or C$_1$-C$_4$-haloalkyl, such as, for example, difluoromethyl, trifluoromethyl or trichloromethyl;
particularly preferably hydrogen, methyl or trifluoromethyl;
very preferably hydrogen;
with particular preference, R$^1$, R$^2$, R$^4$-R$^7$ are hydrogen, methyl or trifluoromethyl and R$^3$ is hydrogen, methyl, ethyl or trifluoromethyl; with very particular preference, R$^1$, R$^2$, R$^4$-R$^7$ are hydrogen and R$^3$ is methyl; and
Y is aryl which may be partially or fully halogenated and/or may carry one or two substituents from the group consisting of cyano, C$_1$-C$_4$-alkyl and C$_1$-C$_4$-haloalkyl;
particularly preferably aryl which is halogenated in one or both of the positions ortho to the point of attachment and/or may carry one substituent from the group consisting of cyano, C$_1$-C$_4$-alkyl and C$_1$-C$_4$-haloalkyl;
with particular special preference aryl which is halogenated in one or both of the positions ortho to the point of attachment.

Particular preference is also given to the 3-heteroaryl-substituted isoxazolines of the formula I in which
X is X⁶, where
R$^a$ is halogen, cyano, nitro, hydroxyl, C$_1$-C$_6$-alkyl, C$_1$-C$_6$-haloalkyl, C$_1$-C$_6$-alkoxy, C$_1$-C$_6$-haloalkoxy, amino, C$_1$-C$_6$-alkylamino, di(C$_1$-C$_6$-alkyl)amino, C$_1$-C$_6$-alkylthio, C$_1$-C$_6$-alkylsulfinyl or C$_1$-C$_6$-alkylsulfonyl,
R$^b$ is hydrogen, or one of the substituents mentioned above under R$^a$;

preferably
X is X⁶, where
R$^a$ is halogen, cyano, nitro, hydroxyl, C$_1$-C$_6$-alkyl, C$_1$-C$_6$-haloalkyl, C$_1$-C$_6$-alkoxy, C$_1$-C$_6$-haloalkoxy, amino, C$_1$-C$_6$-alkylamino, di(C$_1$-C$_6$-alkyl)amino, C$_1$-C$_6$-alkylthio, C$_1$-C$_6$-alkylsulfinyl or C$_1$-C$_6$-alkylsulfonyl;
R$^b$ is hydrogen, or one of the substituents mentioned above under R$^a$;

where the 5-membered heterocycle is attached to the isoxazoline skeleton in the position ortho to a heteroatom;

with particular preference
X is X⁶, where
R$^a$ is halogen, C$_1$-C$_6$-alkyl, C$_1$-C$_6$-haloalkyl, C$_1$-C$_6$-alkoxy or C$_1$-C$_6$-haloalkoxy,
R$^b$ is hydrogen, or one of the substituents mentioned above under R$^a$;

where the 5-membered heterocycle is attached to the isoxazoline skeleton in a position ortho to a heteroatom;
R$^1$-R$^7$ are hydrogen, C$_1$-C$_4$-alkyl, such as, for example, methyl or ethyl, or C$_1$-C$_4$-haloalkyl, such as, for example, difluoromethyl, trifluoromethyl or trichloromethyl;
particularly preferably hydrogen, methyl or trifluoromethyl;
very preferably hydrogen;
with particular preference, R$^1$, R$^2$, R$^4$-R$^7$ are hydrogen, methyl or trifluoromethyl and R$^3$ is hydrogen, methyl, ethyl or trifluoromethyl; with very particular preference, R$^1$, R$^2$, R$^4$-R$^7$ are hydrogen and R$^3$ is methyl, and
Y is aryl which may be partially or fully halogenated and/or may carry one or two substituents from the group consisting of cyano, C$_1$-C$_4$-alkyl and C$_1$-C$_4$-haloalkyl;
particularly preferably aryl which is halogenated in one or both of the positions ortho to the point of attachment and/or may carry one substituent from the group consisting of cyano, C$_1$-C$_4$-alkyl and C$_1$-C$_4$-haloalkyl;
with particular special preference aryl which is halogenated in one or both of the positions ortho to the point of attachment.

Most preferred are the compounds of the formula I.a (corresponds to the formula I where R$^1$, R$^2$, R$^4$-R$^7$=hydrogen, R$^3$=methyl), in particular the compounds of the formulae I.a.1 to I.a.234 of Table 1, where the definitions of the variables R$^1$ to R$^7$, X and Y are of particular importance for the compounds according to the invention not only in combination with one another but in each case also on their own.

TABLE 1

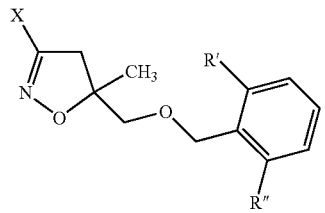

I.a

| No. | X | R' | R'' |
|---|---|---|---|
| I.a.1 | 4-fluoropyrid-3-yl | H | H |
| I.a.2 | 4-fluoropyrid-3-yl | F | H |
| I.a.3 | 4-fluoropyrid-3-yl | F | F |
| I.a.4 | 3-chloropyrid-2-yl | H | H |
| I.a.5 | 3-chloropyrid-2-yl | F | H |
| I.a.6 | 3-chloropyrid-2-yl | F | F |
| I.a.7 | 4-chloropyrid-3-yl | H | H |
| I.a.8 | 4-chloropyrid-3-yl | F | H |
| I.a.9 | 4-chloropyrid-3-yl | F | F |
| I.a.10 | 4-bromopyrid-3-yl | H | H |
| I.a.11 | 4-bromopyrid-3-yl | F | H |
| I.a.12 | 4-bromopyrid-3-yl | F | F |
| I.a.13 | 2-methylpyrid-3-yl | H | H |

TABLE 1-continued

I.a

| No. | X | R' | R" |
|---|---|---|---|
| I.a.14 | 2-methylpyrid-3-yl | F | H |
| I.a.15 | 2-methylpyrid-3-yl | F | F |
| I.a.16 | 4-methylpyrid-3-yl | H | H |
| I.a.17 | 4-methylpyrid-3-yl | F | H |
| I.a.18 | 4-methylpyrid-3-yl | F | F |
| I.a.19 | 2-trifluoromethylpyrid-3-yl | H | H |
| I.a.20 | 2-trifluoromethylpyrid-3-yl | F | H |
| I.a.21 | 2-trifluoromethylpyrid-3-yl | F | F |
| I.a.22 | 2-methoxypyrid-3-yl | H | H |
| I.a.23 | 2-methoxypyrid-3-yl | F | H |
| I.a.24 | 2-methoxypyrid-3-yl | F | F |
| I.a.25 | 2,6-difluoropyrid-3-yl | H | H |
| I.a.26 | 2,6-difluoropyrid-3-yl | F | H |
| I.a.27 | 2,6-difluoropyrid-3-yl | F | F |
| I.a.28 | 2,3-dichloropyrid-4-yl | H | H |
| I.a.29 | 2,3-dichloropyrid-4-yl | F | H |
| I.a.30 | 2,3-dichloropyrid-4-yl | F | F |
| I.a.31 | 2,4-dichloropyrid-3-yl | H | H |
| I.a.32 | 2,4-dichloropyrid-3-yl | F | H |
| I.a.33 | 2,4-dichloropyrid-3-yl | F | F |
| I.a.34 | 2,6-dichloropyrid-3-yl | H | H |
| I.a.35 | 2,6-dichloropyrid-3-yl | F | H |
| I.a.36 | 2,6-dichloropyrid-3-yl | F | F |
| I.a.37 | 2,6-dibromopyrid-3-yl | H | H |
| I.a.38 | 2,6-dibromopyrid-3-yl | F | H |
| I.a.39 | 2,6-dibromopyrid-3-yl | F | F |
| I.a.40 | 2,4-dimethylpyrid-3-yl | H | H |
| I.a.41 | 2,4-dimethylpyrid-3-yl | F | H |
| I.a.42 | 2,4-dimethylpyrid-3-yl | F | F |
| I.a.43 | 2,6-dimethylpyrid-3-yl | H | H |
| I.a.44 | 2,6-dimethylpyrid-3-yl | F | H |
| I.a.45 | 2,6-dimethylpyrid-3-yl | F | F |
| I.a.46 | 2-Fluoro-6-methylpyrid-3-yl | H | H |
| I.a.47 | 2-Fluoro-6-methylpyrid-3-yl | F | H |
| I.a.48 | 2-Fluoro-6-methylpyrid-3-yl | F | F |
| I.a.49 | 2-chloro-6-methylpyrid-3-yl | H | H |
| I.a.50 | 2-chloro-6-methylpyrid-3-yl | F | H |
| I.a.51 | 2-chloro-6-methylpyrid-3-yl | F | F |
| I.a.52 | 3-chloro-6-methylpyrid-2-yl | H | H |
| I.a.53 | 3-chloro-6-methylpyrid-2-yl | F | H |
| I.a.54 | 3-chloro-6-methylpyrid-2-yl | F | F |
| I.a.55 | 3-chloro-5-methylpyrid-4-yl | H | H |
| I.a.56 | 3-chloro-5-methylpyrid-4-yl | F | H |
| I.a.57 | 3-chloro-5-methylpyrid-4-yl | F | F |
| I.a.58 | 2-bromo-6-methylpyrid-3-yl | H | H |
| I.a.59 | 2-bromo-6-methylpyrid-3-yl | F | H |
| I.a.60 | 2-bromo-6-methylpyrid-3-yl | F | F |
| I.a.61 | 2-methyl-3-chloropyrid-4-yl | H | H |
| I.a.62 | 2-methyl-3-chloropyrid-4-yl | F | H |
| I.a.63 | 2-methyl-3-chloropyrid-4-yl | F | F |
| I.a.64 | 2-methyl-6-chloropyrid-3-yl | H | H |
| I.a.65 | 2-methyl-6-chloropyrid-3-yl | F | H |
| I.a.66 | 2-methyl-6-chloropyrid-3-yl | F | F |
| I.a.67 | 2,4,6-trichloropyrid-3-yl | H | H |
| I.a.68 | 2,4,6-trichloropyrid-3-yl | F | H |
| I.a.69 | 2,4,6-trichloropyrid-3-yl | F | F |
| I.a.70 | 2,4,6-trimethylpyrid-3-yl | H | H |
| I.a.71 | 2,4,6-trimethylpyrid-3-yl | F | H |
| I.a.72 | 2,4,6-trimethylpyrid-3-yl | F | F |
| I.a.73 | 2-fluoro-4,6-dimethylpyrid-3-yl | H | H |
| I.a.74 | 2-fluoro-4,6-dimethylpyrid-3-yl | F | H |
| I.a.75 | 2-fluoro-4,6-dimethylpyrid-3-yl | F | F |
| I.a.76 | 2-chloro-4,6-dimethylpyrid-3-yl | H | H |
| I.a.77 | 2-chloro-4,6-dimethylpyrid-3-yl | F | H |
| I.a.78 | 2-chloro-4,6-dimethylpyrid-3-yl | F | F |
| I.a.79 | 5-chloro-2,3-dimethylpyrid-4-yl | H | H |
| I.a.80 | 5-chloro-2,3-dimethylpyrid-4-yl | F | H |
| I.a.81 | 5-chloro-2,3-dimethylpyrid-4-yl | F | F |
| I.a.82 | 3,5-dichloro-2-methylpyrid-4-yl | H | H |
| I.a.83 | 3,5-dichloro-2-methylpyrid-4-yl | F | H |
| I.a.84 | 3,5-dichloro-2-methylpyrid-4-yl | F | F |
| I.a.85 | 2-bromo-4,6-dimethylpyrid-3-yl | H | H |
| I.a.86 | 2-bromo-4,6-dimethylpyrid-3-yl | F | H |
| I.a.87 | 2-bromo-4,6-dimethylpyrid-3-yl | F | F |
| I.a.88 | 4-chloropyrimidin-5-yl | H | H |
| I.a.89 | 4-chloropyrimidin-5-yl | F | H |
| I.a.90 | 4-chloropyrimidin-5-yl | F | F |
| I.a.91 | 4,6-dichloropyrimidin-5-yl | H | H |
| I.a.92 | 4,6-dichloropyrimidin-5-yl | F | H |
| I.a.93 | 4,6-dichloropyrimidin-5-yl | F | F |
| I.a.94 | 4-methylpyrimidin-5-yl | H | H |
| I.a.95 | 4-methylpyrimidin-5-yl | F | H |
| I.a.96 | 4-methylpyrimidin-5-yl | F | F |
| I.a.97 | 4,6-dimethylpyrimidin-5-yl | H | H |
| I.a.98 | 4,6-dimethylpyrimidin-5-yl | F | H |
| I.a.99 | 4,6-dimethylpyrimidin-5-yl | F | F |
| I.a.100 | 2-chloropyrazin-3-yl | H | H |
| I.a.101 | 2-chloropyrazin-3-yl | F | H |
| I.a.102 | 2-chloropyrazin-3-yl | F | F |
| I.a.103 | 2-methylpyrazin-3-yl | H | H |
| I.a.104 | 2-methylpyrazin-3-yl | F | H |
| I.a.105 | 2-methylpyrazin-3-yl | F | F |
| I.a.106 | 3-chloropyridazin-4-yl | H | H |
| I.a.107 | 3-chloropyridazin-4-yl | F | H |
| I.a.108 | 3-chloropyridazin-4-yl | F | F |
| I.a.109 | 3-methylpyridazin-4-yl | H | H |
| I.a.110 | 3-methylpyridazin-4-yl | F | H |
| I.a.111 | 3-methylpyridazin-4-yl | F | F |
| I.a.112 | 2-chlorofuryl-3-yl | H | H |
| I.a.113 | 2-chlorofuryl-3-yl | F | H |
| I.a.114 | 2-chlorofuryl-3-yl | F | F |
| I.a.115 | 2-methylfuryl-3-yl | H | H |
| I.a.116 | 2-methylfuryl-3-yl | F | H |
| I.a.117 | 2-methylfuryl-3-yl | F | F |
| I.a.118 | 2,5-dichlorofuryl-3-yl | H | H |
| I.a.119 | 2,5-dichlorofuryl-3-yl | F | H |
| I.a.120 | 2,5-dichlorofuryl-3-yl | F | F |
| I.a.121 | 2-chloro-4-methylfuryl-3-yl | H | H |
| I.a.122 | 2-chloro-4-methylfuryl-3-yl | F | H |
| I.a.123 | 2-chloro-4-methylfuryl-3-yl | F | F |
| I.a.124 | 2-chloro-4,5-dimethylfuryl-3-yl | H | H |
| I.a.125 | 2-chloro-4,5-dimethylfuryl-3-yl | F | H |
| I.a.126 | 2-chloro-4,5-dimethylfuryl-3-yl | F | F |
| I.a.127 | 1,5-dimethylimidazol-4-yl | H | H |
| I.a.128 | 1,5-dimethylimidazol-4-yl | F | H |
| I.a.129 | 1,5-dimethylimidazol-4-yl | F | F |
| I.a.130 | 1-methyl-5-chloroimidazol-4-yl | H | H |
| I.a.131 | 1-methyl-5-chloroimidazol-4-yl | F | H |
| I.a.132 | 1-methyl-5-chloroimidazol-4-yl | F | F |
| I.a.133 | 1,2,5-trimethylimidazol-4-yl | H | H |
| I.a.134 | 1,2,5-trimethylimidazol-4-yl | F | H |
| I.a.135 | 1,2,5-trimethylixnidazol-4-yl | F | F |
| I.a.136 | 1-methyl-2,5-dichloroimidazol-4-yl | H | H |
| I.a.137 | 1-methyl-2,5-dichloroimidazol-4-yl | F | H |
| I.a.138 | 1-methyl-2,5-dichloroimidazol-4-yl | F | F |
| I.a.139 | 5-chlorooxazol-4-yl | H | H |
| I.a.140 | 5-chlorooxazol-4-yl | F | H |
| I.a.141 | 5-chlorooxazol-4-yl | F | F |
| I.a.142 | 5-methyloxazol-4-yl | H | H |
| I.a.143 | 5-methyloxazol-4-yl | F | H |

TABLE 1-continued

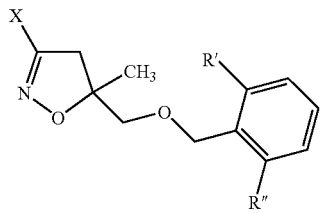

I.a

| No. | X | R' | R" |
|---|---|---|---|
| I.a.144 | 5-methyloxazol-4-yl | F | F |
| I.a.145 | 5-chloroisoxazol-4-yl | H | H |
| I.a.146 | 5-chloroisoxazol-4-yl | F | H |
| I.a.147 | 5-chloroisoxazol-4-yl | F | F |
| I.a.148 | 5-methylisoxazol-4-yl | H | H |
| I.a.149 | 5-methylisoxazol-4-yl | F | H |
| I.a.150 | 5-methylisoxazol-4-yl | F | F |
| I.a.151 | 5-chlorothiazol-4-yl | H | H |
| I.a.152 | 5-chlorothiazol-4-yl | F | H |
| I.a.153 | 5-chlorothiazol-4-yl | F | F |
| I.a.154 | 5-methylthiazol-4-yl | H | H |
| I.a.155 | 5-methylthiazol-4-yl | F | H |
| I.a.156 | 5-methylthiazol-4-yl | F | F |
| I.a.157 | 5-chloroisothiazol-4-yl | H | H |
| I.a.158 | 5-chloroisothiazol-4-yl | F | H |
| I.a.159 | 5-chloroisothiazol-4-yl | F | F |
| I.a.160 | 5-methylisothiazol-4-yl | H | H |
| I.a.161 | 5-methylisothiazol-4-yl | F | H |
| I.a.162 | 5-methylisothiazol-4-yl | F | F |
| I.a.163 | 1,5-dimethyl-1,2,3-triazol-4-yl | H | H |
| I.a.164 | 1,5-dimethyl-1,2,3-triazol-4-yl | F | H |
| I.a.165 | 1,5-dimethyl-1,2,3-triazol-4-yl | F | F |
| I.a.166 | 1-methyl-4-chloro-1,2,3-triazol-5-yl | H | H |
| I.a.167 | 1-methyl-4-chloro-1,2,3-triazol-5-yl | F | H |
| I.a.168 | 1-methyl-4-chloro-1,2,3-triazol-5-yl | F | F |
| I.a.169 | 1-methyl-5-chloro-1,2,3-triazol-4-yl | H | H |
| I.a.170 | 1-methyl-5-chloro-1,2,3-triazol-4-yl | F | H |
| I.a.171 | 1-methyl-5-chloro-1,2,3-triazol-4-yl | F | F |
| I.a.172 | 3-chloro-1,2,5-oxadiazol-4-yl | H | H |
| I.a.173 | 3-chloro-1,2,5-oxadiazol-4-yl | F | H |
| I.a.174 | 3-chloro-1,2,5-oxadiazol-4-yl | F | F |
| I.a.175 | 3-methyl-1,2,5-oxadiazol-4-yl | H | H |
| I.a.176 | 3-methyl-1,2,5-oxadiazol-4-yl | F | H |
| I.a.177 | 3-methyl-1,2,5-oxadiazol-4-yl | F | F |
| I.a.178 | 3-chloro-1,2,4-oxadiazol-5-yl | H | H |
| I.a.179 | 3-chloro-1,2,4-oxadiazol-5-yl | F | H |
| I.a.180 | 3-chloro-1,2,4-oxadiazol-5-yl | F | F |
| I.a.181 | 5-chloro-1,2,4-oxadiazol-3-yl | H | H |
| I.a.182 | 5-chloro-1,2,4-oxadiazol-3-yl | F | H |
| I.a.183 | 5-chloro-1,2,4-oxadiazol-3-yl | F | F |
| I.a.184 | 3-methyl-1,2,4-oxadiazol-5-yl | H | H |
| I.a.185 | 3-methyl-1,2,4-oxadiazol-5-yl | F | H |
| I.a.186 | 3-methyl-1,2,4-oxadiazol-5-yl | F | F |
| I.a.187 | 5-methyl-1,2,4-oxadiazol-3-yl | H | H |
| I.a.188 | 5-methyl-1,2,4-oxadiazol-3-yl | F | H |
| I.a.189 | 5-methyl-1,2,4-oxadiazol-3-yl | F | F |
| I.a.190 | 5-chloro-1,3,4-oxadiazol-2-yl | H | H |
| I.a.191 | 5-chloro-1,3,4-oxadiazol-2-yl | F | H |
| I.a.192 | 5-chloro-1,3,4-oxadiazol-2-yl | F | F |
| I.a.193 | 5-chloro-1,2,3-thiadiazol-4-yl | H | H |
| I.a.194 | 5-chloro-1,2,3-thiadiazol-4-yl | F | H |
| I.a.195 | 5-chloro-1,2,3-thiadiazol-4-yl | F | F |
| I.a.196 | 5-methyl-1,2,3-thiadiazol-4-yl | H | H |
| I.a.197 | 5-methyl-1,2,3-thiadiazol-4-yl | F | H |
| I.a.198 | 5-methyl-1,2,3-thiadiazol-4-yl | F | F |
| I.a.199 | 4-cyanopyrid-3-yl | F | F |
| I.a.200 | 4-cyanopyrid-3-yl | H | H |
| I.a.201 | 4-cyanopyrid-3-yl | F | F |
| I.a.202 | 4-trifluoromethylpyrid-3-yl | F | F |
| I.a.203 | 4-trifluoromethylpyrid-3-yl | H | H |
| I.a.204 | 4-trifluoromethylpyrid-3-yl | F | H |
| I.a.205 | 4-methoxypyrid-3-yl | F | F |
| I.a.206 | 4-methoxypyrid-3-yl | H | H |
| I.a.207 | 4-methoxypyrid-3-yl | F | H |
| I.a.208 | 2-fluoropyrid-3-yl | F | F |

TABLE 1-continued

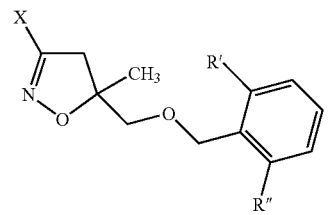

I.a

| No. | X | R' | R" |
|---|---|---|---|
| I.a.209 | 2-fluoropyrid-3-yl | H | H |
| I.a.210 | 2-fluoropyrid-3-yl | F | H |
| I.a.211 | 2-chloropyrid-3-yl | F | F |
| I.a.212 | 2-chloropyrid-3-yl | H | H |
| I.a.213 | 2-chloropyrid-3-yl | F | H |
| I.a.214 | 2-bromopyrid-3-yl | F | F |
| I.a.215 | 2-bromopyrid-3-yl | H | H |
| I.a.216 | 2-bromopyrid-3-yl | F | H |
| I.a.217 | 2-cyanopyrid-3-yl | F | F |
| I.a.218 | 2-cyanopyrid-3-yl | H | H |
| I.a.219 | 2-cyanopyrid-3-yl | F | H |
| I.a.220 | 2-fluoropyrazin-3-yl | F | F |
| I.a.221 | 2-fluoropyrazin-3-yl | H | H |
| I.a.222 | 2-fluoropyrazin-3-yl | F | H |
| I.a.223 | 2-bromopyrazin-3-yl | F | F |
| I.a.224 | 2-bromopyrazin-3-yl | H | H |
| I.a.225 | 2-bromopyrazin-3-yl | F | H |
| I.a.226 | 2-cyanopyrazin-3-yl | F | F |
| I.a.227 | 2-cyanopyrazin-3-yl | H | H |
| I.a.228 | 2-cyanopyrazin-3-yl | F | H |
| I.a.229 | 2-trifluoromethylpyrazin-3-yl | F | F |
| I.a.230 | 2-trifluoromethylpyrazin-3-yl | H | H |
| I.a.231 | 2-trifluoromethylpyrazin-3-yl | F | H |
| I.a.232 | 2-methoxypyrazin-3-yl | F | F |
| I.a.233 | 2-methoxypyrazin-3-yl | H | H |
| I.a.234 | 2-methoxypyrazin-3-yl | F | H |

Likewise most preferred are the compounds of the formula I.b, in particular the compounds of the formulae I.b.1 to I.b.234 which differ from the corresponding compounds of the formulae I.a.1 to I.a.234 in that $R^3$ is hydrogen.

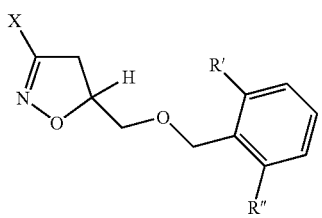

I.b

Likewise most preferred are the compounds of the formula I.c, in particular the compounds of the formulae I.c.1 to I.c.234 which differ from the corresponding compounds of the formulae I.a.1 to I.a.234 in that $R^3$ is ethyl.

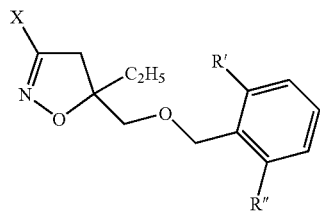

Likewise most preferred are the compounds of the formula I.d, in particular the compounds of the formulae I.d.1 to I.d.234 which differ from the corresponding compounds of the formulae I.a.1 to I.a.234 in that Y is correspondingly substituted naphth-2-yl.

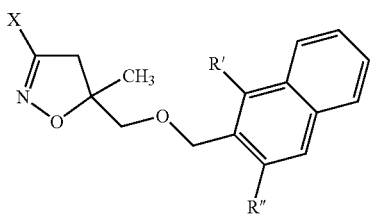

Likewise most preferred are the compounds of the formula I.e, in particular the compounds of the formulae I.e.1 to I.e.234 which differ from the corresponding compounds of the formulae I.a.1 to I.a.234 in that $R^3$ is hydrogen and Y is correspondingly substituted naphth-2-yl.

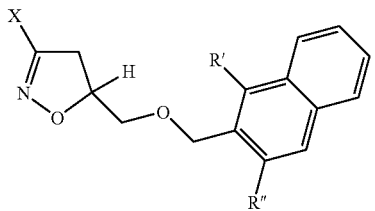

Likewise most preferred are the compounds of the formula I.f (corresponding to formula I where X=4-fluoropyrid-3-yl and $R^1$, $R^2$, $R^4$-$R^7$=hydrogen), in particular the compounds of the formulae I.f.1 to I.f.228 of table 1A, where the definitions of the variables $R^1$ to $R^7$, X and Y are of particular importance for the compounds according to the invention not only in combination with one another but in each case also on their own.

TABLE 1A

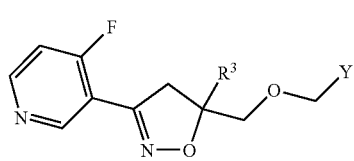

| No. | $R^3$ | Y |
|---|---|---|
| I.f.1 | H | 3-fluorophenyl |
| I.f.2 | CH$_3$ | 3-fluorophenyl |

TABLE 1A-continued

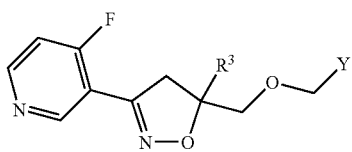

| No. | $R^3$ | Y |
|---|---|---|
| I.f.3 | C$_2$H$_5$ | 3-fluorophenyl |
| I.f.4 | H | 4-fluorophenyl |
| I.f.5 | CH$_3$ | 4-fluorophenyl |
| I.f.6 | C$_2$H$_5$ | 4-fluorophenyl |
| I.f.7 | H | 2-chlorophenyl |
| I.f.8 | CH$_3$ | 2-chlorophenyl |
| I.f.9 | C$_2$H$_5$ | 2-chlorophenyl |
| I.f.10 | H | 3-chlorophenyl |
| I.f.11 | CH$_3$ | 3-chlorophenyl |
| I.f.12 | C$_2$H$_5$ | 3-chlorophenyl |
| I.f.13 | H | 4-chlorophenyl |
| I.f.14 | CH$_3$ | 4-chlorophenyl |
| I.f.15 | C$_2$H$_5$ | 4-chlorophenyl |
| I.f.16 | H | 2-bromophenyl |
| I.f.17 | CH$_3$ | 2-bromophenyl |
| I.f.18 | C$_2$H$_5$ | 2-bromophenyl |
| I.f.19 | H | 3-bromophenyl |
| I.f.20 | CH$_3$ | 3-bromophenyl |
| I.f.21 | C$_2$H$_5$ | 3-bromophenyl |
| I.f.22 | H | 4-bromophenyl |
| I.f.23 | CH$_3$ | 4-bromophenyl |
| I.f.24 | C$_2$H$_5$ | 4-bromophenyl |
| I.f.25 | H | 2-iodophenyl |
| I.f.26 | CH$_3$ | 2-iodophenyl |
| I.f.27 | C$_2$H$_5$ | 2-iodophenyl |
| I.f.28 | H | 2,4-difluorophenyl |
| I.f.29 | CH$_3$ | 2,4-difluoropheny) |
| I.f.30 | C$_2$H$_5$ | 2,4-difluorophenyl |
| I.f.31 | H | 3,5-difluorophenyl |
| I.f.32 | CH$_3$ | 3,5-difluorophenyl |
| I.f.33 | C$_2$H$_5$ | 3,5-difluorophenyl |
| I.f.34 | H | 2,6-dichlorophenyl |
| I.f.35 | CH$_3$ | 2,6-dichlorophenyl |
| I.f.36 | C$_2$H$_5$ | 2,6-dichlorophenyl |
| I.f.37 | H | 2,4-dichlorophenyl |
| I.f.38 | CH$_3$ | 2,4-dichlorophenyl |
| I.f.39 | C$_2$H$_5$ | 2,4-dichlorophenyl |
| I.f.40 | H | 3,4-dichlorophenyl |
| I.f.41 | CH$_3$ | 3,4-dichlorophenyl |
| I.f.42 | C$_2$H$_5$ | 3,4-dichlorophenyl |
| I.f.43 | H | 2,4,6-trichlorophenyl |
| I.f.44 | CH$_3$ | 2,4,6-trichlorophenyl |
| I.f.45 | C$_2$H$_5$ | 2,4,6-trichlorophenyl |
| I.f.46 | H | 2,3,5-trichlorophenyl |
| I.f.47 | CH$_3$ | 2,3,5-trichlorophenyl |
| I.f.48 | C$_2$H$_5$ | 2,3,5-trichlorophenyl |
| I.f.49 | H | 2,3,4,5,6-pentafluorophenyl |
| I.f.50 | CH$_3$ | 2,3,4,5,6-pentafluorophenyl |
| I.f.51 | C$_2$H$_5$ | 2,3,4,5,6-pentafluorophenyl |
| I.f.52 | H | 2-nitrophenyl |
| I.f.53 | CH$_3$ | 2-nitrophenyl |
| I.f.54 | C$_2$H$_5$ | 2-nitrophenyl |
| I.f.55 | H | 3-nitrophenyl |
| I.f.56 | CH$_3$ | 3-nitrophenyl |
| I.f.57 | C$_2$H$_5$ | 3-nitrophenyl |
| I.f.58 | H | 4-nitrophenyl |
| I.f.59 | CH$_3$ | 4-nitrophenyl |
| I.f.60 | C$_2$H$_5$ | 4-nitrophenyl |
| I.f.61 | H | 2-cyanophenyl |
| I.f.62 | CH$_3$ | 2-cyanophenyl |
| I.f.63 | C$_2$H$_5$ | 2-cyanophenyl |
| I.f.64 | H | 3-cyanophenyl |
| I.f.65 | CH$_3$ | 3-cyanophenyl |
| I.f.66 | C$_2$H$_5$ | 3-cyanophenyl |
| I.f.67 | H | 4-cyanophenyl |
| I.f.68 | CH$_3$ | 4-cyanophenyl |
| I.f.69 | C$_2$H$_5$ | 4-cyanophenyl |
| I.f.70 | H | 2-methylphenyl |

TABLE 1A-continued

I.f

[Structure: 4-fluoropyridin-3-yl attached to isoxazoline with R³ and CH₂OCH₂-Y substituents]

| No. | R³ | Y |
|---|---|---|
| I.f.71 | CH₃ | 2-methylphenyl |
| I.f.72 | C₂H₅ | 2-methylphenyl |
| I.f.73 | H | 3-methylphenyl |
| I.f.74 | CH₃ | 3-methylphenyl |
| I.f.75 | C₂H₅ | 3-methylphenyl |
| I.f.76 | H | 4-methylphenyl |
| I.f.77 | CH₃ | 4-methylphenyl |
| I.f.78 | C₂H₅ | 4-methylphenyl |
| I.f.79 | H | 4-ethylphenyl |
| I.f.80 | CH₃ | 4-ethylphenyl |
| I.f.81 | C₂H₅ | 4-ethylphenyl |
| I.f.82 | H | 2,5-dimethylphenyl |
| I.f.83 | CH₃ | 2,5-dimethylphenyl |
| I.f.84 | C₂H₅ | 2,5-dimethylphenyl |
| I.f.85 | H | 3,4-dimethylphenyl |
| I.f.86 | CH₃ | 3,4-dimethylphenyl |
| I.f.87 | C₂H₅ | 3,4-dimethylphenyl |
| I.f.88 | H | 2,4-dimethylphenyl |
| I.f.89 | CH₃ | 2,4-dimethylphenyl |
| I.f.90 | C₂H₅ | 2,4-dimethylphenyl |
| I.f.91 | H | 2,4,6-trimethylphenyl |
| I.f.92 | CH₃ | 2,4,6-trimethylphenyl |
| I.f.93 | C₂H₅ | 2,4,6-trimethylphenyl |
| I.f.94 | H | 2-trifluoromethylphenyl |
| I.f.95 | CH₃ | 2-trifluoromethylphenyl |
| I.f.96 | C₂H₅ | 2-trifluoromethylphenyl |
| I.f.97 | H | 3-trifluoromethylphenyl |
| I.f.98 | CH₃ | 3-trifluoromethylphenyl |
| I.f.99 | C₂H₅ | 3-trifluoromethylphenyl |
| I.f.100 | H | 4-trifluoromethylphenyl |
| I.f.101 | CH₃ | 4-trifluoromethylphenyl |
| I.f.102 | C₂H₅ | 4-trifluoromethylphenyl |
| I.f.103 | H | 2-methoxyphenyl |
| I.f.104 | CH₃ | 2-methoxyphenyl |
| I.f.105 | C₂H₅ | 2-methoxyphenyl |
| I.f.106 | H | 3-methoxyphenyl |
| I.f.107 | CH₃ | 3-methoxyphenyl |
| I.f.108 | C₂H₅ | 3-methoxyphenyl |
| I.f.109 | H | 4-methoxyphenyl |
| I.f.110 | CH₃ | 4-methoxyphenyl |
| I.f.111 | C₂H₅ | 4-methoxyphenyl |
| I.f.112 | H | 3,4,5-trimethoxyphenyl |
| I.f.113 | CH₃ | 3,4,5-trimethoxyphenyl |
| I.f.114 | C₂H₅ | 3,4,5-trimethoxyphenyl |
| I.f.115 | H | 3-trifluoromethoxyphenyl |
| I.f.116 | CH₃ | 3-trifluoromethoxyphenyl |
| I.f.117 | C₂H₅ | 3-trifluoromethoxyphenyl |
| I.f.118 | H | 2-difluoromethoxyphenyl |
| I.f.119 | CH₃ | 2-difluoromethoxyphenyl |
| I.f.120 | C₂H₅ | 2-difluoromethoxyphenyl |
| I.f.121 | H | 2-(ethoxycarbonylmethoxy)phenyl |
| I.f.122 | CH₃ | 2-(ethoxycarbonylmethoxy)phenyl |
| I.f.123 | C₂H₅ | 2-(ethoxycarbonylmethoxy)phenyl |
| I.f.124 | H | 4-(phenyl)phenyl |
| I.f.125 | CH₃ | 4-(phenyl)phenyl |
| I.f.126 | C₂H₅ | 4-(phenyl)phenyl |
| I.f.127 | H | 3-phenoxyphenyl |
| I.f.128 | CH₃ | 3-phenoxyphenyl |
| I.f.129 | C₂H₅ | 3-phenoxyphenyl |
| I.f.130 | H | 2-methyl-3-(phenyl)phenyl |
| I.f.131 | CH₃ | 2-methyl-3-(phenyl)phenyl |
| I.f.132 | C₂H₅ | 2-methyl-3-(phenyl)phenyl |
| I.f.133 | H | 3-phenoxyphenyl |
| I.f.134 | CH₃ | 3-phenoxyphenyl |
| I.f.135 | C₂H₅ | 3-phenoxyphenyl |
| I.f.136 | H | 3-(phenylcarbonyl)phenyl |
| I.f.137 | CH₃ | 3-(phenylcarbonyl)phenyl |
| I.f.138 | C₂H₅ | 3-(phenylcarbonyl)phenyl |
| I.f.139 | H | 4-(methoxycarbonyl)phenyl |
| I.f.140 | CH₃ | 4-(methoxycarbonyl)phenyl |
| I.f.141 | C₂H₅ | 4-(methoxycarbonyl)phenyl |
| I.f.142 | H | 4-(isopropoxycarbonyl)phenyl |
| I.f.143 | CH₃ | 4-(isopropoxycarbonyl)phenyl |
| I.f.144 | C₂H₅ | 4-(isopropoxycarbonyl)phenyl |
| I.f.145 | H | 2-chloro-6-nitrophenyl |
| I.f.146 | CH₃ | 2-chloro-6-nitrophenyl |
| I.f.147 | C₂H₅ | 2-chloro-6-nitrophenyl |
| I.f.148 | H | 3-chloro-4-methoxyphenyl |
| I.f.149 | CH₃ | 3-chloro-4-methoxyphenyl |
| I.f.150 | C₂H₅ | 3-chloro-4-methoxyphenyl |
| I.f.151 | H | 3-chloro-4-ethoxyphenyl |
| I.f.152 | CH₃ | 3-chloro-4-ethoxyphenyl |
| I.f.153 | C₂H₅ | 3-chloro-4-ethoxyphenyl |
| I.f.154 | H | 2-ethyl-5-nitrophenyl |
| I.f.155 | CH₃ | 2-ethyl-5-nitrophenyl |
| I.f.156 | C₂H₅ | 2-ethyl-5-nitrophenyl |
| I.f.157 | H | 2,3-dichloro-4-methoxyphenyl |
| I.f.158 | CH₃ | 2,3-dichloro-4-methoxyphenyl |
| I.f.159 | C₂H₅ | 2,3-dichloro-4-methoxyphenyl |
| I.f.160 | H | 2,3-dichloro-4-isopropoxyphenyl |
| I.f.161 | CH₃ | 2,3-dichloro-4-isopropoxyphenyl |
| I.f.162 | C₂H₅ | 2,3-dichloro-4-isopropoxyphenyl |
| I.f.163 | H | 2,4-dichloro-6-nitrophenyl |
| I.f.164 | CH₃ | 2,4-dichloro-6-nitrophenyl |
| I.f.165 | C₂H₅ | 2,4-dichloro-6-nitrophenyl |
| I.f.166 | H | 2-chloro-3-methyl-4-(methyl-sulfonyl)phenyl |
| I.f.167 | CH₃ | 2-chloro-3-methyl-4-(methyl-sulfonyl)phenyl |
| I.f.168 | C₂H₅ | 2-chloro-3-methyl-4-(methyl-sulfonyl)phenyl |
| I.f.169 | H | benzo[1,4]dioxan-6-yl |
| I.f.170 | CH₃ | benzo[1,4]dioxan-6-yl |
| I.f.171 | C₂H₅ | benzo[1,4]dioxan-6-yl |
| I.f.172 | H | benzo[1,3]dioxolan-5-yl |
| I.f.173 | CH₃ | benzo[1,3]dioxolan-5-yl |
| I.f.174 | C₂H₅ | benzo[1,3]dioxolan-5-yl |
| I.f.175 | H | 2,3-dihydrobenzofuran-2-yl |
| I.f.176 | CH₃ | 2,3-dihydrobenzofuran-2-yl |
| I.f.177 | C₂H₅ | 2,3-dihydrobenzofuran-2-yl |
| I.f.178 | H | benzimidazol-2-yl |
| I.f.179 | CH₃ | benzimidazol-2-yl |
| I.f.180 | C₂H₅ | benzimidazol-2-yl |
| I.f.181 | H | naphth-1-yl |
| I.f.182 | CH₃ | naphth-1-yl |
| I.f.183 | C₂H₅ | naphth-1-yl |
| I.f.184 | H | 2-methylnaphth-1-yl |
| I.f.185 | CH₃ | 2-methylnaphth-1-yl |
| I.f.186 | C₂H₅ | 2-methylnaphth-1-yl |
| I.f.187 | H | anthrancen-9-yl |
| I.f.188 | CH₃ | anthrancen-9-yl |
| I.f.189 | C₂H₅ | anthrancen-9-yl |
| I.f.190 | H | 5-chloro-1-methylpyrazol-4-yl |
| I.f.191 | CH₃ | 5-chloro-1-methylpyrazol-4-yl |
| I.f.192 | C₂H₅ | 5-chloro-1-methylpyrazol-4-yl |
| I.f.193 | H | 5-chloro-1-methyl-3-trifluoro-methylpyrazol-4-yl |
| I.f.194 | CH₃ | 5-chloro-1-methyl-3-trifluoro-methylpyrazol-4-yl |
| I.f.195 | C₂H₅ | 5-chloro-1-methyl-3-trifluoro-methylpyrazol-4-yl |
| I.f.196 | H | thiazol-4-yl |
| I.f.197 | CH₃ | thiazol-4-yl |
| I.f.198 | C₂H₅ | thiazol-4-yl |
| I.f.199 | H | 2-chlorothiazol-5-yl |
| I.f.200 | CH₃ | 2-chlorothiazol-5-yl |
| I.f.201 | C₂H₅ | 2-chlorothiazol-5-yl |
| I.f.202 | H | 3-ethylisoxazol-5-yl |
| I.f.203 | CH₃ | 3-ethylisoxazol-5-yl |
| I.f.204 | C₂H₅ | 3-ethylisoxazol-5-yl |
| I.f.205 | H | 3-n-propylisoxazol-5-yl |
| I.f.206 | CH₃ | 3-n-propylisoxazol-5-yl |

TABLE 1A-continued

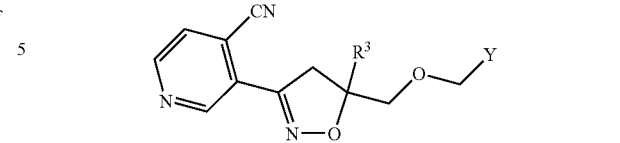

I.f

| No. | R³ | Y |
|---|---|---|
| I.f.207 | C₂H₅ | 3-n-propylisoxazol-5-yl |
| I.f.208 | H | 3-(methoxymethyl)isoxazol-5-yl |
| I.f.209 | CH₃ | 3-(methoxymethyl)isoxazol-5-yl |
| I.f.210 | C₂H₅ | 3-(methoxymethyl)isoxazol-5-yl |
| I.f.211 | H | 5-methoxymethyl-1,3,4-thiadiazol-2-yl |
| I.f.212 | CH₃ | 5-methoxymethyl-1,3,4-thiadiazol-2-yl |
| I.f.213 | C₂H₅ | 5-methoxymethyl-1,3,4-thiadiazol-2-yl |
| I.f.214 | H | pyrid-2-yl |
| I.f.215 | CH₃ | pyrid-2-yl |
| I.f.216 | C₂H₅ | pyrid-2-yl |
| I.f.217 | H | pyrid-3-yl |
| I.f.218 | CH₃ | pyrid-3-yl |
| I.f.219 | C₂H₅ | pyrid-3-yl |
| I.f.220 | H | pyrid-4-yl |
| I.f.221 | CH₃ | pyrid-4-yl |
| I.f.222 | C₂H₅ | pyrid-4-yl |
| I.f.223 | H | 2-chloropyrid-5-yl |
| I.f.224 | CH₃ | 2-chloropyrid-5-yl |
| I.f.225 | C₂H₅ | 2-chloropyrid-5-yl |
| I.f.226 | H | 5-ethyl-3-(ethoxy-carbonyl)pyrid-2-yl |
| I.f.227 | CH₃ | 5-ethyl-3-(ethoxy-carbonyl)pyrid-2-yl |
| I.f.228 | C₂H₅ | 5-ethyl-3-(ethoxy-carbonyl)pyrid-2-yl |

Likewise most preferred are the compounds of the formula I.g, in particular the compounds of the formulae I.g.1 to I.g.228 which differ from the corresponding compounds of the formulae I.f.1 to I.f.228 in that X is 4-chloropyrid-3-yl.

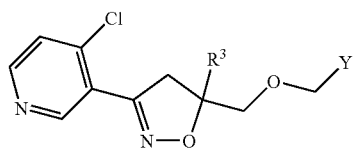

I.g

Likewise most preferred are the compounds of the formula I.h, in particular the compounds of the formulae I.h.1 to I.h.228 which differ from the corresponding compounds of the formulae I.f.1 to I.f.228 in that X is 4-bromopyrid-3-yl.

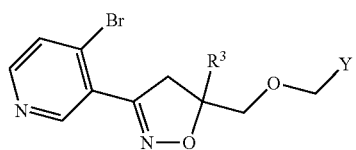

I.h

Likewise most preferred are the compounds of the formula I.i, in particular the compounds of the formulae I.i.1 to I.i.228 which differ from the corresponding compounds of the formulae I.f.1 to I.f.228 in that X is 4-cyanopyrid-3-yl.

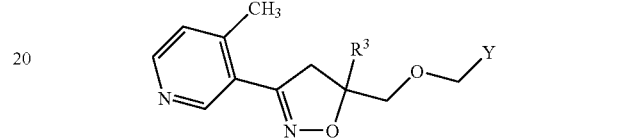

I.i

Likewise most preferred are the compounds of the formula I.k, in particular the compounds of the formulae I.k.1 to I.k.228 which differ from the corresponding compounds of the formulae I.f.1 to I.f.228 in that X is 4-methylpyrid-3-yl.

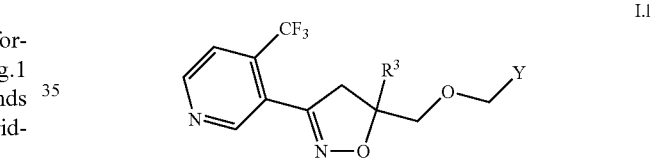

I.k

Likewise most preferred are the compounds of the formula I.l, in particular the compounds of the formulae I.l.1 to I.l.228 which differ from the corresponding compounds of the formulae I.f.1 to I.f.228 in that X is 4-trifluoromethylpyrid-3-yl.

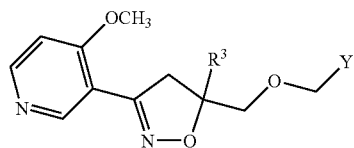

I.l

Likewise most preferred are the compounds of the formula I.m, in particular the compounds of the formulae I.m.1 to I.m.228 which differ from the corresponding compounds of the formulae I.f.1 to I.f.228 in that X is 4-methoxypyrid-3-yl.

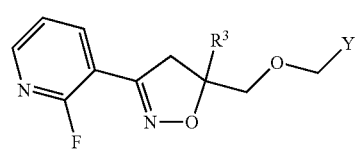

I.m

Likewise most preferred are the compounds of the formula I.n, in particular the compounds of the formulae I.n.1 to I.n.228 which differ from the corresponding compounds of the formulae I.f.1 to I.f.228 in that X is 2-fluoropyrid-3-yl.

I.n

Likewise most preferred are the compounds of the formula I.o, in particular the compounds of the formulae I.o.1 to I.o.228 which differ from the corresponding compounds of the formulae I.f.1 to I.f.228 in that X is 2-chloropyrid-3-yl.

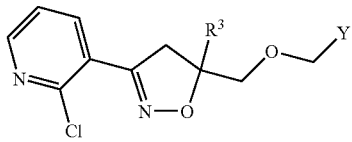
I.o

Likewise most preferred are the compounds of the formula I.p, in particular the compounds of the formulae I.p.1 to I.p.228 which differ from the corresponding compounds of the formulae I.f.1 to I.f.228 in that X is 2-bromopyrid-3-yl.

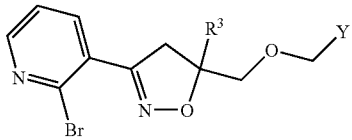
I.p

Likewise most preferred are the compounds of the formula I.q, in particular the compounds of the formulae I.q.1 to I.q.228 which differ from the corresponding compounds of the formulae I.f.1 to I.f.228 in that X is 2-cyanopyrid-3-yl.

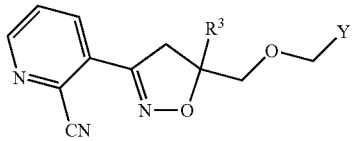
I.q

Likewise most preferred are the compounds of the formula I.r, in particular the compounds of the formulae I.r.1 to I.r.228 which differ from the corresponding compounds of the formulae I.f.1 to I.f.228 in that X is 2-methylpyrid-3-yl.

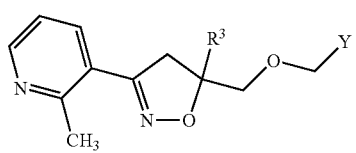
I.r

Likewise most preferred are the compounds of the formula I.s, in particular the compounds of the formulae I.s.1 to I.s.228 which differ from the corresponding compounds of the formulae I.f.1 to I.f.228 in that X is 2-trifluoromethylpyrid-3-yl.

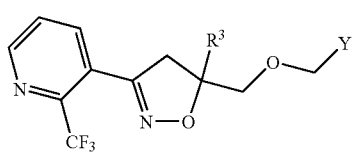
I.s

Likewise most preferred are the compounds of the formula I.t, in particular the compounds of the formulae I.t.1 to I.t.228 which differ from the corresponding compounds of the formulae I.f.1 to I.f.228 in that X is 2-methoxypyrid-3-yl.

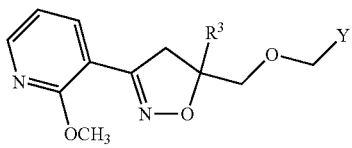
I.t

Likewise most preferred are the compounds of the formula I.u, in particular the compounds of the formulae I.u.1 to I.u.228 which differ from the corresponding compounds of the formulae I.f.1 to I.f.228 in that X is 2,4-dichloropyrid-3-yl.

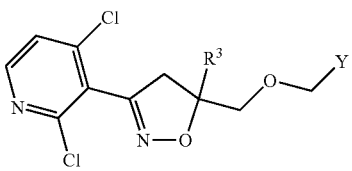
I.u

Likewise most preferred are the compounds of the formula I.v, in particular the compounds of the formulae I.v.1 to I.v.228 which differ from the corresponding compounds of the formulae I.f.1 to I.f.228 in that X is 2,4-dimethylpyrid-3-yl.

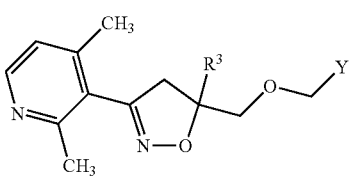
I.v

Likewise most preferred are the compounds of the formula I.w, in particular the compounds of the formulae I.w.1 to I.w.228 which differ from the corresponding compounds of the formulae I.f.1 to I.f.228 in that X is 2,6-difluoropyrid-3-yl.

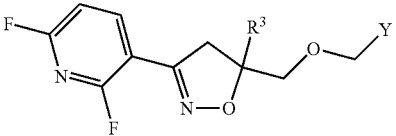
I.w

Likewise most preferred are the compounds of the formula I.x, in particular the compounds of the formulae I.x.1 to I.x.228 which differ from the corresponding compounds of the formulae I.f.1 to I.f.228 in that X is 2,6-dichloropyrid-3-yl.

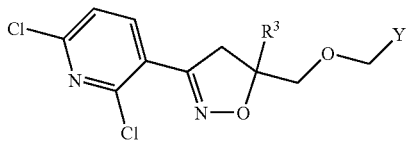

I.x

Likewise most preferred are the compounds of the formula I.y, in particular the compounds of the formulae I.y.1 to I.y.228 which differ from the corresponding compounds of the formulae I.f.1 to I.f.228 in that X is 2,6-dibromopyrid-3-yl.

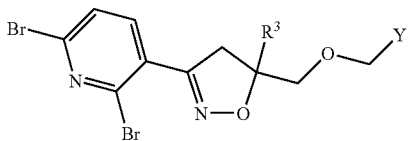

I.y

Likewise most preferred are the compounds of the formula I.z, in particular the compounds of the formulae I.z.1 to I.z.228 which differ from the corresponding compounds of the formulae I.f.1 to I.f.228 in that X is 2,6-dimethylpyrid-3-yl.

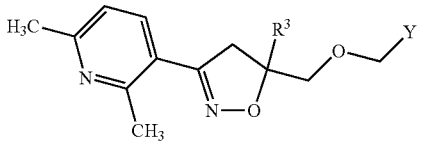

I.z

Likewise most preferred are the compounds of the formula I.aa, in particular the compounds of the formulae I.aa.1 to I.aa.228 which differ from the corresponding compounds of the formulae I.f.1 to I.f.228 in that X is 2-chloro-6-methylpyrid-3-yl.

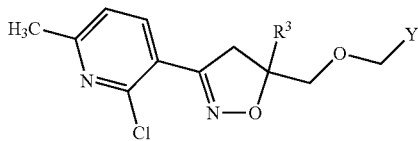

I.aa

Likewise most preferred are the compounds of the formula I.ab, in particular the compounds of the formulae I.ab.1 to I.ab.228 which differ from the corresponding compounds of the formulae I.f.1 to I.f.228 in that X is 6-chloro-2-methylpyrid-3-yl.

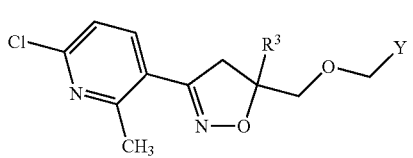

I.ab

Likewise most preferred are the compounds of the formula I.ac, in particular the compounds of the formulae I.ac.1 to I.ac.228 which differ from the corresponding compounds of the formulae I.f.1 to I.f.228 in that X is 2,4,6-trichloropyrid-3-yl.

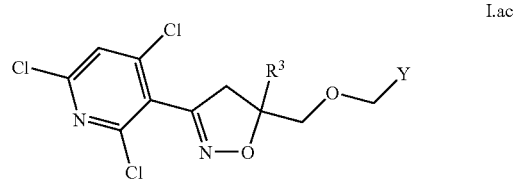

I.ac

Likewise most preferred are the compounds of the formula I.ad, in particular the compounds of the formulae I.ad.1 to I.ad.228 which differ from the corresponding compounds of the formulae I.f.1 to I.f.228 in that X is 2,4-difluoro-6-methylpyrid-3-yl.

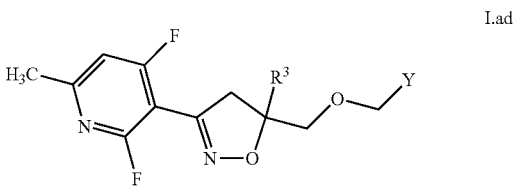

I.ad

Likewise most preferred are the compounds of the formula I.ae, in particular the compounds of the formulae I.ae.1 to I.ae.228 which differ from the corresponding compounds of the formulae I.f.1 to I.f.228 in that X is 2,4,6-trimethylpyrid-3-yl.

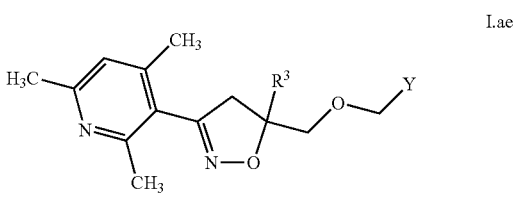

I.ae

Likewise most preferred are the compounds of the formula I.af, in particular the compounds of the formulae I.af.1 to I.af.228 which differ from the corresponding compounds of the formulae I.f.1 to I.f.228 in that X is 4,6-dimethyl-2-fluoropyrid-3-yl.

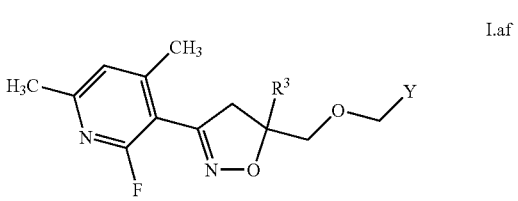

I.af

Likewise most preferred are the compounds of the formula I.ag, in particular the compounds of the formulae I.ag.1 to I.ag.228 which differ from the corresponding compounds of the formulae I.f.1 to I.f.228 in that X is 2-chloro-4,6-dimethylpyrid-3-yl.

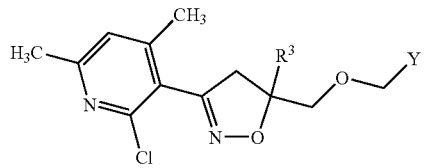

I.ag

Likewise most preferred are the compounds of the formula I.ah, in particular the compounds of the formulae I.ah.1 to I.ah.228 which differ from the corresponding compounds of the formulae I.f.1 to I.f.228 in that X is 2-bromo-4-fluoro-6-methylpyrid-3-yl.

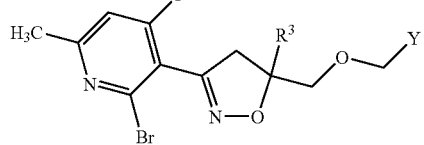

I.ah

Likewise most preferred are the compounds of the formula I.ai, in particular the compounds of the formulae I.ai.1 to I.ai.228 which differ from the corresponding compounds of the formulae I.f.1 to I.f.228 in that X is 3-chloropyrid-2-yl.

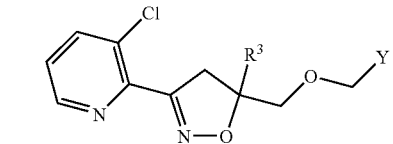

I.ai

Likewise most preferred are the compounds of the formula I.ak, in particular the compounds of the formulae I.ak.1 to I.ak.228 which differ from the corresponding compounds of the formulae I.f.1 to I.f.228 in that X is 3-chloro-6-methylpyrid-2-yl.

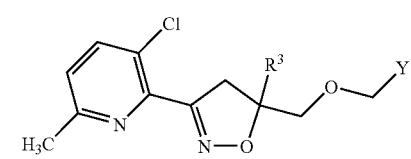

I.ak

Likewise most preferred are the compounds of the formula I.al, in particular the compounds of the formulae I.al.1 to I.al.228 which differ from the corresponding compounds of the formulae I.f.1 to I.f.228 in that X is 3,5-dichloropyrid-4-yl.

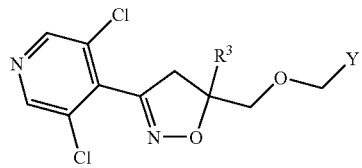

I.al

Likewise most preferred are the compounds of the formula I.am, in particular the compounds of the formulae I.am.1 to I.am.228 which differ from the corresponding compounds of the formulae I.f.1 to I.f.228 in that X is 2,3-dichloropyrid-4-yl.

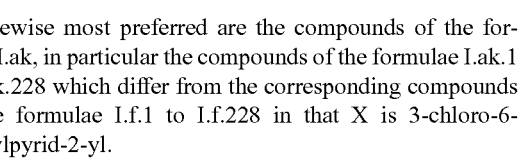

I.am

Likewise most preferred are the compounds of the formula I.am, in particular the compounds of the formulae I.am.1 to I.am.228 which differ from the corresponding compounds of the formulae I.f.1 to I.f.228 in that X is 3-chloro-2-methylpyrid-4-yl.

I.an

Likewise most preferred are the compounds of the formula I.ao, in particular the compounds of the formulae I.ao.1 to I.ao.228 which differ from the corresponding compounds of the formulae I.f.1 to I.f.228 in that X is 3,5-dichloro-2-methylpyrid-4-yl.

I.ao

Likewise most preferred are the compounds of the formula I.ap, in particular the compounds of the formulae I.ap.1 to I.ap.228 which differ from the corresponding compounds of the formulae I.f.1 to I.f.228 in that X is 5-chloro-2,3-dimethylpyrid-4-yl.

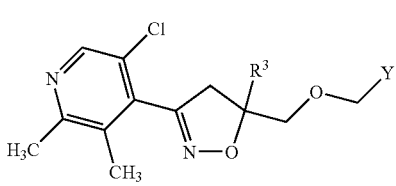
I.ap

Likewise most preferred are the compounds of the formula I.aq, in particular the compounds of the formulae I.aq.1 to I.aq.228 which differ from the corresponding compounds of the formulae I.f.1 to I.f.228 in that X is 2-fluoropyrazin-3-yl.

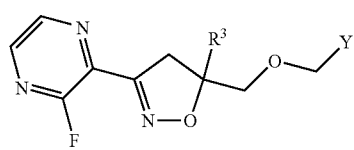
I.aq

Likewise most preferred are the compounds of the formula I.ar, in particular the compounds of the formulae I.ar.1 to I.ar.228 which differ from the corresponding compounds of the formulae I.f.1 to I.f.228 in that X is 2-chloropyrazin-3-yl.

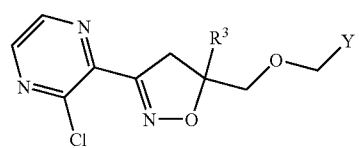
I.ar

Likewise most preferred are the compounds of the formula I.as, in particular the compounds of the formulae I.as.1 to I.as.228 which differ from the corresponding compounds of the formulae I.f.1 to I.f.228 in that X is 2-bromopyrazin-3-yl.

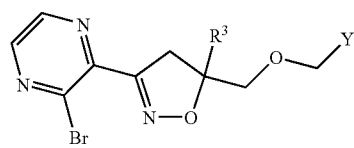
I.as

Likewise most preferred are the compounds of the formula I.at, in particular the compounds of the formulae I.at.1 to I.at.228 which differ from the corresponding compounds of the formulae I.f.1 to I.f.228 in that X is 2-cyanopyrazin-3-yl.

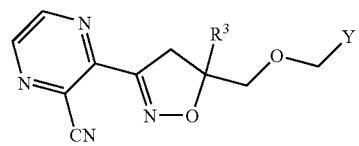
I.at

Likewise most preferred are the compounds of the formula I.au, in particular the compounds of the formulae I.au.1 to I.au.228 which differ from the corresponding compounds of the formulae I.f.1 to I.f.228 in that X is 2-methylpyrazin-3-yl.

I.au

Likewise most preferred are the compounds of the formula I.av, in particular the compounds of the formulae I.av.1 to I.av.228 which differ from the corresponding compounds of the formulae I.f.1 to I.f.228 in that X is 2-trifluoromethylpyrazin-3-yl.

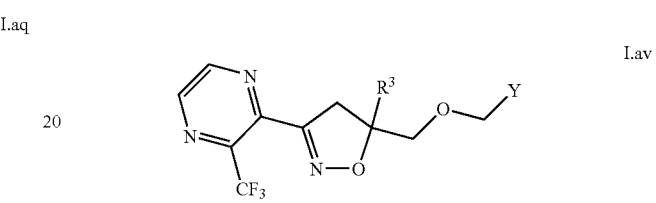
I.av

Likewise most preferred are the compounds of the formula I.aw, in particular the compounds of the formulae I.aw.1 to I.aw.228 which differ from the corresponding compounds of the formulae I.f.1 to I.f.228 in that X is 2-methoxypyrazin-3-yl.

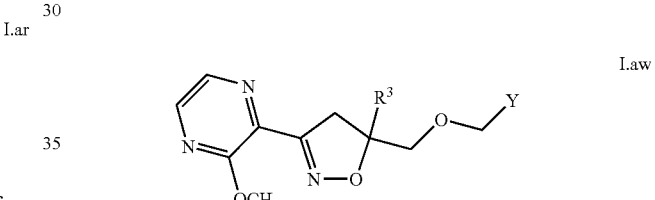
I.aw

The 3-heteroaryl-substituted isoxazolines of the formula I can be obtained by different routes, for example by the following process:

Process A

An aldoxime of the formula VII is, via the corresponding hydroxamic acid halide of the formula VI converted into a nitrile oxide of the formula V. The nitrile oxide of the formula V reacts with an allyl alcohol of the formula IV to give a 5-hydroxymethylisoxazoline of the formula III. This is then etherified with an arylmethyl derivative of the formula II to give the 3-heteroaryl-substituted isoxazoline of the formula I:

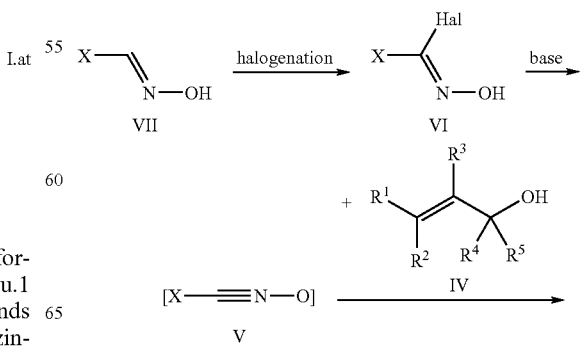

-continued

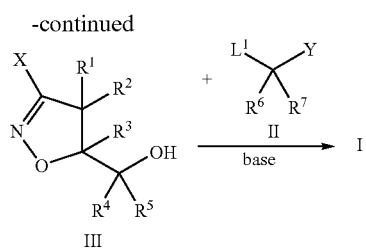

L¹ in formula II is a nucleophilically displaceable leaving group, such as halogen (e.g. chlorine, bromine or iodine), arylsulfonyl, $C_1$-$C_6$-alkylsulfonyl, $C_1$-$C_6$-haloalkylsulfonyl, $C_1$-$C_6$-alkylsulfonyloxy or $C_1$-$C_6$-haloalkylsulfonyloxy, such as, for example, tolylsulfonyl or trifluoromethylsulfonyloxy, or another equivalent leaving group.

Hal in formula VI is halogen, preferably chlorine or bromine, with particular preference bromine.

The reaction of the 5-hydroxymethylisoxazoline of the formula III with an arylmethyl derivative of the formula II in the presence of a base to give the 3-heteroaryl-substituted isoxazoline of the formula I is usually carried out at temperatures of from 0° C. to 120° C., preferably from 10° C. to 80° C., in an inert organic solvent [cf. EP-0 334 120].

Suitable aprotic solvents are ethers, such as diethyl ether, diisopropyl ether, tert-butyl methyl ether, dioxane, anisole and tetrahydrofuran, and also dimethyl sulfoxide, dimethylformamide and dimethylacetamide, particularly preferably diethyl ether, tert-butyl methyl ether, dioxane and tetrahydrofuran.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates such as lithium carbonate, sodium carbonate, potassium carbonate and calcium carbonate, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines.

The bases are generally employed in catalytic amounts; however, they can also be employed in equimolar amounts, in excess or, if appropriate, as solvent.

The starting materials are generally reacted with one another in equimolar amounts. It may be advantageous to employ an excess of II, based on III.

Work-up and isolation of the products can be carried out in a manner known per se.

The arylmethyl derivatives of the formula II required for preparing the 3-heteroaryl-substituted isoxazolines of the formula I are known from the literature [cf. Organikum, 1979, pp. 213f., 413f.], or they can be prepared in accordance with the literature cited.

The nitrile oxides of the formula V required for preparing the 5-hydroxymethylisoxazolines of the formula III can be prepared in accordance with the literature in situ from the corresponding aldoximes of the formula VII via the stage of the hydroxamic acid halide of the formula VI [cf. Houben-Weyl, Methoden der organischen Chemie [Methods of organic chemistry], vol. E 5, 1985, p. 1591 ff. and literature cited therein], or they are known from the literature cited.

In general, the aldoxime of the formula VII is initially charged together with the allyl alcohol of the formula IV; using a halogenating agent, if appropriate with addition of base, the corresponding hydroxamic acid chloride of the formula VI is formed, and this is converted by further addition of base into the nitrile oxide of the formula V. The nitrile oxide of the formula V generated in this way then reacts with the allyl alcohol of the formula IV initially charged with the reaction mixture to give the 5-hydroxymethylisoxazoline of the formula III.

Furthermore, it is also possible to initially halogenate the aldoxime of the formula VIII to give the hydroxamic acid chloride of the formula VI, followed by addition of the allyl alcohol of the formula IV and the base. The nitrile oxide of the formula V generated in this way then reacts with the allyl alcohol of the formula IV, giving the 5-hydroxymethylisoxazoline of the formula III.

The reaction of the nitrile oxide of the formula V with an allyl alcohol of the formula IV is usually carried out at temperatures of from −30° C. to 80° C., preferably from −10° C. to 20° C., in an inert organic solvent [cf. Houben-Weyl, Methoden der organischen Chemie, Vol. E 5, 1985, 1607 ff. and literature cited therein].

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitrites, such as acetonitrile and propionitrile, ketones, such as acetone, methyl ethyl ketone, diethyl ketone and tert-butyl methyl ketone, dimethyl sulfoxide, dimethylformamide and dimethylacetamide.

It is also possible to use mixtures of the solvents mentioned.

The starting materials are generally reacted with one another in equimolar amounts. It may be advantageous to use an excess of IV, based on V.

The reaction mixtures are worked up in a customary manner, for example by mixing with water, separating the phases and, if appropriate, chromatographic purification of the crude products. Some of the intermediates and end products are obtained in the form of viscous oils which can be freed from volatile components or purified under reduced pressure and at moderately elevated temperature. If the intermediates and end products are obtained as solids, purification can also be carried out by recrystallization or digestion.

The corresponding aldoximes of the formula VII are known from the literature [cf. Houben-Weyl, Methoden der organischen Chemie, Vol. 10/4, 1968, p. 55 ff.], or they can be prepared from the corresponding aldehydes, in accordance with the literature cited.

The allyl alcohols of the formula IV required for preparing the 5-hydroxymethylisoxazolines III are known from the literature [cf. EP-514 987; Houben-Weyl, Methoden der organischen Chemie, Vol. 6/1a, 1979, p. 55 ff. and literature cited therein] or they can be prepared in accordance with the literature cited.

Process B

A nitrile oxide of the formula V reacts with an allyl derivative of the formula VIII to give a methyl isoxazoline derivative of the formula IX. This is then etherified with an arylmethyl alcohol of the formula X to give the 3-heteroaryl-substituted isoxazoline of the formula I:

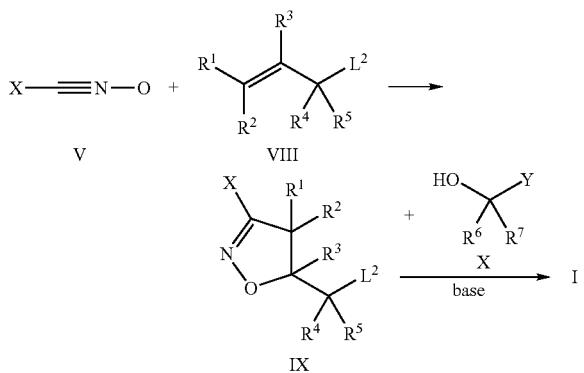

L² in the formulae VIII and IX is a nucleophilically displaceable leaving group, such as halogen (e.g. chlorine, bromine or iodine), $C_1$-$C_6$-alkylsulfonyloxy or $C_1$-$C_6$-haloalkylsulfonyloxy, such as, for example, trifluoromethylsulfonyloxy, or another equivalent leaving group.

The reaction of the methylisozoline derivative of the formula IX with an arylmethyl alcohol of the formula X is carried out analogously to the reaction of the 5-hydroxymethylisoxazoline of the formula III with an arylmethyl derivative of the formula II in process A.

The arylmethyl alcohols of the formula X required for preparing the 3-heteroaryl-substituted isoxazolines of the formula I are known to the person skilled in the art or can be prepared by reactions known from the literature.

The preparation of the methylisoxazoline derivatives of the formula IX from nitrile oxides of the formula V and allyl derivatives of the formula VIII is carried out analogously to the preparation of the 5-hydroxymethylisoxazolines of the formula III in process A.

Furthermore, it is possible to prepare the methylisoxazoline derivatives of the formula IX from 5-hydroxymethylisoxazolines of the formula III:

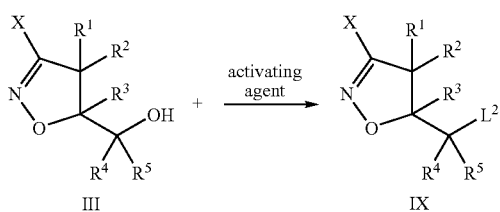

The conversion of the 5-hydroxymethylisoxazolines into methylisoxazoline derivatives of the formula IX is usually carried out at temperatures of from −20° C. to the reflux temperature of the reaction mixtures in question, in an inert solvent.

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran. It is also possible to use mixtures of the solvents mentioned.

Suitable activating agents are, for example, halogenating agents, such as thionyl chloride, phosgene, diphosgene, triphosgene, oxalyl chloride, thionyl bromide, oxalyl bromide, or, for example, alkylsulfonyl chlorides, such as, for example, methylsulfonyl chloride, or haloalkylsulfonyl chlorides, such as, for example, trifluoromethylsulfonyl chloride.

The starting materials are generally reacted with one another in equimolar amounts. It may be advantageous to employ an excess of activating agent.

The allyl derivatives of the formula VIII are known to the person skilled in the art or can be prepared, for example, from the allyl alcohols of the formula IV, analogously to the conversion of III into IX.

Process C

An allyl alcohol of the formula IV is converted with arylmethyl derivative of the formula II into an arylmethyl allyl ether of the formula XI. This then reacts with a nitrile oxide of the formula V to give the 3-heteroaryl-substituted isoxazolines of the formula I:

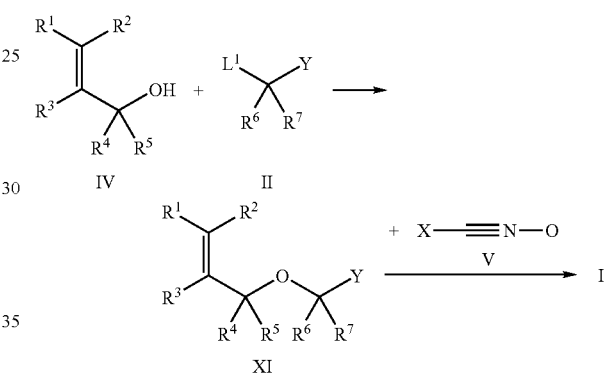

L¹ in formula II is a nucleophilically displaceable leaving group, such as halogen (e.g. chlorine, bromine or iodine), aryl-, $C_1$-$C_6$-alkylsulfonyl, arylsulfonyl, (e.g. toluolsulfonyl), $C_1$-$C_6$-haloalkylsulfonyl, $C_1C_6$-alkylsulfonyloxy or $C_1$-$C_6$-haloalkylsulfonyloxy (such as e.g. trifluoromethylsulfonyloxy), or another equivalent leaving group.

The reaction of the arylmethyl allyl ethers of the formula XI with a nitrile oxide of the formula V to give the 3-heteroaryl-substituted isoxazolines of the formula I is carried out analogously to the reaction of the nitrile oxide of the formula V with an allyl alcohol of the formula IV in process A.

The starting materials are generally reacted with one another in equimolar amounts. It may be advantageous to employ an excess of XI, based on V.

Work-up and isolation of the products can be carried out in a manner known per se.

The nitrile oxides of the formula V required for preparing the 3-heteroaryl-substituted isoxazolines of the formula I are obtainable analogously to process A.

The reaction of the allyl alcohol of the formula IV with an arylmethyl derivative of the formula II is carried out analogously to the reaction of the 5-hydroxymethylisoxazoline of the formula III with an arylmethyl derivative of the formula II in process A.

The starting materials are generally reacted with one another in equimolar amounts. It may be advantageous to employ an excess of II, based on IV.

Work-up and isolation of the products can be carried out in a manner known per se.

The arylmethyl derivatives of the formula II and allyl alcohols of the formula IV required for preparing the allylmethyl allyl ethers of the formula XI can be obtained according to process A.

Furthermore, it is possible to prepare the arylmethyl allyl ether of the formula XI by reacting the corresponding allyl derivative of the formula VIII with an arylmethyl alcohol of the formula X (cf. process B).

The reaction is carried out analogously to the reaction of the allyl alcohol of the formula IV with an arylmethyl derivative of the formula II, or analogously to the reaction of 5-hydroxymethylisoxazoline of the formula III with an arylmethyl derivative of the formula II in process A.

The allyl derivatives of the formula VIII and arylmethyl alcohols of the formula X required can be obtained according to process B.

5-Hydroxymethylisoxazolines of the formula III

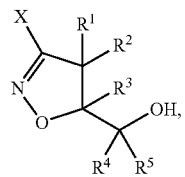

where $X, R^1, R^2, R^3, R^4$ and $R^5$ are as defined in claim 1 also form part of the subject-matter of the present invention.

With respect to the variables, the particularly preferred embodiments of the intermediates correspond to those of the radicals $X, R^1, R^2, R^3, R^4$ and $R^5$ of formula I.

Particular preference is given to 5-hydroxymethylisoxazolines of the formula III, in which X is 6-membered heteroaryl having one to three nitrogen atoms;
  preferably 6-membered heteroaryl having one or two nitrogen atoms;
  in particular pyridyl, pyrimidyl and pyrazinyl;
  very preferably pyridyl and pyrimidyl;
  also preferably pyridyl and pyrazinyl;
  where the 6-membered heteroaryl is substituted in each case as described above; and
$R^1$-$R^5$ are hydrogen, $C_1$-$C_4$-alkyl, such as, for example, methyl or ethyl, or $C_1$-$C_4$-haloalkyl, such as, for example, difluoromethyl, trifluoromethyl or trichloromethyl;
  particularly preferably hydrogen, methyl or trifluoromethyl;
  very preferably hydrogen;
  with particular preference, $R^1$, $R^2$, $R^4$-$R^5$ are hydrogen, methyl or trifluoromethyl and $R^3$ is hydrogen, methyl, ethyl or trifluoromethyl;
  with very particular preference, $R^1$, $R^2$, $R^4$-$R^5$ are hydrogen and $R^3$ is methyl.

Particular preference is also given to 5-hydroxymethylisoxazolines of the formula III in which
X is $X^1$, where
$R^a$ is halogen, cyano, nitro, hydroxyl, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, $C_1$-$C_6$-alkylsulfinyl or $C_1$-$C_6$-alkylsulfonyl,
$R^b$ is hydrogen or one of the substituents mentioned above under $R^a$;

$R^d$ is hydrogen or $C_1$-$C_6$-alkyl;
  preferably hydrogen or $C_1$-$C_4$-alkyl;

with particular preference
$R^a$ is halogen, $C_1$-$C_6$-alkyl, $C_1$-$C_6$-haloalkyl, $C_1$-$C_6$-alkoxy or $C_1$-$C_6$-haloalkoxy;
$R^b$ is hydrogen, halogen, $C_1$-$C_6$-alkyl, $C_1$-$c_6$-haloalkyl, $C_1$-$C_6$-alkoxy or $C_1$-$C_6$-haloalkoxy;
$R^d$ is hydrogen or $C_1$-$C_4$-alkyl; and
$R^1$-$R^7$ are hydrogen, $C_1$-$C_4$-alkyl, such as, for example, methyl or ethyl, or $C_1$-$C_4$-haloalkyl, such as, for example, difluoromethyl, trifluoromethyl or trichloromethyl;
  particularly preferably hydrogen, methyl or trifluoromethyl;
  very preferably hydrogen;
  with particular preference $R^1$, $R^2$, $R^4$-$R^7$ are hydrogen, methyl or trifluoromethyl and $R^3$ is hydrogen, methyl, ethyl or trifluoromethyl;
  with very particular preference, $R^1$, $R^2$, $R^4$-$R^7$ are hydrogen and $R^3$ is methyl.

Particular preference is also given to the 5-hydroxymethylisoxazolines of the formula III, in which
X is $X^5$, where
$R^a$ is halogen, cyano, nitro, hydroxyl, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, $C_1$-$C_6$-alkylsulfinyl or $C_1$-$C_6$-alkylsulfonyl,
$R^b$, $R^c$ are hydrogen or one of the substituents mentioned above under $R^a$; and
$R^d$ is hydrogen or $C_1$-$C_6$-alkyl;
  preferably hydrogen or $C_1$-$C_4$-alkyl;

preferably
$R^a$ is halogen, cyano, nitro, hydroxyl, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, $C_1$-$C_6$-alkylsulfinyl or $C_1$-$C_6$-alkylsulfonyl;
$R^b$, $R^c$ are hydrogen or one of the substituents mentioned above under $R^a$; and
$R^d$ is hydrogen or $C_1$-$C_4$-alkyl;

where the 5-membered heterocycle is attached to the isoxazoline skeleton in the position ortho to the heteroatom;

with particular preference
$R^a$ is halogen, $C_1$-$C_6$-alkyl, $C_1$-$C_6$-haloalkyl, $C_1$-$C_6$-alkoxy or $C_1$-$C_6$-haloalkoxy;
$R^b$, $R^c$ are hydrogen, or one of the substituents mentioned above under $R^a$; and
$R^d$ is hydrogen or $C_1$-$C_4$-alkyl;

where the 5-membered heterocycle is attached to the isoxazoline skeleton in the position ortho to the heteroatom; and
$R^1$-$R^5$ are hydrogen, $C_1$-$C_4$-alkyl, such as, for example, methyl or ethyl, or $C_1$-$C_4$-haloalkyl, such as, for example, difluoromethyl, trifluoromethyl or trichloromethyl;
  particularly preferably hydrogen, methyl or trifluoromethyl;
  very preferably hydrogen;
  with particular preference, $R^1$, $R^2$, $R^4$-$R^5$ are hydrogen, methyl or trifluoromethyl and $R^3$ is hydrogen, methyl, ethyl or trifluoromethyl;
  with very particular preference, $R^1$, $R^2$, $R^4$-$R^5$ are hydrogen and $R^3$ is methyl.

Particular preference is also given to 5-hydroxymethylisoxazolines of the formula III, in which
X is $X^6$, where
$R^a$ is halogen, cyano, nitro, hydroxyl, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, $C_1$-$C_6$-alkylsulfinyl or $C_1$-$C_6$-alkylsulfonyl;

$R^b$ is hydrogen, or one of the substituents mentioned above under $R^a$;

preferably $R^a$ is halogen, cyano, nitro, hydroxyl, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio, $C_1$-$C_6$-alkylsulfinyl or $C_1$-$C_6$-alkylsulfonyl, $R^b$ is hydrogen, or one of the substituents mentioned above under $R^a$;

where the 5-membered heterocycle is attached to the isoxazoline skeleton in the position ortho to a heteroatom;

with particular preference $R^a$ is halogen, $C_1$-$C_6$-alkyl, $C_1$-$C_6$-haloalkyl, $C_1$-$C_6$-alkoxy or $C_1$-$C_6$-haloalkoxy, $R^b$ is hydrogen, or one of the substituents mentioned above under $R^a$;

where the 5-membered heterocycle is attached to the isoxazoline skeleton in the position ortho to a heteroatom; and $R^1$-$R^5$ are hydrogen, $C_1$-$C_4$-alkyl, such as, for example, methyl or ethyl, or $C_1$-$C_4$-haloalkyl, such as, for example, difluoromethyl, trifluoromethyl or trichloromethyl;

particularly preferably hydrogen, methyl or trifluoromethyl;

very preferably hydrogen;

with particular preference, $R^1$, $R^2$, $R^4$-$R^5$ are hydrogen, methyl or trifluoromethyl and $R^3$ is hydrogen, methyl, ethyl or trifluoromethyl;

with very particular preference, $R^1$, $R^2$, $R^4$-$R^5$ are hydrogen and $R^3$ is methyl.

The present invention also provides methylisoxazolines of the formula IX

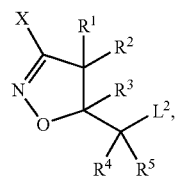

IX where X and $R^1$-$R^5$ are as defined in claim 1 and $L^2$ is a nucleophilically displaceable leaving group, such as halogen (for example chlorine, bromine and iodine), $C_1$-$C_6$-alkylsulfonyloxy or $C_1$-$C_6$-haloalkylsulfonyloxy (for example trifluoromethylsulfonyloxy), or another equivalent leaving group.

With respect to the variables, the particularly preferred embodiments of the intermediates correspond to those of radicals X and $R^1$-$R^5$ of the formula I.

Particular preference is given to methylisoxazolines of the formula IX in which

X is 6-membered heteroaryl having one to three nitrogen atoms;

in particular 6-membered heteroaryl having one or two nitrogen atoms;

very preferably pyridyl;

where the 6-membered heteroaryl is substituted as described above; and $R^1$-$R^5$ are hydrogen, $C_1$-$C_4$-alkyl, such as, for example, methyl or ethyl, or $C_1$-$C_4$-haloalkyl, such as, for example, difluoromethyl, trifluoromethyl or trichloromethyl;

particularly preferably hydrogen, methyl or trifluoromethyl;

very preferably hydrogen;

with particular preference, $R^1$, $R^2$, $R^4$-$R^5$ are hydrogen, methyl or trifluoromethyl and $R^3$ is hydrogen, methyl, ethyl or trifluoromethyl;

with very particular preference, $R^1$, $R^2$, $R^4$-$R^5$ are hydrogen and $R^3$ is methyl; and $L^2$ is a nucleophilically displaceable leaving group; preferably halogen, $C_1$-$C_6$-alkylsulfonyloxy or $C_1$-$C_6$-haloalkylsulfonyloxy;

particularly preferably chlorine, bromine, iodine or trifluoromethylsulfonyloxy.

3-(2-Chloropyrid-3-yl)-4,5-dihydro-5-hydroxy-ethyl-5-methylisoxazole

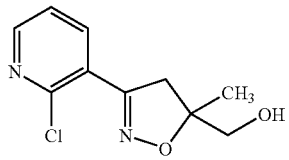

2.1

5.0 g (0.03 mol) of 2-chloropyrid-3-ylcarboxaldehyde oxime were initially charged in dimethylformamide, a spatula tip of N-chlorosuccinimide was added and the mixture was heated at 40-45° C. 4.26 g (0.03 mol) of N-chlorosuccinimide were then added a little at a time such that the reaction temperature did not exceed 50° C. After 1 h of stirring at 45-50° C., the mixture was hydrolyzed and extracted with diethyl ether, and the organic phase was dried. 2.07 g (0.03 mol) of 2-methyl-2-propenol were added to the resulting solution, and 5.37 g (0.04 mol) of triethylamine were added dropwise with ice-cooling. After 1 h, the reaction solution was allowed to warm to room temperature, the precipitate was filtered off and the solvent was removed. This gave 2.8 g (38.7% of theory) of the title compound (m.p. 71° C.).

5-(2,6-Difluorobenzyloxymethyl)-5-methyl-3-(3-propylisoxazol-5-yl)-4,5-dihydroisoxazole

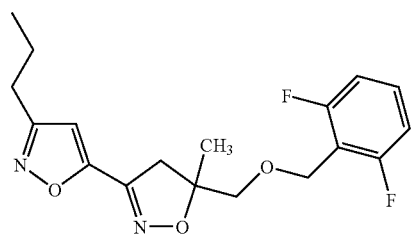

4.7

3 g (0.02 mol) of 3-propylisoxazol-5-ylcarbaldehyde oxime were dissolved in 20 ml of dimethylformamide, 0.29 g (0.002 mol) of N-chlorosuccinimide was added and the reaction mixture was heated to 45-50° C. Over a period of one hour, a further 2.31 g (0.02 mol) of N-chlorosuccinimide were added. The reaction mixture was then allowed to cool and subsequently poured into water. The phases were separated and the aqueous phase was extracted with diethyl ether. The combined organic phases were washed and dried, and 3.48 g (0.02 mol) of (2-methyl-prop-2-en)oxymethyl-2,6-difluorobenzene were added. At 0° C., 3 g (0.03 mol) of triethylamine were then slowly added dropwise, and the mixture was stirred at 0° C. for one hour. The resulting precipitate was filtered off and the solvent was removed from the filtrate. Customary purification methods gave 0.8 g (11.7% of theory) of the title compound.

In addition to the compounds above, Tables 2 to 5 list further 5-hydroxymethylisoxazolines of the formula III and 3-heteroaryl-substituted isoxazolines of the formula I which were prepared or are preparable in a manner analogous to the processes described above.

TABLE 2

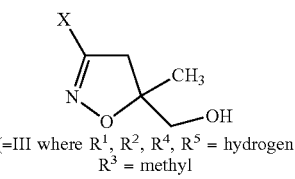

(=III where $R^1$, $R^2$, $R^4$, $R^5$ = hydrogen
$R^3$ = methyl)

| No. | X | selected $^1$H-NMR data [DMSO] or m.p. |
|---|---|---|
| 2.1 | 2-chloropyrid-3-yl | 71° C. |
| 2.2 | 6-methylpyrid-2-yl | |
| 2.3 | 2-chloro-5-methylimidazol-4-yl | |
| 2.4 | 3-methylisoxazol-5-yl | |
| 2.5 | 3-propylisoxazol-5-yl | |
| 2.6 | 4-(but-2-yl)isoxazol-5-yl | |
| 2.7 | 3-(2-methylpropyl)isoxazol-5-yl | |
| 2.8 | 3-phenylisoxazol-5-yl | |
| 2.9 | 2-methylthiazol-4-yl | |
| 2.10 | 2-methyl-5-chlorothiazol-4-yl | 3.22 (dd, 2H), 3.40 (dd, 2H) |

TABLE 3

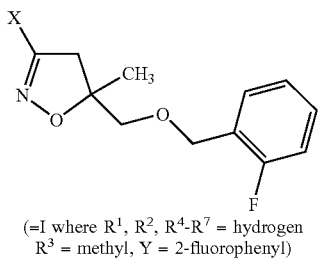

(=I where $R^1$, $R^2$, $R^4$-$R^7$ = hydrogen
$R^3$ = methyl, Y = 2-fluorophenyl)

| No. | X | selected $^1$H-NMR data [cm$^{-1}$]DMSO] or m.p. or MS [$^m$/e] or selected IR data [cm$^{-1}$] |
|---|---|---|
| 3.1 | 2-chloropyrid-3-yl | 3.31 (dd, 2H), 3.59 (dd, 2H) |
| 3.2 | 6-methylpyrid-2-yl | 3.27 (dd, 2H), 3.53 (dd, 2H) |
| 3.3 | 2-chloro-5-methylimidazol-4-yl | 3.30 (dd, 2H), 3.58 (dd, 2H) |
| 3.4 | 3-methylisoxazol-5-yl | 3.23 (dd, 2H), 3.57 (dd, 2H) |
| 3.5 | 3-propylisoxazol-5-yl | 3.25 (dd, 2H), 3.55 (dd, 2H) |
| 3.6 | 4-(but-2-yl)isoxazol-5-yl | 3.25 (dd, 2H), 3.56 (dd, 2H) |
| 3.7 | 3-(2-methylpropyl)isoxazol-5-yl | [M + H] + 346 |
| 3.8 | 3-phenylisoxazol-5-yl | 90° C. |
| 3.9 | 2-methylthiazol-4-yl | 3.32 (dd, 2H), 3.52 (dd, 2H) |
| 3.10 | 2-methyl-5-chlorothiazol-4-yl | 3.22 (dd, 2H), 3.50 (dd, 2H) |
| 3.11 | 4-chloropyrid-3-yl | 3.35 (dd, 2H), 3.59 (dd, 2H) |
| 3.12 | 2-chlorid-3-yl N-oxide | IR [cm$^{-1}$] 1259 N-oxide |
| 3.13 | 2,4-dichloropyrid-3-yl | 3.15 (dd, 2H), 3.60 (dd, 2H) |
| 3.14 | 2,6-dichloropyrid-3-yl | 3.32 (dd, 2H), 3.56 (dd, 2H) |
| 3.15 | 2-bromopyrid-3-yl | 3.28 (dd, 2H), 3.58 (dd, 2H) |
| 3.16 | 2-methylpyrid-3-yl | 3.28 (dd, 2H), 3.56 (dd, 2H) |

TABLE 3-continued

| No. | X | selected $^1$H-NMR data [cm$^{-1}$]DMSO] or m.p. or MS [$^m$/e] or selected IR data [cm$^{-1}$] |
|---|---|---|
| 3.17 | 2-trifluoromethylpyrid-3-yl | 3.26 (dd, 2H), 3.58 (dd, 2H) |
| 3.18 | 4-trifluoromethylpyrid-3-yl | 3.3 (dd, 2H), 3.55 (dd, 2H) |
| 3.19 | 2-methoxypyridin-3-yl | 3.27 (dd, 2H), 3.54 (dd, 2H) |
| 3.20 | 6-methoxypyridin-3-yl | 3.25 (dd, 2H), 3.53 (dd, 2H) |
| 3.21 | 2-chloro-4-isopropylpyrid-3-yl | 3.3 (dd, 2H), 3.55 (dd, 2H) |
| 3.22 | 2-chloro-6-methylpyrid-3-yl | 3.35 (dd, 2H), 3.54 (dd, 2H) |
| 3.23 | 2-chloro-4,6-dimethyl-pyrid-3-yl | 3.12 (dd, 2H), 3.57 (dd, 2H) |
| 3.24 | 2,6-dichloro-4-methyl-pyridin-3-yl | 3.18 (dd, 2H), 3.59 (dd, 2H) |
| 3.25 | 3-chloropyrid-4-yl | 3.32 (dd, 2H), 3.62 (dd, 2H) |
| 3.26 | 3-bromopyrid-4-yl | 3.38 (dd, 2H), 3.58 (dd, 2H) |
| 3.27 | 2-methylpyrid-4-yl | 3.24 (dd, 2H), 3.58 (dd, 2H) |
| 3.28 | 3-trifluoromethylpyrid-4-yl | 3.25 (dd, 2H), 3.57 (dd, 2H) |
| 3.29 | 2-trifluoromethyl-5-chloro-pyrid-4-yl | 3.43 (dd, 2H), 3.59 (dd, 2H) |
| 3.30 | 2-cyclopropylpyrimidin-4-yl | 3.25 (dd, 2H), 3.58 (dd, 2H) |
| 3.31 | 2-phenyl-4-methyl-pyrimidin-6-yl | 3.35 (dd, 2H), 3.60 (dd, 2H) |
| 3.32 | 3-chloropyrazin-2-yl | 3.4 (dd, 2H), 3.68 (dd, 2H) |
| 3.33 | 1-methyl-4,5-dichloroimidazol-2-yl | 3.24 (dd, 2H), 3.57 (dd, 2H) |
| 3.34 | 1,4-dimethyl-2-chloroimidazol-2-yl | 3.31 (dd, 2H), 3.57 (dd, 2H) |
| 3.35 | 3-methyl-4-chloroisoxazol-5-yl | 3.28 (dd, 2H), 3.57 (dd, 2H) |
| 3.36 | "2-chloropyrid-3-yl" methylsulfonic acid salt | 1492, 1456, 1351, 1194, 1058, 785, 772, 761, 536 |

TABLE 4

(=I where $R^1$, $R^2$, $R^4$-$R^7$ = hydrogen
$R^3$ = methyl, Y = 2,6-difluorophenyl)

| No. | X | selected $^1$H-NMR data [DMSO] or m.p. or MS [$^m$/e] |
|---|---|---|
| 4.1 | 2-chloropyrid-3-yl | 3.33 (dd, 2H), 3.53 (dd, 2H) |
| 4.2 | 6-methylpyrid-2-yl | 70° C. |
| 4.3 | 2-chloro-5-methylimidazol-4-yl | [M + H] + 356 |
| 4.4 | 3-methylisoxazol-5-yl | 3.20 (dd, 2H), 3.54 (dd, 2H) |
| 4.5 | 3-propylisoxazol-5-yl | 3.22 (dd, 2H), 3.52 (dd, 2H) |
| 4.6 | 4-(but-2-yl)isoxazol-5-yl | 3.18 (dd, 2H), 3.53 (dd, 2H) |
| 4.7 | 3-(2-methylpropyl)isoxazol-5-yl | 3.19 (dd, 2H), 3.53 (dd, 2H) |
| 4.8 | 3-phenylisoxazol-5-yl | 79-81° C. |
| 4.9 | 2-methylthiazol-4-yl | 3.18 (dd, 2H), 3.51 (dd, 2H) |
| 4.10 | 2-methyl-5-chlorothiazol-4-yl | 3.22 (dd, 2H), 3.50 (dd, 2H) |
| 4.11 | 3-chloropyrid-2-yl | m.p. 102° C. |
| 4.12 | 3-methylpyrid-2-yl | 3.34 (dd, 2H), 3.55 (dd, 2H) |
| 4.13 | trifluoromethylpyrid-2-yl | m.p. 95-96° C. |
| 4.14 | 2-fluoropyrid-3-yl | 3.26 (dd, 2H), 3.53 (dd, 2H) |
| 4.15 | 2-fluoropyrid-3-yl | 3.32 (dd, 2H), 3.56 (dd, 2H) |
| 4.16 | 2-bromopyrid-3-yl | 3.22 (dd, 2H), 3.55 (dd, 2H) |

TABLE 4-continued (=I where R$^1$, R$^2$, R$^4$-R$^7$ = hydrogen
R$^3$ = methyl, Y = 2,6-difluorophenyl)

| No. | X | selected $^1$H-NMR data [DMSO] or m.p. or MS [m/e] |
|---|---|---|
| 4.17 | 2,4-dichloropyrid-3-yl | 3.09 (dd, 2H), 3.59 (dd, 2H) |
| 4.18 | 2,4-dichloropyrid-3-yl | 3.28 (dd, 2H), 3.56 (dd, 2H) |
| 4.19 | 2-chloropyrid-3-yl N-oxide | [M]$^+$ 368 |
| 4.20 | 2-cyanopyrid-3-yl | 3.48 (dd, 2H), 3.61 (dd, 2H) |
| 4.21 | 2-hydroxypyrid-3-yl | 3.38 (dd, 2H), 3.52 (dd, 2H) |
| 4.22 | 2-nitropyrid-3-yl | 3.08 (dd, 2H), 3.60 (dd, 2H) |
| 4.23 | 2-methylpyrid-3-yl | m.p. 85° C. |
| 4.24 | 4-methylpyrid-3-yl | 3.30 (dd, 2H), 3.57 (dd, 2H) |
| 4.25 | 2-ethylpyrid-3-yl | 3.20 (dd, 2H), 3.58 (dd, 2H) |
| 4.26 | 2-trifluoromethylpyrid-3-yl | 3.20 (dd, 2H), 3.51 (dd, 2H) |
| 4.27 | 4-trifluoromethylpyrid-3-yl | 3.23 (dd, 2H), 3.53 (dd, 2H) |
| 4.28 | 2-methoxypyrid-3-yl | 3.24 (dd, 2H), 3.52 (dd, 2H) |
| 4.29 | 2(methylthio)pyrid-3-yl | m.p. 97-98° C. |
| 4.30 | 2(methylsulfonyl)pyrid-3-yl | IR: 1312 cm$^{-1}$ (SO$_2$) |
| 4.31 | 2(methylsulfonix)pyrid-3-yl | $^{13}$C-NMR: 87.27, 87.20 |
| 4.32 | 2(dimethylamino)pyrid-3-y2. | [M + H]$^+$ 362 |
| 4.33 | 2(phenylthio)pyrid-3-yl | 3.31 (dd, 2H), 3.58 (dd, 2H) |
| 4.34 | 2-chloro-6-methylpyrid-3-yl | 3.3 (dd, 2H), 3.55 (dd, 2H) |
| 4.35 | 2-chloro-4-isopropylpyrid-3-yl | 3.26 (dd, 2H), 3.54 (dd, 2H) |
| 4.36 | 2-chloro-4,6-dimethyl-pyrid-3-yl | 3.11 (dd, 2H), 3.58 (dd, 2H) |
| 4.37 | 2-methyl-4-chloropyride | 3.1 (dd, 2H), 3.54 (dd, 2H) |
| 4.38 | 3-chloropyrid-4-yl | 3.34 (dd, 2H), 3.56 (dd, 2H) |
| 4.39 | 3-bromopyrid-4-yl | 3.3 (dd, 2H), 3.55 (dd, 2H) |
| 4.40 | 3-trifluoromethylpyrid-4-yl | 3.25 (dd, 2H), 3.55 (dd, 2H) |
| 4.41 | 2-trifluoromethyl-5-chloro-pyrid-4-yl | m.p. 60° C. |
| 4.42 | 2-methylpyrimidin-4-yl | m.p. 89° C. |
| 4.43 | 2-cyclopropylpyrimidin-4-yl | 3.26 (dd, 2H), 3.58 (dd, 2H) |
| 4.44 | 3-chloropyrazin-2-yl | 3.3 (dd, 2H), 3.58 (dd, 2H) |
| 4.45 | 5-methylfuran-2-yl | 3.03 (dd, 2H), 3.46 (dd, 2H) |
| 4.46 | 3-chloro-5-chloromethylfuran-2-yl | 3.24 (dd, 2H), 3.58 (dd, 2H) |
| 4.47 | 3-methoxycarbonylfuran-2-yl | 3.3 (dd, 2H), 3.54 (dd, 2H) |
| 4.48 | 1-methyl-4,5-dichloroimidazol-2-yl | m.p. 86° C. |
| 4.49 | 3-methyl-4-chloroisoxazol-5-yl | 3.3 (dd, 2H), 3.54 (dd, 2H) |
| 4.50 | 1-methyl-3,5-dichloropyrrol-2-yl | [M + H]$^+$ 389 |
| 4.51 | 2-ethenylpyrid-3-yl | 3.3 (dd, 2H), 3.54 (dd, 2H) |
| 4.52 | 2-acetylpyrid-3-yl | [M + H]$^+$ 361 |

TABLE 5

(I where R$^1$, R$^2$, R$^4$-R$^7$ = hydrogen, R$^3$ = methyl)

| No. | X | Y | selected $^1$H-NMR data or MS |
|---|---|---|---|
| 5.1 | 2-chloropyrid-3-yl | phenyl | 3.4 (dd, 2H), 3.56 (dd, 2H) |
| 5.2 | 2-chloropyrid-3-yl | 3-fluorophenyl | 335 [M + H]$^+$ |
| 5.3 | 2-chloropyrid-3-yl | 2-chlorophenyl | 351 [M + H]$^+$ |
| 5.4 | 2-chloropyrid-3-yl | 2,6-dichlorophenyl | 385 [M + H]$^+$ |
| 5.5 | 2-chloropyrid-3-yl | 2,3,6-trichlorophenyl | 419 [M + H]$^+$ |
| 5.6 | 2-chloropyrid-3-yl | 2-chloro-6-fluoro-phenyl | 3.28 (dd, 2H), 3.56 (dd, 2H) |
| 5.7 | 2-chloropyrid-3-yl | 4-methylphenyl | 331 [M + H]$^+$ |
| 5.8 | 2-chloropyrid-3-yl | 2-methylnaphthyl-1-yl | 381 [M + H]$^+$ |
| 5.9 | 2-chloropyrid-3-yl | 5-chloro-1-methyl-3-trifluoromethyl-pyrazol-4-yl | 423 [M + H]$^+$ |

Use

The 3-heteroaryl-substituted isoxazolines of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and harmful grasses in crops such as wheat, rice, maize, soya and cotton without causing any significant damage to the crop plants. This effect is mainly observed at low rates of application.

Depending on the application method used, the compounds of the formula I or the herbicidal compositions comprising them can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays.*

In addition, the compounds of the formula I may also be used in crops which tolerate the action of herbicides owing to breeding, including genetic engineering methods.

The compounds of the formula I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting or granules, by means of spraying, atomizing, dusting, broadcasting or watering. The use forms depend on the intended aims; in any case, they should ensure a very fine distribution of the active compounds according to the invention.

The herbicidal compositions comprise a herbicidally effective amount of at least one compound of the formula I or an agriculturally useful salt of I and auxiliaries customary for formulating crop protection agents.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substrates, either as such or dissolved in an oil or solvent, can be homogenized in water by means of a wetting agent, tackifier, dispersant or emulsifier. Alternatively, it is also possible to prepare concentrates consisting of active substance, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl polyglycol ether or tributylphenyl polyglycol ether, alkylaryl polyether alcohols, isotridecyl alcohol, fatty alcohol ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or grinding the active substances together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise from about 0.001 to 98% by weight, preferably 0.01 to 95% by weight of at least one active compound. The active compounds are employed in a purity of from 90% to 100%, preferably from 95% to 100% (according to the NMR spectrum).

The production of such preparations is illustrated by the following formulation examples:

I. 20 parts by weight of an active compound of the formula I are dissolved in a mixture consisting of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound of formula I.

II. 20 parts by weight of an active compound of the formula I are dissolved in a mixture consisting of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound of formula I.

III. 20 parts by weight of an active compound of the formula I are dissolved in a mixture consisting of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound of formula I.

IV. 20 parts by weight of an active compound of the formula I are mixed thoroughly with 3 parts by weight of sodium diisobutylnaphthalenesulfonate, 17 parts by weight of the sodium salt of lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound of formula I.

V. 3 parts by weight of an active compound of the formula I are mixed with 97 parts by weight of finely divided kaolin. This gives a dust which comprises 3% by weight of the active compound of formula I.

VI. 20 parts by weight of an active compound of the formula I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of an active compound of the formula I is dissolved in a mixture consisting of 70 parts by weight of cyclohexanone, 20 parts by weight of ethoxylated isooctylphenol and 10 parts by weight of ethoxylated castor oil. This gives a stable emulsion concentrate.

VIII. 1 part by weight of an active compound of the formula I is dissolved in a mixture of 80 parts by weight of cyclohexanone and 20 parts by weight of Wettol® EM 31 (=nonionic emulsifier based on ethoxylated castor oil). This gives a stable emulsion concentrate.

The compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The application rates of the compound of the formula I are from 0.001 to 3.0, preferably from 0.01 to 1.0 kg/ha of active substance (a.s.), depending on the control target, the season, the target plants and the growth stage.

To widen the activity spectrum and to achieve synergistic effects, the 3-heteroaryl-substituted isoxazolines of the formula I may be mixed with a large number of representatives of other herbicidal or growth-regulating active compound groups and are applied concomitantly. Suitable components for mixtures are, for example, 1,2,4-thiadiazoles, 1,3,4-thiadiazoles, amides, aminophosphoric acid and its derivatives, aminotriazoles, anilides, (hetero)aryloxyalkanoic acids and their derivatives, benzoic acid and its derivatives, benzothiadiazinones, 2-(hetaroyl/aroyl)-1,3-cyclohexanediones, heteroarylaryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ether, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or else concomitantly in combination with other herbicides, or in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

USE EXAMPLES

The herbicidal activity of 3-heteroaryl-substituted isoxazolines of the formula I was demonstrated by the following greenhouse experiments:

The cultivation containers used were plastic flower pots containing loamy sand with approximately 3.0% of humus as the substrate. The seeds of the test plants were sown separately for each species.

For the pre-emergence treatment, directly after sowing the active compounds, which had been suspended or emulsified in water, were applied by means of finely distributing nozzles. The containers were irrigated gently to promote germination and growth and subsequently covered with transparent plastic hoods until the plants had rooted. This cover caused uniform germination of the test plants, unless this was adversely affected by the active compounds. The application rate for the post-emergence treatment was 3.0 kg/ha a.s. (active substance).

For the post-emergence treatment, the test plants were first grown to a height of from 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment.

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the above-ground parts and 0 means no damage, or normal course of growth.

The plants used in the greenhouse experiments were of the following species:

| Scientific name | Common name |
|---|---|
| Abutilon theophrasti | velvet leaf |
| Avena fatua | wild oat |
| Lolium multiflorum | Italian ryegrass |
| Setaria italica | foxtail millet |

At application rates of 3.0 kg/ha, the compounds 3.16, 3.17, 3.27, 3.36, 4.29 and 4.38 showed very good preemergence activity in the harmful plants *Solium multiflorum* and *Setaria italica*.

At application rates of 3.0 kg/ha, the pre-emergence activity of compound 4.1 on the harmful plants *Lolium multiflorum* and *Setaria italica* is very good.

At application rates of 3.0 kg/ha, the compound 4.1 showed very good post-emergence activity in the unwanted plants *Abutilon theophrasti*, *Avena fatua* and *Setaria italica*.

We claim:
1. A 3-heteroaryl-substituted isoxazoline of the formula I

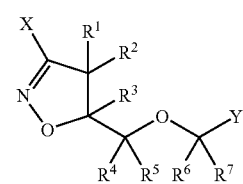

where:
X is pyridyl, which is partially or fully halogenated and/or carries one to three substituents selected from the following group:
cyano, nitro, hydroxyl, $C_1$-$C_8$-alkyl, $C_3$-$C_6$-cycloalkyl, $C_3$-$C_6$-halocycloalkyl, $C_2$-$C_8$-alkenyl, $C_2$-$C_8$-alkynyl, $C_1$-$C_8$-haloalkyl, $C_2$-$C_6$-haloalkenyl, $C_2$-$C_6$-haloalkynyl, $C_1$-$C_8$-cyanoalkyl, $C_2$-$C_8$-cyanoalkenyl, $C_1$-$C_8$-alkoxy, $C_1$-$C_8$-haloalkoxy, $C_1$-$C_8$-alkoxy-$C_1$-$C_8$-alkyl, $C_1$-$C_8$-alkoxy-$C_1$-$C_8$-alkoxy, amino, $C_1$-$C_8$-alkylamino, di($C_1$-$C_8$-alkyl)amino, $C_1$-$C_8$-alkylcarbonylamino, N—$C_1$-$C_8$-alkylcarbonyl-N—$C_1$-$C_8$-alkylamino, $C_1$-$C_8$-alkoxycarbonylamino, N—$C_1$-$C_8$-alkoxycarbonyl-N—$C_1$-$C_8$-alkylamino, amino-$C_1$-$C_8$-alkyl, $C_1$-$C_8$-alkylamino-$C_1$-$C_8$-alkyl, di($C_1$-$C_8$-alkyl)amino-$C_1$-$C_8$-alkyl, $C_1$-$C_8$-alkylthio, $C_1$-$C_8$-haloalkylthio, $C_1$-$C_8$-alkylthio-$C_1$-$C_8$-alkyl, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$- alkylsulfonyl-$C_1$-$C_8$-alkyl, $C_1$-$C_8$-alkylcarbonyl, $C_1$-$C_8$-alkoxycarbonyl, $C_1$-$C_8$-alkoxycarbonyl-$C_1$-$C_8$-alkyl, aminocarbonyl, $C_1$-$C_8$-alkylaminocarbonyl, di($C_1$-$C_8$-alkyl)aminocarbonyl, aminocarbonyl-$C_1$-$C_8$-alkyl, $C_1$-$C_8$-alkylaminocarbonyl-$C_1$-$C_8$-alkyl, di($C_1$-$C_8$-alkyl)aminocarbonyl-$C_1$-$C_8$-alkyl, carboxyl, carboxyl-$C_1$-$C_8$-alkyl, phenyl, phenoxy, phenylthio, phenylamino, phenyl-$C_1$-$C_8$-alkyl and phenyl-$C_1$-$C_8$-alkoxy, where the six last-mentioned radicals for their part may be partially or fully halogenated and/or may carry one to three substituents selected from the group consisting of nitro, cyano, $C_1$-$C_8$-alkyl, $C_1$-$C_8$-alkoxy, $C_1$-$C_8$-haloalkyl, $C_1$-$C_8$-haloalkoxy, $C_1$-$C_8$-alkylthio, $C_1$-$C_8$-haloalkylthio, $C_1$-$C_8$-alkylsulfinyl, $C_1$-$C_8$-haloalkylsulfinyl, $C_1$-$C_8$-alkylsulfonyl and $C_1$-$C_8$-haloalkylsulfonyl;

$R^1$-$R^7$ are hydrogen, $C_1$-$C_6$-alkyl or $C_1$-$C_6$-haloalkyl;

Y is aryl which may be partially or fully halogenated and/or may carry one to three substituents selected from the group consisting of cyano, nitro, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkoxycarbonyl, $C_1$-$C_6$-alkoxycarbonyl-$C_1$-$C_4$-alkoxy, $C_1$-$C_6$-alkylsulfonyl, phenyl, phenoxy and phenylcarbonyl;

or an agriculturally useful salt thereof.

2. A process for preparing 3-heteroaryl-substituted isoxazolines of the formula I as claimed in claim 1, which comprises reacting an arylmethyl allyl ether of the formula XI

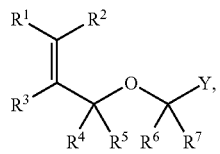

where X and $R^1$-$R^7$ are as defined in claim 1, with an nitride oxide formula V

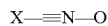        V, where X is as defined in claim 1.

3. A composition, comprising a herbicidally effective amount of at least one or more 3-heteroaryl-substituted isoxazoline(s) of the formula I or an agriculturally useful salt of I as claimed in claim 1 and auxiliaries customary for formulating crop protection agents.

4. A method for controlling unwanted vegetation, which comprises allowing a herbicidally effective amount of one or more 3-heteroaryl-substituted isoxazoline(s) of the formula I as claimed in claim 1 or an agriculturally useful salt of I to act on plants, their habitat and/or on seeds.

5. A 3heteroaryl-substituted isoxazoline of the formula I as claimed in claim 1, wherein X is pyridyl, which is attached to the isoxazoline skeleton in a position ortho or meta to a ring nitrogen, and which is partially or fully halogenated and/or carries one or two substituents selected from the following group:

cyano, nitro hydroxyl, $C_1$-$C_8$-alkyl, $C_3$-$C_6$-cycloalkyl, $C_3$-$C_6$-halocy-cloalkyl, $C_2$-$C_8$-alkenyl, $C_2$-$C_8$-alkynyl, $C_1$-$C_8$-haloalkyl, $C_2$-$C_6$-haloalkenyl, $C_2$-$C_6$haloalkynyl, $C_1$-$C_8$-cyanoalkyl, $C_2$-$C_8$-cyanoalkenyl, $C_1$-$C_8$-alkoxy, $C_1$-$C_8$-haloalkoxy, $C_1$-$C_8$-alkoxy-$C_1$-$C_8$-alkyl, $C_1$-$C_8$-alkoxy-$C_1$-$C_8$-alkoxy, amino, $C_1$-$C_8$-alkylamino, di($C_1$-$C_8$-alkyl)amino, $C_1$-$C_8$-alkylcarbonylamino, N—$C_1$-$C_8$-alkylcarbonyl-N—$C_1$-$C_8$-alkylamino, $C_1$-$C_8$-alkoxycarbonylamino, N—$C_1$-$C_8$-alkoxycarbonyl-N—$C_1$-$C_8$alkylamino, amino-$C_1$-$C_8$-alkyl, $C_1$-$C_8$-alkylamino-$C_1$-$C_8$-alkyl, di($C_1$-$C_8$-alkyl)amino-$C_1$-$C_8$-alkyl, $C_1$-$C_8$-alkylthio, $C_1$-$C_8$-haloalkylthio, $C_1$-$C_8$-alkylthio-$C_1$-$C_8$-alkyl, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylsulfonyl-$C_1$-$C_8$-alkyl, $C_1$-$C_8$-alkylcarbonyl, $C_1$-$C_8$-alkoxycarbonyl, $C_1$-$C_8$-alkoxycarbonyl-$C_1$-$C_8$-alkyl, aminocarbonyl, $C_1$-$C_8$-alkylaminocarbonyl, di($C_1$-$C_8$-alkyl)aminocarbonyl, aminocarbonyl-$C_1$-$C_8$-alkyl, $C_1$-$C_8$-alkylaminocarbonyl-$C_1$-$C_8$-alkyl, di($C_1$-$C_8$-alkyl)aminocarbonyl-$C_1$-$C_8$-alkyl, carboxyl and carboxyl-$C_1$-$C_8$-alkyl.

6. A 3-heteroaryl-substituted isoxazoline of the formula I as claimed in claim 1, wherein X is pyridyl, which is attached to the isoxazoline skeleton in a position ortho or meta to a ring nitrogen, and which is partially or fully halogenated and/or carries in a position ortho to a nitrogen atom, one or two substituents selected from the following group:

cyano, nitro, hydroxyl, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, $C_1$-$C_6$-haloalkoxy, amino, $C_1$-$C_6$-alkylamino, di($C_1$-$C_6$-alkyl) amino, $C_1$-$C_6$-alkylthio and $C_1$-$C_6$-alkyl-sulfinyl.

7. A 3-heteroaryl-substituted isoxazoline of the formula I as claimed in claim 1, wherein X is pyridyl, which is partially or fully halogenated and/or carries one to three substituents selected from the following group:

cyano, nitro hydroxyl, $C_1$-$C_8$-alkyl, $C_3$-$C_6$-cycloalkyl, $C_3$-$C_6$-halocycloalkyl, $C_2$-$C_8$-alkenyl, $C_2$-$C_8$-alkynyl, $C_1$-$C_8$-haloalkyl, $C_2$-$C_6$-haloalkenyl, $C_2$-$C_6$-haloalkynyl, $C_1$-$C_8$-cyanoalkyl, $C_2$-$C_8$-cyanoalkenyl, $C_1$-$C_8$-alkoxy, $C_1$-$C_8$-haloalkoxy, $C_1$-$C_8$-alkoxy-$C_1$-$C_8$-alkyl, $C_1$-$C_8$-alkoxy-$C_1$-$C_8$-alkoxy, amino, $C_1$-$C_8$-alkylamino, di($C_1$-$C_8$-alkyl)amino, $C_1$-$C_8$-alkylcarbonylamino, N—$C_1$-$C_8$-alkylcarbonyl-N—$C_1$-$C_8$-alkylamino, $C_1$-$C_8$-alkoxycarbonylamino, N—$C_1$-$C_8$-alkoxycarbonyl-N—$C_1$-$C_8$-alkylamino, amino-$C_1$-$C_8$-alkyl, $C_1$-$C_8$-alkylamino-$C_1$-$C_8$-alkyl, di($C_1$-$C_8$-alkyl) amino-$C_1$-$C_8$-alkyl, $C_1$-$C_8$-alkylthio, $C_1$-$C_8$-haloalkylthio, $C_1$-$C_8$-alkylthio-$C_1$-$C_8$-alkyl, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylsulfonyl-$C_1$$C_8$-alkyl, $C_1$-$C_8$-alkylcarbonyl, $C_1$-$C_8$-alkoxycarbonyl, $C_1$-$C_8$-alkoxycarbonyl-$C_1$-$C_8$-alkyl, aminocarbonyl, $C_1$-$C_8$-alkylaminocarbonyl, di($C_1$-$C_8$-alkyl)aminocarbonyl, aminocarbonyl-$C_1$-$C_8$-alkyl, $C_1$-$C_8$-alkylaminocarbonyl-$C_1$-$C_8$-alkyl, di($C_1$-$C_8$-alkyl)aminocarbonyl-$C_1$-$C_8$-alkyl, carboxyl and carboxyl-$C_1$-$C_8$-alkyl.

8. A 3-heteroaryl-substituted isoxazoline of the formula I as claimed in claim 1, wherein Y is phenyl, which may be partially or fully halogenated and/or may carry one to three substituents selected from the group consisting of:

cyano, nitro, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkoxycarbonyl, $C_1$-$C_6$-alkoxycarbonly-$C_1$-$C_4$-alkoxy, $C_1$-$C_6$-alkylsulfonyl, phenyl, phenoxy and phenylcarbonyl.

9. A 3-heteroaryl-substituted isoxazoline of the formula I as claimed in claim 1, wherein Y is phenyl, which is halogenated in the 2- and/or 6-position to a point of attachment and/or may carry one substituent from the group consisting of cyano, $C_1$-$C_4$-alkyl and $C_1$-$C_4$-halogenalkyl.

10. A 3heteroaryl-substituted isoxazoline of the formula I as claimed in claim 1, wherein the pyridyl ring X is attached to the isoxazoline skeleton in a position ortho or meta to the ring nitrogen of the pyridyl.

11. A 3heteroaryl-substituted isoxazoline of the formula I as claimed in claim 1, wherein the pyridyl ring X is attached to the isoxazoline skeleton in a position meta to the ring nitrogen of the pyridyl.

* * * * *

UNITED STATES PATENT AND TRADEMARK OFFICE
CERTIFICATE OF CORRECTION

PATENT NO. : 7,381,687 B2
APPLICATION NO. : 10/512451
DATED : June 3, 2008
INVENTOR(S) : Wagner et al.

It is certified that error appears in the above-identified patent and that said Letters Patent is hereby corrected as shown below:

On the Title page, item (22):
"Apr. 23, 2003" should read --Apr. 22, 2003--

In Claim 2, col. 61, indicated lines 28 and 29:
"3-heteroaryl-substituted isoxazolines" should read --a 3-heteroaryl-substituted isoxazoline--

In Claim 2, col. 61, indicated line 43:
"an nitride oxide formula V" should read --a nitrile oxide of the formula V--

In Claim 3, col. 61, indicated line 48:
"of at least one or more" should read --of one or more--

In Claim 5, col. 61, indicated line 57:
"3heteroaryl-substituted isoxazoline" should read --3-heteroaryl-substituted isoxazoline--

In Claim 5, col. 61, indicated line 64:
"$C_3$-$C_6$-halocy-cloalkyl" should read --$C_3$-$C_6$-halocycloalkyl--

In Claim 5, col. 61, indicated line 66:
"$C_2$-$C_6$haloalkynyl" should read --$C_2$-$C_6$-haloalkynyl--

In Claim 5, col. 62, indicated lines 4 and 5:
"N-$C_1$-$C_8$-alkoxycarbonyl-N-$C_1$-$C_8$alkylamino," should read --N-$C_1$-$C_8$-alkoxycarbonyl-N-$C_1$-$C_8$-alkylamino,--

In Claim 6, col. 62, indicated line 28:
"$C_1$-$C_6$-alkyl-sulfinyl," should read --$C_1$-$C_6$-alkylsulfinyl,--

In Claim 10, col. 63, indicated line 3:
"3heteroaryl-substituted isoxazoline" should read --3-heteroaryl-substituted isoxazoline--

UNITED STATES PATENT AND TRADEMARK OFFICE
CERTIFICATE OF CORRECTION

PATENT NO. : 7,381,687 B2
APPLICATION NO. : 10/512451
DATED : June 3, 2008
INVENTOR(S) : Wagner et al.

It is certified that error appears in the above-identified patent and that said Letters Patent is hereby corrected as shown below:

In Claim 11, col. 64, indicated line 1:
"3heteroaryl-substituted isoxazoline" should read --3-heteroaryl-substituted isoxazoline--

Signed and Sealed this

Twelfth Day of August, 2008

JON W. DUDAS
*Director of the United States Patent and Trademark Office*